United States Patent
Burks, Jr. et al.

(10) Patent No.: US 6,486,311 B1
(45) Date of Patent: Nov. 26, 2002

(54) PEANUT ALLERGENS AND METHODS

(75) Inventors: A. Wesley Burks, Jr., Little Rock; J. Steven Stanley, North Little Rock; Gael Cockrell, Cabot; Nina E. King, Little Rock, all of AR (US); Hugh A. Sampson, Larchmont, NY (US); Ricki M. Helm; Gary A. Bannon, both of LIttle Rock, AR (US)

(73) Assignees: Mt. Sinai School of Medicine, New York, NY (US); University of Arkansas, Littlerock, AR (US)

( * ) Notice: Subject to any disclaimer, the term of this patent is extended or adjusted under 35 U.S.C. 154(b) by 0 days.

(21) Appl. No.: 09/106,872

(22) Filed: Jun. 29, 1998

Related U.S. Application Data

(63) Continuation-in-part of application No. PCT/US96/15222, filed on Sep. 23, 1996, which is a continuation-in-part of application No. 08/610,424, filed on Mar. 4, 1996
(60) Provisional application No. 60/009,455, filed on Dec. 29, 1995.

(51) Int. Cl.$^7$ ............................................... C07H 21/04
(52) U.S. Cl. ................. 536/23.6; 435/252.3; 424/184.1
(58) Field of Search ........................ 536/23.6; 435/69.3, 435/252.3; 424/184.1

(56) References Cited

PUBLICATIONS

Scheiner, "Recombinant allergens: biological, immunological and practical aspects," *Int. Arch. Allergy Immunol.* 98:93–96 (1992).
Secrist, et al., "Allergen immunotherapy decreases interleukin 4 production in CD4+ T cells from allergic individuals," *J. Exp. Med.* 178: 2123–2130 (1993).
Shanti, et al. "Identification of tropomyosin as the major shrimp allergen and characterization of its IgE–binding epitopes," *J. Immunol.* 151, 5354–5363 (1993).
Sparholt, et al., "the allergen specific B–cell response during immunotherapy," *Clinical and Experimental Allergy* 22: 648–653 (1992).
Taylor, et al., "Peanut oil is not allergenic to peanut sensitive individuals," *J. Allergy Clin. Immunol.* 68: 372–375 (1981).
Van Der Stoep, et al., In vivo and in vitro IgE isotype switching in human B lymphocytes: evidence for a predominantly direct IgM to IgE class switch program. *European J. Immunol* 24: 1307–1311 (1994).
Van Kampen, et al., "Analysis of B–cell epitopes in the N–terminal region of Chi t I component III using monoclonal antibodies," *MolecularImmunol.* 31: 1133–1140 (1994).
Yunginger, et al., "Fatal food–induced anaphylaxis," *JAMA* 260: 1450–1452 (1988).
Burks, et al., "Epitope specificity and immunoaffinity purification of the major peanut allergen, Ara h I," *J Allergy Clin Immunol.* 93(4): 743–50 (1994).
Burks, et al., "Epitope specificity of the major peanut allergen, Ara h II," *J Allergy Clin Immunol.* 95(2):607–11. (1995).
Burks, et al., "Identification and characterization of a second major peanut allergen, Ara h II, with use of the sera of patients with atopic dermatitis and positive peanut challenge," *J Allergy Clin Immunol.* 90(6 Pt 1): 962–9 (1992).
Burks, et al., "Identification of a major peanut allergen Ara h I, in patients with atopic dermatitis and positive peanut challenge," *J. Allergy Clin. Immunol.* 88:172–179 (1991).
Burks, et al., "Identification of peanut agglutinin and soybean trypsin inhibitor as minor legume allergens," *Int Arch Allergy Immunol.* 105(2):143–149 (1994).
Burks, et al., "Isolation, identification, and characterization of clones encoding antigens responsible for peanut hypersensitivity," *Int Arch Allergy Immunol.* 107(1–3): 248–50 (1995).
Elsayed, et al., "Synthetic allergenic epitopes from the amino–terminal regions of the major allergens of hazel and birch pollen," *Int. Arch. Allergy Appl. Immunol.* 89: 410–415 (1989).
Fitzsimmons, et al., "Immunothrapy– definition and mechanism," *Allergy Proc.* 11:156 (1990).
Fung–Leung, et al., "transgneic mice expressing the human high–affinity immunoglobulin (Ig) E receptor alpha chain respond to human IgE in mast cell degranualtion and in allergic reactions," *J. Exp. Med.* 183: 49–56 (1996).
Garcia, et al., "Nonspecific changes in immunotherapy with house dut extract," *J. Invest Alergol. Clin Immunol.* 5: 18–24 (1995).
Aas, et al., "Physico–chemical properties and specific activity of a purified allergen (codfish)," *Dev. Biol. Strand.* 29: 90–98 (1975).

(List continued on next page.)

*Primary Examiner*—Laurie Scheiner
(74) *Attorney, Agent, or Firm*—Brenda Herschbach Jarrell; Choate, Hall & Stewart

(57) ABSTRACT

Peanuts are a common cause of food hypersensitivity reactions. The sera of 10 patients who had atopic dermatitis and a positive double-blind placebo-controlled food challenge to peanut were used to investigate the major allergens of peanut. Crude Florunner extracts were fractionated by anion-exchange chromatography using a step gradient (limit buffer, 0.05M BisTris/1.5M NaCl). A protein peak (OD 280) which eluted at 10% NaCl and demonstrated intense IgE-binding was further analyzed by two-dimensional SDS-PAGE/immunoblot analysis. The majority of this fraction is a protein which has a molecular weight of 17 kD and a pI of 5.2. Sequencing data from the N-terminus revealed the following initial 9 amino acids: (*)-Q-Q-(*)-E-L-Q-D-L. Based on IgE-binding activity and no known amino acid sequence identity to other allergens, this allergen is designated Ara h II. Ara h II may be used to detect and quantify peanut allergens in foodstuffs. Serum IgE from patients with documented peanut hypersensitivity reactions and a peanut cDNA expression library were used to identify clones that encode peanut allergens.

8 Claims, 15 Drawing Sheets

OTHER PUBLICATIONS

Figure 1:
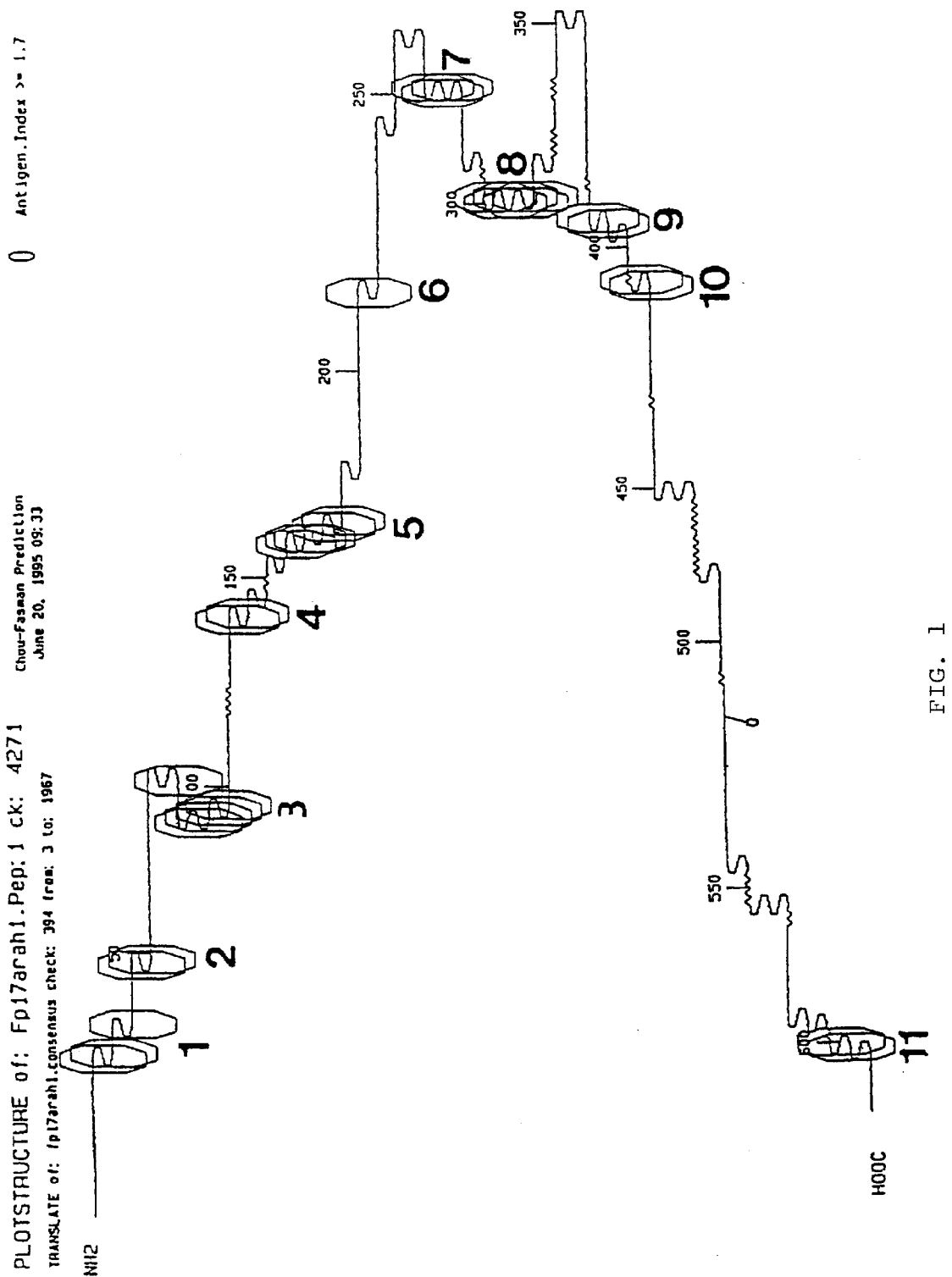

Ball, et al., "A major continuous allergenic epitope of bovine beta–lactoglobulin recognized by human IgE binding," *Clin. Exp. Allergy* 24: 758–764 (1994).

Bernhisel–Broadbent, et al., "Cross–allergenicity in the legume botanical family in children with food hypersensitivity. II. Laboratory correlates" *J Allergy Clin. Immunol.* 84:701–709 (1989).

Birkner, et al., "Evaluation of immunothrapy–induced changes in specific IgE, IgG, and IgG–subclasses in birch pollen–allergic patient by means of immunoblotting, Correlation with Clinical Response," *Allergy* 45: 418–426.

Bock, et al., "The natural history of peanut allergy," *J. Allergy Clin. Immunol.* 83: 900–904 (1989).

Breiteneder, et al., "Complementary DNA cloning and expression in *Escheria coli* of Aln g I, the major allergen in pollen odf alder (*Alnus glutinosa*)," *J. Allergy Clin. Immunol.* 90:909–917 (1992).

Burks, "Allergenicity of peanut and soybean extracts altered by chemical or thermal denaturation in patients with atopic dermatitis and positive food challenges," *J Allergy Clin Immunol* 90(6 pt 1): 889–97 (1992).

Burks, et al. "Atopic dermatitis: clinical relevance of food hypersensitivity reactions," *J. Pediatr.* 113: 447–451 (1988).

Burks, et al. "Mapping and mutational analysis of the IgE–binding epitopes on Ara h 1, a legume vicilin protein and a major allergen in peanut hypersensitivity," *Eur. J. Biochem.* 245: 334–339 (1997).

Burks, et al. "Recombinant peanut allergen Ara h I expression and IgE binding in patients with peanut hypersensitivity," *J. Clinical Invest.* 96: 1715–1721 (1995).

Gibbs, et al., "Evolution of legume seed storage proteins—a domain common to legumins and vicilins is duplicated in vicilins," *Mol. Biol. Evol.* 6: 614–623 (1989).

Gieni, et al., "Allergen–specific modulation of cytokins synthesis patterns and IgE responses in vivo with chemically modified allergen," *The Journal of Immunol.* 150:302–310 (1993).

Gordon, "Future immunotherapy: what lies ahead?" *Otolaryngol Head Neck Surg.* 113: 603–605 (1995).

Herian, et al. "Identification of soybean allergens by immunoblotting with sera from soy–allergic adults," *Int. Arch. Allergy Appl. Immunol.* 92: 193–198 (1990).

Jameson, et al., "The antigenic index: a novel algorithm for predicting antigenic determinants," *Comput. Appl. Biosci.* 4: 181–186 (1988).

Jansen, et al., "Prevalance of food allergy and intolerance in the adult Dutch population," *J. Allergy Clin. Immunol.* 93: 446–456 (1994).

Oppenheimer et al. "Treatment of peanut allergy with rush immunotherapy," *J Allergy Clin Immunol.* 90: 256–62 (1992).

Reisman, "Fifteen years of hymenoptera venom immunotherapy: changing concepts and lessons," *Allergy Proceedings* 15: 61–63 (1994).

Sampson, "The role of food allergy and mediator release in atopic dermatitis," *J. Allergy Clin. Immunol.* 81: 635–645 (1988).

Sampson, et al., "Fatal and near–fatal anaphylactic reactions to food in children and adolescents," *N Engl J Med* 327: 380–384 (1992).

Ara h II Clone

```
ACG AGG CTC ACC ATA CTA GTA GCC CTC GCC CTT TTC CTC CTC GCT GCC  48
Thr Arg Leu Thr Ile Leu Val Ala Leu Ala Leu Phe Leu Leu Ala Ala

CAC GCA TCT GCG AGG CAG CAG TGG GAA CTC CAA GGA GAC AGA AGA TGC  96
His Ala Ser Ala Arg Gln Gln Trp Glu Leu Gln Gly Asp Arg Arg Cys

CAG AGC CAG CTC GAG AGG GCG AAC CTG AGG CCC TGC GAG CAA CAT CTC 144
Gln Ser Gln Leu Glu Arg Ala Asn Leu Arg Pro Cys Glu Gln His Leu

ATG CAG AAG ATC CAA CGT GAC GAG GAT TCA TAT GAA CGG GAC CCG TAC 192
Met Gln Lys Ile Gln Arg Asp Glu Asp Ser Tyr Glu Arg Asp Pro Tyr

AGC CCT AGT CAG GAT CCG TAC AGC CCT AGT CCA TAT GAT CGG AGA GGC 240
Ser Pro Ser Gln Asp Pro Tyr Ser Pro Ser Pro Tyr Asp Arg Arg Gly

GCT GGA TCC TCT CAG CAC CAA GAG AGG TGT TGC AAT GAG CTG AAC GAG 288
Ala Gly Ser Ser Gln His Gln Glu Arg Cys Cys Asn Glu Leu Asn Glu

TTT GAG AAC AAC CAA AGG TGC ATG TGC GAG GCA TTG CAA CAG ATC ATG 336
Phe Glu Asn Asn Gln Arg Cys Met Cys Glu Ala Leu Gln Gln Ile Met

GAG AAC CAG AGC GAT AGG TTG CAG GGG AGG CAA CAG GAG CAA CAG TTC 384
Glu Asn Gln Ser Asp Arg Leu Gln Gly Arg Gln Gln Glu Gln Gln Phe

AAG AGG GAG CTC AGG AAC TTG CCT CAA CAG TGC GGC CTT AGG GCA CCA 432
Lys Arg Glu Leu Arg Asn Leu Pro Gln Gln Cys Gly Leu Arg Ala Pro

CAG CGT TGC GAC TTG GAC GTC GAA AGT GGC GGC AGA GAC AGA TAC TAA 480
Gln Arg Cys Asp Leu Asp Val Glu Ser Gly Gly Arg Asp Arg Tyr

ACACCTATCTCAAAAAAAGAAAAGAAAAGAAAAGAAAATAGCTTATATATAAGCTATTATCTATGGTTAT
GTTTAGTTTTGGTAATAATAAAGATCATCACTATATGAATGTGTTGATCGTGTTAACTAAGGCAAGCTTA
GGTTATATGAGCACCTTTAGAGTGCTTTTATGGCGTTGTCTATGTTTTGTTGCTGCAGAGTTGTAACCAT
CTTGAAATAATATAAAAAGATCATGTTTTGTTAAAAAAAAAAAAAAAAAAAAA
```

FIG. 6

Ara h II

Amino Acid
1-103
97-159

D1
TRCMCLKYMAHASA RQQWELQGDR RCQSQLERAN LRPCEQHLMQ 50
               D2              D3
KIQRDEDSYERDPYSPSQDP YSPSPYDRRG AUSSQHQERC CMELNEFENN 100
       P1                   P2
QRCMCEALQQ IMENQSDRLQ GRQQEQQFKR ELRNLPQQCG LRAPQRCDLD 150
  P3
D4
VESGGRDRY                                              159
  P4

☐ Predicted
☐ Determined

FIG. 8

A              3
              ● ● ●

B
        50      60      70
        |       |       |
        MQKIQRDEDSYERDPYSPSQDP
        MQKIQRDEDS
          KIQRDEDSYE
           IQRDEDSYERD
             DEDSYERDPY
              DSYERDPYSP
                 YERDPYSPSQ
                    RDPYSPSQDP

FIG. 9

● Y 59A

● E 60A

● R 61A

D 62A

P 63A

Y 64A

● S 65A

P 66A

● S 67A

● Q 68A

● WT

Epitope 3

FIG. 11

```
  1    AATAATCATATATATTCATCAATCATCTATATAAGTAGTAGCAGGAGCA
       -------------------------------------------------..

50    ATGAGAGGGAGGGTTTCTCCACTGATGCTGTTGCTAGGGATCCTTGTCCTG
       ..................................................

M  R  G  R  V  S  P  L  M  L  L  L  G  I  L  V  L   17

101    GCTTCAGTTTCTGCAACGCATGCCAAGTCATCACCTTACCAGAAGAAAAC
       ...................G.........C.------TT.CCG......

A  S  V  S  A  T  H  A  K  S  S  P  Y  Q  K  K  T   34

151    AGAGAACCCCTGCGCCCAGAGGTGCCTCCAGAGTTGTCAACAGGAACCGG
       ..................................................

E  N  P  C  A  Q  R  C  L  Q  S  C  Q  Q  E  P   50

201    ATGACTTGAAGCAAAAGGCATGCGAGTCTCGCTGCACCAAGCTCGAGTAT
       ..................................................

D  D  L  K  Q  K  A  C  E  S  R  C  T  K  L  E  Y   67

251    GATCCTCGTTGTGTCTATGATCCTCGAGGACACACTGGCACCACCAACCA
       ....................--------------........G..........

D  P  R  C  V  Y  D  P  R  G  H  T  G  T  T  N  Q   84

301    ACGTTCCCCTCCAGGGGAGCGGACACGTGGCCGCCAACCCGGAGACTACG
       ....CA............................................

R  S  P  P  G  E  R  T  R  G  R  Q  P  G  D  Y  100

351    ATGATGACCGCCGTCAACCCCGAAGAGAGGAAGGAGGCCGATGGGGACCA
       ..................................................

D  D  D  R  R  Q  P  R  R  E  E  G  G  R  W  G  P  117

401    GCTGGACCGAGGGAGCGTGAAAGAGAAGAAGACTGGAGACAACCAAGAGA
       ....A.............................................

A  G  P  R  E  R  E  R  E  E  D  W  R  Q  P  R  E  134
```

FIG. 12A

```
451    AGATTGGAGGCGACCAAGTCATCAGCAGCCACGGAAAATAAGGCCCGAAG
       ..................................................

D   W   R   R   P   S   H   Q   Q   P   R   K   I   R   P   E    150

501    GAAGAGAAGGAGAACAAGAGTGGGGAACACCAGGTAGCCATGTGAGGGAA
       ............................G.G..................

G   R   E   G   E   Q   E   W   G   T   P   G   S   H   V   R   E    167

551    GAAACATCTCGGAACAACCCTTTCTACTTCCCGTCAAGGCGGTTTAGCAC
       .......A..........................................

Peptide   E   T   S   R  | N   N   P   F   Y   F   P   S   R   R |  F   S   T    184
  III 601    CCGCTACGGGAACCAAAACGGTAGGATCCGGGTCCTGCAGAGGTTTGACC
       ..............................C..................

R   Y   G   N   Q   N   G   R   I   R   V   L   Q   R   F   D    200

651    AAAGGTCAAGGCAGTTTCAGAATCTCCAGAATCACCGTATTGTGCAGATC
       .........A........................................

Q   R   S   R   Q   F   Q   N   L   Q   N   H   R   I   V   Q   I    217

701    GAGGCCAAACCTAACACTCTTGTTCTTCCCAAGCACGCTGATGCTGATAA
       .......G..........................................

E   A   K   P   N   T   L   V   L   P   K   H   A   D   A   D   N    234

751    CATCCTTGTTATCCAGCAAGGGCAAGCCACCGTGACCGTAGCAAATGGCA
       ..............A...................................

I   L   V   I   Q   Q   G   Q   A   T   V   T   V   A   N   G    250

801    ATAACAGAAAGAGCTTTAATCTTGACGAGGGCCATGCACTCAGAATCCCA
       ..................................................

N   N   R   K   S   F   N   L   D   E   G   H   A   L   R   I   P    267

851    TCCGGTTTCATTTCCTACATCTTGAACCGCCATGACAACCAGAACCTCAG
       ..............................T..A...............

S   G   F   I   S   Y   I   L   N   R   H   D   N   Q   N   L   R    284

901    AGTAGCTAAAATCTCCATGCCCGTTAACACACCCGGCCAGTTTGAGGATT
       ...............................G..................

A   A   K   I   S   M   P   V   N   T   P   G   Q   F   E   D    300
```

FIG. 12B

```
951   TCTTCCCGGCGAGCAGCCGAGACCAATCATCCTACTTGCAGGGCTTCAGC
      ..............................A......

F  F  P  A  S  S  R  D  Q  S  S  Y  L  Q  G  F  S     317

1001  AGGAATACGTTGGAGGCCGCCTTCAATGCGGAATTCAATGAGATACGGAG
      ........T.........................................

R  N  T  L  E  A  A  F  N  A  E  F  N  E  I  R  R   334

1051  GGTGCTGTTAGAAGAGAATGCAGGAGGTGAGCAAGAGGAGAGAGGGCAGA
      ............................A.....................

V  L  L  E  E  N  A  G  G  E  Q  E  E  R  G  Q     350

1101  GGCGATGGAGTACTCGGAGTAGTGAGAACAATGAAGGAGTGATAGTCAAA
      .....C..............---.T.........................

R  R  W  S  T  R  S  S  E  N  N  E  G  V  I  V  K   367

1151  GTGTCAAAGGAGCACGTTGAAGAACTTACTAAGCACGCTAAATCCGTCTC
      ...............C..................................

V  S  K  E  H  V  E  E  L  T  K  H  A  K  S  V  S   384

1201  AAAGAAAGGCTCCGAAGAAGAGGGAGATATCACCAACCCAATCAACTTGA
      ....................A---.........................
```

Peptide II   K | K  G  S  E  E  E  G  D  I  T  N  P  I  N  L |   400

```
1251  GAGAAGGCGAGCCCGATCTTTCTAACAACTTTGGGAAGTTATTTGAGGTG
      ....T...........................G................
```

| R | E  G  E  P  D  L  S  N  N  F  G  K  L  F  E  V     417

```
1301  AAGCCAGACAAGAAGAACCCCCAGCTTCAGGACCTGGACATGATGCTCAC
      ..................................................

K  P  D  K  K  N  P  Q  L  Q  D  L  D  M  M  L  T   434

1351  CTGTGTAGAGATCAAAGAAGGAGCTTTGATGCTCCCACACTTCAACTCAA
      ..................................................

C  V  E  I  K  E  G  A  L  M  L  P  H  F  N  S     450
```

FIG. 12C

```
1401  AGGCCATGGTTATCGTCGTCGTCAACAAAGGAACTGGAAACCTTGAACTC
      ..........C.......................................

K  A  M  V  I  V  V  V  N  K  G  T  G  N  L  E  L    467

1451  GTGGCTGTAAGAAAAGAGCAACAACAGAGGGGACGGCGGGAA---------
      ...A..............................................CAAGAGTC

V  A  V  R  K  E  Q  Q  Q  R  G  R  R  E  -  -  -    481

1493  -GAAGAGGAGGACGAAGACGAAGAAGAGGAGGGAAGTAACAGAGAGGTGC
      G.....A.....G.....T...............................

E  E  E  D  E  D  E  E  E  E  G  S  N  R  E  V       497

1542  GTAGGTACACAGCGAGGTTGAAGGAAGGCGATGTTCATCATGCCAGCA
      ................................................

R  R  Y  T  A  R  L  K  E  G  D  V  F  I  M  P  A    514

1592  GCTCATCCAGTAGCCATCAACGCTTCCTCCGAACTCCATCTGCTTGGCTT
      ..................................................

A  H  P  V  A  I  N  A  S  S  E  L  H  L  L  G  F    531

1642  CGGTATCAACGCTGAAAACAACCACAGAATCTTCCTTGCAGGTGATAAGG
      ..................................................
```

Peptide I

```
       G  I  N  A  E  N  N  H  R │I  F  L  A  G  D  K│      547

1692  ACAATGTGATAGACCAGATAGAGAAGCAAGCGAAGGATTTAGCATTCCCT
      ..................................................

│D  N  V  I  D  Q  I  E  K│ Q  A  K  D  L  A  F  P    564

1742  GGGTCGGGTGAACAAGTTGAGAAGCTCATCAAAAACCAGAAGGAATCTCA
      ..T..........................................G...G.....

G  S  G  E  Q  V  E  K  L  I  K  N  Q  K  E  S  H    581

1792  CTTTGTGAGTGCTCGTCCTCAATCTCAATCTCAATCTCCGTCGTCTCCTG
      ...........................CG..-------------------

F  V  S  A  R  P  Q  S  Q  S  Q  S  P  S  S  P       597

1842  AGAAAGAGTCTCCTGAGAAAGAGGATCAAGAGGAGGAAAACCAAGGAGGG
      --------..........A...............................

E  K  E  S  P  E  K  E  D  Q  E  E  E  N  Q  G  G    614
```

FIG. 12D

```
1892    AAGGGTCCACTCCTTTCAATTTTGAAGGCTTTTAACTGAGAATGGGAGGCA
        ..................................G.............A.
         K  G  P  L  L  S  I  L  K  A  F  N                    626

1942    ACTTGTTATGTATCGATAATAAGATCACGCTTTTGTACTCTACTATCCAA
        .....................C...................A........

1992    AAACTTATCAATAAATAAAAACGTTTGTGCGTTGTTTCTCCAAAAAAAA
        ‾‾‾‾‾‾‾‾‾‾‾‾‾
```

Nucleotide sequence of an *Ara h* I cDNA clone. The ...ide sequence of clone 41B is shown on the first line. The line depicts clone P17 DNA sequence with dots (.) representing nucleotides that are the same, dashes (-) nucleotides that ...sing, and A, C, G, or T nucleotides that differ between DNA sequences. The protein synthesis start (ATG) and ...A) sites are underlined along with a consensus polyadenylation signal (AATAAA). Bold amino acid residues are those ...hich correspond to the determined amino acid sequence of peptides I, II, and III of *Ara h* I (Table 14). The numbers on the left of ...re indicate the nucleotide sequence, and those on the right correspond to the deduced amino acid sequence. These sequence data ...lable from GenBank under accession number L34402.

FIG. 12E

PEANUT ALLERGENS AND METHODS

This application is a continuation-in-part of PCT/US96/15222, filed Sep. 23, 1996, which claims priority to and is a C-I-P of application Ser. No. 08/610,424, filed Mar. 4, 1996, now U.S. Pat. No. 5,973,121, and to provisional application No. 60/009,455, filed Dec. 29, 1995.

Peanuts are considered one of the most allergenic foods.[1] Peanut allergy is a significant health problem because of the potential severity of the allergic reaction, the chronicity of the allergic sensitivity, and the ubiquity of peanut products. Individuals sensitive to peanuts may experience symptoms ranging from mild urticaria to severe, systemic anaphylaxis.[1] In food-induced, fatal anaphylaxis, peanuts are the food most commonly implicated in causing the reaction.[2,3] Sensitivity to peanuts often appears early in life, and unlike most other food allergies, tends to persist indefinitely.[4]

To elucidate the exact mechanism of IgE-mediated reactions, the identification and purification of the precise allergens are necessary. Significant information has accumulated in allergen C characterization from a wide variety of sources, including pollens, dust mite, animal danders, and insects.[5] In comparison, allergen characterization for even the most common food allergens is much less defined. Despite the significant prevalence of peanut hypersensitivity reactions and several deaths annually, the identification of the clinically relevant antigens and an understanding of the immunobiology of peanut hypersensitivity is just beginning.

Monoclonal antibodies are being increasingly used to define and characterize the allergenic epitopes of many allergens. Multiple allergens including the dust mite allergen, Der f I,[6] and the grass pollen allergen, Lol p I,[7] have been studied by using monoclonal antibodies. Murine monoclonal antibodies to these allergens have been shown to be quite effective in defining their allergenic epitopes.

In this report we have investigated the epitope specificity of Ara h II,[8] a major peanut allergen, by using monoclonal antibodies as probes for mapping the possible antigenic determinants. We have produced and characterized a panel of monoclonal antibodies specific to Ara h II. The Ara h II monoclonal antibodies allowed us to define at least two antigenic sites on Ara h II. Inhibition assays were used to determine the IgE-binding sites on Ara h II.

Methods

Patients with Positive Peanut Challenge Responses

Approval for this study was obtained from the Human Use Advisory Committee at the University of Arkansas for Medical Sciences. Twelve patients with atopic determatitis and a positive immediate prick skin test response to peanut had either a positive response to double-blind placebo-controlled food challenge (DBPCFC) or a convincing history of peanut anaphylaxis (the allergic reaction was potentially life-threatening, that is with laryngeal edema, severe wheezing, and/or hypotension). Details of the challenge procedure and interpretation have been previously discussed.[9] Five milliliters of venous blood was drawn from each patient and allowed to clot, and the serum was collected. An equal volume of serum from each donor was mixed to prepare a peanut-specific IgE antibody pool.

Crude Peanut Extract

Three commercial lots of Southeastern Runners peanuts (Arachis hypogaea), medium grade, from the 1979 crop (North Carolina State University) were used in this study. The peanuts were stored in the freezer at −18° C. until they were roasted. The three lots were combined in equal proportions and blended before defatting. The defatting process (defatted with hexane after roasting for 13 to 16 minutes at 163° C. to 177° C.) was done in the laboratory of Dr. Clyde Young (North Carolina State University). The powdered crude peanut was extracted in 1 mol/L NaCl, 20 mmol/L sodium phosphate (pH 7.0)[1] and 8 mol/L urea for 4 hours at 4° C. The extract was clarified by centrifugation at 20,000 g for 60 minutes at 4° C. The total protein determination was done by the bicinchoninic acid method (Pierce Laboratories, Rockville, Ill.).

Monoclonal Antibodies

Mouse hybridoma cell lines were prepared by standard selection after polyethylene glycol-mediated cell fusion was carried out as previously described.[10] $Sp^2/0$-$Ag^{14}$ mouse/myeloma cells were fused with immune splenocytes from female BALB/c mice hyperimmunized with Ara h II. Hybridoma cell supernatants were screened by ELISA and Western blotting, and cell lines were cloned by limiting dilution. The antibodies secreted by the monoclonal hybridoma cell lines were isotyped according the directions provided (Screen Type; Boehringer Mannhein, Indianapolis, Ind.). Ascites fluid produced in BALB/c mice was purified with Protein G Superose, as outlined by the manufacturer (Pharmacia, Uppsala, Sweden). Purified monoclonal antibodies were used in ELISA and ELISA inhibition assays.

ELISA for IgE

A biotin-avidin ELISA was developed to quantify IgE anti-peanut protein antibodies with modifications from an assay previously described.[11] The upper 2 rows of a 96-well microtiter plate (Gibco, Santa Clara, Calif.) were coated with 100 µl each of equal amounts (1 µg/ml) of anti-human IgE monoclonal antibodies, 7.12 and 4.15 (kindly provided by Dr. Andrew Saxon). The remainder of the plate was coated with the peanut protein at a concentration of 1 µg/ml in coating buffer (0.1 mol/L sodium carbonate-bicarbonate buffer, pH 9.6). The plate was incubated at 37° C. for 1 hour and then washed five times with rinse buffer (phosphate-buffered saline, pH 7.4, containing 0.05% Tween 20, Sigma Chemical Co., St. Louis, Mo.) immediately and between subsequent incubations. A secondary IgE reference standard was added to the upper 2 rows to generate a curve for IgE, ranging from 0.05 to 25 ng/ml.

The serum pool and patient serum samples were diluted (1:20 vol/vol) and dispensed into individual wells in the lower portion of the plate. After incubation for 1 hour at 37° C. and washing, biotinylated, affinity-purified goat anti-human IgE (KPL, Gaithersburg, Md.) (1:1000 vol/vol bovine serum albumin) was added to all wells. Plates were incubated for 1 hour at 37° C. and washed, and 100 µl horseradish peroxidase-avidin conjugate (Vector Laboratories, Burlingame, Calif.) was added for 5 minutes. After washing, the plates were developed by the addition of a citrate buffer containing O-phenylenediamine (Sigma Chemical Co.). The reaction was stopped by the addition of 100 µl 2N hydrochloric acid to each well, and absorbance was read at 490 nm (Bio-Rad Microplate reader model 450; Bio-Rad Laboratories Diagnostic Group, Hercules, Calif.). The standard curve was plotted on a log-logit scale by means of simple linear regression analysis, and values for the pooled serum and individual samples were read from the curve.[8,9]

ELISA Inhibition

An inhibition ELISA was developed to examine the site specificity of the monoclonal antibodies generated to Ara h II. One hundred microliters of Ara h II protein (1 mg/ml) was added to each well of a 96-well microtiter plate (Gibco) in coating buffer (carbonate buffer, pH 9.6) for 1 hour at 37° C. Next, 100 µl of differing concentrations (up to 1000-fold excess) of each of the monoclonal antibodies was added to each well for 1 hour at 37° C. After washing, a standard concentration of the biotinylated monoclonal antibody preparation was added for 1 hour at 37° C. The assay was developed by the addition of the avidin substrate as in the ELISA above.

A similar ELISA inhibition was performed with the peanut-positive serum IgE pool instead of the biotinylated monoclonal antibody to determine the ability of each monoclonal antibody to block specific IgE binding.

Results

Hybridomas Specific for Ara h II

Cell fusions between spleen cells obtained from female BALB/c mice immunized with Ara h II and the mouse myeloma cells resulted in a series of hybridomas specific for Ara h II. Seven monoclonal antibody-producing lines were chosen for further study. In preliminary studies all seven hybridoma-secreting cell lines had antibodies that bound Ara h II, as determined by ELISA and immunoblot analysis.[12,13] On the basis of different binding studies, four of the hybridomas were used for further analysis. As determined by isotype immunoglobulin-specific ELISA, all four hybridoma-secreting cell lines typed as $IgG_1$.

ELISA with Monoclonal Antibody as Solid Phase

Four monoclonal antibody preparations (4996D6, 4996C3, 5048B3, and 4996D5) were used as capture antibodies in an ELISA with Ara h Ii as the antigen. Serum from individual patients, who had positive challenge responses to peanut, was used to determine the amount of IgE binding to each peanut fraction captured by the Ara h II-specific monoclonal antibody (Table 1). A reference peanut-positive serum pool was used as the control serum for 100% binding. Seven patients who had positive DBPCFC responses to peanut were chose. All seven patients had significant amounts of anti-peanut-specific IgE to the peanut antigen presented by each of the four monoclonal antibodies compared with the control sera (patient 8 without peanut sensitivity who had elevated serum IgE values, patient 9 without peanut sensitivity who had normal serum IgE values). Titration curves were performed to show that limited amounts of antigen binding were not responsible for similar antibody binding. There were no significant differences in the levels of anti-peanut-specific IgE antibody to the peanut antigens presented by each monoclonal antibody. Most patients had their highest value for IgE binding to the peanut antigen presented by either 4996D6 or 4996C3, whereas no patient had his or her highest percent of IgE binding to the peanut antigen presented by monoclonal antibody 4996D5.

Food Antigen Specificity of Monoclonal Antibodies to Ara h II

To determine whether the Ara h II monoclonal antibodies would bind to only peanut antigen, an ELISA was developed with the pooled peanut-specific IgE from patients who had positive DBPCFC responses to peanut. All four monoclonal antibodies that were fully characterized bound only peanut antigen (Table 2). In the ELISA no binding to soy, lima beans, or-ovalbumin occurred. When the normal serum pool was used in the ELISA, no peanut-specific IgE to either Ara h II or crude peanut could be detected.

In the United States, three varieties of peanuts are commonly consumed: Virginia, Spanish, and Runner. In an ELISA, we attempted to determine whether there were differences in monoclonal antibody binding to the three varieties of peanuts. There was only a minor variation with the ability of the peanut-specific IgE to bind to the captured peanut antigen (data not shown).

Sit Specificity of Four Monoclonal Antibodies

An inhibition ELISA was used to determine the-site specificity of the four monoclonal antibodies to Ara h II (Table 3). As determined by ELISA inhibition analysis, there are at least two different epitopes on Ara h II, which could be recognized by the various monoclonal antibodies (epitope 1-4996C3, epitope 2-4996D6, 5048B3, 4996D5). Seven different monoclonal antibodies generated to Ara h I, a 63.5 kd peanut allergen,[9] were used to inhibit the binding of the four Ara h II monoclonal antibodies to the Ara h Ii protein. None of the Ara h I monoclonal antibodies inhibited any binding of the Ara h II monoclonal antibodies.

Site Specificity of Peanut-specific Human IgE

Results of inhibition assays with monoclonal antibodies to inhibit IgE binding from the IgE pool (from patients with peanut hypersensitivity) to Ara h Ii are shown in Table 4. Monoclonal antibodies 4996C3 and 4996D5 inhibited the peanut-specific IgE up to approximately 25%. Monoclonal antibodies 4996D6 and 5048B3 did not inhibit peanut-specific IgE binding. These two inhibition sites correspond with the two different IgG epitopes recognized by the monoclonal antibodies in the inhibition experiments.

Discussion

The route of allergen administration, dosage, frequency of exposure, and genetic factors all determine the type and severity of an individual's allergic response.[14] To date, no distinct features, which would distinguish allergens as unique antigens, have been identified.[14] In contrast, only three foods in the United States (milk, eggs, and peanuts) account for approximately 80% of positive responses to food challenges in children.[15]

Although clinical sensitivity to most foods is typically lost as a patient ages, clinical sensitivity to peanut is rarely lost. For this reason, it is important to examine the peanut allergens to determine whether they have distinct features that would cause the persistence of clinical reactions.

Two major peanut allergens, Ara h I and Ara h II, have recently been identified and characterized.[8,9] Ara h I has two major bands as determined by sodium dodecylsulfate-polyacrylamide gel electrophoresis with a mean molecular weight of 63.5 kd and an isoelectric point of 4.55. Ara h II has a mean molecular weight of 17 kd and an isoelectric point of 5.2. Individual sequencing of Ara h I and Ara h II indicates that they are probably isoallergens.[8] Other peanut allergens have been identified including peanut 1[16] and concanavalin A-reactive glycoprotein.[17]

In this study four monoclonal antibodies to Ara h II were extensively characterized. All four monoclonal antibodies produced to Ara h II, when used as capture antibodies in an ELISA, presented antigens that bound IgE from patients with positive challenge responses to peanut. No significant differences were detected in the binding of IgE from any one patient to the allergen presented by the individual monoclonal antibodies. In separate ELISA experiments, the four monoclonal antibodies generated to Ara h II did not bind to other legume allergens and did not bind to one variety of peanuts preferentially.

To determine the epitope site specificity of these monoclonal antibodies, inhibition ELISAs were done. At least two different and distinct IgG epitopes could be identified in experiments with the allergen, Ara h II. In related experiments done with pooled serum from patients with positive DBPCFC responses to peanut, two similar IgE epitopes were identified. The results of this study are comparable to those with monoclonal antibodies to Der f I[18] in which five nonoverlapping antigenic sites and three IgE-binding epitopes were identified. In our previous studies with Ara h I monoclonal antibodies,[19] four different antigenic sites were recognized, and three of these sites were IgE-binding epitopes.

In related experiments with other allergens, a variety of solid-phase inhibition assays have been used to block the polyclonal IgE response to the allergen being studied.[6] The interpretation of the level of inhibition that should be regarded as significant has varied from 15% to 80%.[6] The Ara h II monoclonal antibodies inhibited the polyclonal IgE response by up to 25%.

The characterization of these Ara h II monoclonal antibodies will allow future studies to better define the exact amino acid sequence that is responsible for IgE binding. Additionally, these monoclonal antibodies should make purification of the Ara h II allergen much simpler and more efficient. Immunoaffinity purification of allergens, such as that completed with the cockroach allergens[6] and with the Ara h I peanut allergen,[19] has produced a technique to purify allergens from a heterogeneous crude source material.

Future studies on the antigenic and allergenic structure of allergens will likely use monoclonal antibody techniques, in addition to recombinant DNA technology. Monoclonal antibodies will be used to map these epitopes and to identify cDNA clones specific for the allergens. Together, recombinant DNA technology and monoclonal antibody production will be used to examine the role of specific T-cell epitopes in the induction and regulation of the allergenic response.[20]

REFERENCES

1. Yunginger J. W., Jones R T. A review of peanut chemistry: implications for the standardization of peanut extracts. In: Schaeffer M, Sisk C, Brede H I, eds. Proceedings of the Fourth International Paul Ehrlich Seminar on the Regulatory Control and Standardization of Allergenic Extracts, Oct. 16–17, 1985; Bethesda, Md. Stuttgart: Gustav Fischer Verlag, 1987;251–64.
2. Yunginger J W, Sweeney K G, Sturner W Q, et al. Fatal food-induced anaphylaxis. JAMA 1988;260:1450–2.
3. Sampson H A, Mendelson L, Rosen J P. Fatal and near-fatal anaphylactic reactions to food in children and adolescents. N Engl J Med 1992;327:380–4.
4. Hoffman D R, Haddad Z H. Diagnosis of IgE-mediated reaction to food antigens by radioimmunoassay. J ALLERGY CLIN IMMUNOL 1974; 54:165–73.
5. Chapman M D. Purification of allergens. Curr Opin Immunol 1989;1:647–53.
6. Chapman M D. Monoclonal antibodies as structural probes for mite, cat, and cockroach allergens. J Immunol 1987; 139:1479–84.
7. Mourad W, Mecheri S, Peltre G. David B, Hebert J. Study of the epitope structure of purified Dac g I and Lol p I, the major allergens of *Dactylis glomerata* and *Lolium perenne* pollens, using monoclonal antibodies. J Immunol 1988; 141:3486–91.
8. Burks A W, Williams L W, Connaughton C, Cockrell G, O'Brien T J, Helm R M. Identification and characterization of a second major peanut allergen, Ara h II, with use of the sera of patients with atopic dermatitis and positive peanut challenges. J ALLERGY CLIN IMMUNOL 1992;90:962–9.
9. Burks A W, Williams L W, Helm R M, Connaughton C A, Cockrell G, O'Brien T J. Identification of a major peanut allergen, Ara h I, in patients with atopic dermatitis and positive peanut challenges. J ALLERGY CLIN IMMUNOL 1991;88:172–9.
10. Rouse D A, Morris S L, Karpas A B, Probst P G, Chaparas S D. Production, characterization, and species specificity of monoclonal antibodies to *Mycobacterium avium* complex protein antigens. Infect Immun 1990;58:1445–99.
11. Burks A W, Sampson H A, Buckley R H. Anaphylactic reactions following gammaglobulin administration in patients with hypogammaglobulinemia; detection of IgE antibodies to IgA. N Engl J Med 1986;314:560–4.
12. Sutton R, Wrigley C W, Baldo B A. Detection of IgE and IgG binding proteins after electrophoresis transfer from polyacrylamide gels. J Immunol Methods 1982;52:183–6.
13. Towbin H, Staehelin T. Gordan J. Electrophoretic transfer of proteins from polyacrylamide gels to nitrocellulose sheets; procedure and some applications. Proc Natl Acad Sci USA 1979;76:4350–4.
14. Marsh D G. Allergens and the genetics of allergy. In: Sela M. ed. The antigens. New York: Academic Press. 1975;3:271–359.
15. Sampson H A, McCaskill C C. Food hypersensitivity in atopic dermatitis: evaluation of 113 patients. J Pediatr 1985; 107:669–75.
16. Sachs M I, Jones R T, Yunginger J W. Isolation and partial characterization of a major peanut allergen. J ALLERGY CLIN IMMUNOL 1981;67:27–34.
17. Barnett D, Howden, M E H, Bonham B, Burley R W. Aspects of legume allergy research. proc Sydney Allergy Group 1985; 4:104–18.
18. Chapman M D, Heyman P W, Platts-Mills T A E. Epitope mapping of two major inhalant allergens, Der p I and Der f I, from mites of the genus Dermatophagoides. J Immunol 1987;139:1479–84.
19. Burks A W, Cockrell G, Connaughton C, Helm R M. Epitope specificity and immunoaffinity purification of the major peanut allergen, Ara h I. J ALLERGY CLIN IMMUNOL 1994;93:743–50.
20. O'Hehir R E, Young D B, Kay A B, Lamb J R. Cloned human T lymphocytes reactive with *Dermatophagoides farina* (house dust mite): a comparison of T- and B-cell antigen recognition. Immunology 1987;62:635–40.

Isolation, Identification, and Characterization of Clones Encoding Antigens Responsible for Peanut Hypersensitivity Peanut allergy is a significant health problem because of the frequency, the potential severity, and the chronicity of the allergic sensitivity. Peanut hypersensitivity reactions often tend to be quite severe, sometimes resulting in episodes of fatal anaphylaxis [1,2]. Despite the significant prevalence of peanut hypersensitivity reactions and several fatalities annually, the identification of the clinically relevant antigens and an understanding of the immunobiology of peanut hypersensitivity are just beginning [3]. The identification and purification of allergens is essential for the immunological studies necessary to understand their role in stimulating IgE antibody formation. Because of the prevalence and severity of peanut hypersensitivity reactions in both children and adults, coupled with the recent identification of two major peanut allergens that are involved in this process [3,4], we set out to clone and characterize the Ara h I peanut allergen. Serum IgE from patients with documented peanut hypersensitivity reactions and a peanut cDNA expression library were used to identify clones that encode peanut allergens. One of the major peanut allergens, Ara h I, was selected from these clones using Ara h I-specific oligonucleotides and polymerase chain reaction technology. Using the oligonucleotide GA(TC)AA(AG)GA(TC)AA (TC)GTNAT(TCA)GA(TC)CA (SEQ ID NO:5) derived from amino acid sequence analysis of the Ara h I (63.5 kD) peanut allergen as one primer and a 27-nucleotide-long oligo-dT stretch as the second primer, a portion of the mRNA that encodes this protein was amplified from peanut CDNA. To determine if this clone (5ala) represented the entire Ara h I, a $^{22}$P-labeled insert from this clone was used as a hybridization probe of a Northern blot containing peanut poly A+ RNA. This insert hybridized to a single-size mRNA of approximately 2.3 kb. The insert contained 1,360 bases not including the poly A tail. The sequence beginning at position 985 and extending through to position 1032 encodes an amino acid sequence identical to that determined from Ara h I peptide I. DNA sequence analysis of the cloned insert revealed that the Ara h I allergen has significant homology with the vicilin seed storage protein family found in most higher plants [5,6]. There were 64% homology over more than 1,000 bases when the clone 5Ala sequence was compared with the broad bean and pea vicilins. IgE immunoblot analysis was performed using serum IgE from patients with peanut hypersensitivity and Ara h I protein expressed from clone 5Ala in *Escherichia coli* XL1-Blue cells to address the question of how frequently recombinant Ara h I was recognized by these individuals. FIG. 1 shows three representative immunoblot strips that have been incubated with different patient sera. Two of the patients showed strong IgE binding to the recombinant Ara h I protein while one patient had no detectable IgE binding to this protein. of the 11 patient sera tested in this manner, 8 (73%) had IgE which recognized recombinant Ara h I (Table 5). We have demonstrated that the cloned Ara h I gene is capable of producing a protein product in prokaryotic cells that is recognized by serum IgE from a large number of individuals with documented peanut hypersensitivity. These results are significant in that they indicate that some of the allergenic epitopes responsible for this reaction are linear amino acid sequences that do not include a carbohydrate component. These findings may provide the basis for improving diagnosis and therapy of persons with food hypersensitivity. With the production of the recombinant peanut protein it will now be possible to address the pathophysiologic and immunologic mechanisms regarding peanut hypersensitivity reactions specifically and food hypersensitivity in general.

REFERENCES

1. Yunginger J W, Squillace D L, Jones R T, Helm R M: Fatal anaphylactic reactions induced by peanuts. Allergy Proc 1989;10:249–253.

2. Sampson H A, Mendelson L, Rosen J P: Fatal and near-fatal anaphylactic reactions to food in children and adolescents. N Engl J. Med 1992;327:380–384.

3. Burks A W, Williams L W, Helm R M, Connaughton C, Cockrell G, O'Brien T J: Identification of a major peanut Allergen, Ara h I, in patients with atopic dermatitis and positive peanut challenges. J Allergy Clin Immunol 1991;88:172–179.

4. Burks A W, Williams L W, Connaughton C, Cockrell G, O'Brien T. Helm R M: Identification and characterization of a second major peanut allergen, Ara h II, utilizing the sera of patients with atopic dermatitis and positive peanut challenge. J Allergy Clin Immunol 1992;90:962–969.

5. Chee P P, Slightom J L: Molecular biology of legume vicilin-type seed storage protein genes. Subcell Bioch 1991;17:31–52.

6. Dure L: An unstable domain in the vicilin genes of higher plants. N Biol 1990;2:487–493.

TABLE 1

Peanut-specific IgE to antigen presented by four monoclonal antibodies

| Patient No. | Capture antibody | | | |
|---|---|---|---|---|
| | 4996D6 | 4996C3 | 5048B3 | 4996D5 |
| 1 | 95% | 80% | 80% | 91% |
| 2 | 94% | 66% | 72% | 90% |
| 3 | 96% | 114% | 87% | 96% |
| 4 | 98% | 116% | 76% | 96% |
| 5 | 97% | 74% | 130% | 107% |
| 6 | 94% | 63% | 76% | 86% |
| 7 | 109% | 123% | 104% | 116% |
| 8 | 0% | 0% | 0% | 0% |
| 9 | 0% | 0% | 0% | 0% |

Ara h II monoclonal antibodies used as capture antibodies in ELISA with Ara h II as the antigen. Values are expressed as a percent of binding compared with challenge-positive peanut pool. Patients 1 to 7 had positive DBPCFC responses to peanut; patient 8 is the patient without peanut sensitivity with elevated serum IgE; patient 9 is the patient without peanut sensitivity with normal serum IgE.

TABLE 2

IgE-specific binding to legumes captured by Ara h II monoclonal antibodies

| | Capture antibody | | | |
|---|---|---|---|---|
| | 4996D6 | 4996C3 | 5048B3 | 4996D5 |
| Pooled serum* | | | | |
| Ara h II (17 kd) | 0.451 | 0.565 | 0.235 | 0.381 |
| Crude peanut | 0.137 | 0.409 | 0.161 | 0.170 |
| Soy | 0.053 | 0.055 | 0.055 | 0.015 |
| Lima beans | 0.033 | 0.026 | 0.029 | 0.025 |
| Ovalbumin | 0.028 | 0.029 | 0.029 | 0.035 |
| Normal serum | | | | |
| Ara h II (17 kd) | 0.024 | 0.031 | 0.038 | 0.033 |
| Crude peanut | 0.017 | 0.027 | 0.028 | 0.024 |

Values are expressed as optical density units.
*Pooled serum is from patients wiith positive responses to peanut challenge.

TABLE 3

ELISA inhibition for four monoclonal antibodies to Ara h II

| | Inhibitory antibody | | | | |
|---|---|---|---|---|---|
| | 4996C3 | 4996D6 | 5048B3 | 4996D5 | Alt 1 |
| Biotinylated mAb | | | | | |
| 4996C3 | 99% | 8% | 6% | 3% | 1% |
| 4996D6 | 0% | 53% | 31% | 18% | 9% |
| 5048B3 | 30% | 83% | 100% | 100% | 3% |
| 4996D5 | 1% | 44% | 56% | 64% | 8% |

Site specificity of four Ara h II monoclonal antibodies as determined by ELISA inhibition analysis. Values are expressed as percent inhibition.

TABLE 4

Individual anti-peanut-specific IgE binding to Ara h II

| | Serum dilution | | | | | |
|---|---|---|---|---|---|---|
| | 1:320 | 1:100 | 1:80 | 1:40 | 1:20 | 1:5 |
| 4996D6 | 0% | 0% | 0% | 0% | 3% | 5% |
| 4996C3 | 14% | 10% | 10% | 12% | 10% | 24% |
| 5048B3 | 0% | 5% | 5% | 5% | 7% | 11% |
| 4996D5 | 0% | 10% | 10% | 22% | 23% | 25% |

Site specificity of four Ara h II monoclonal antibodies inhibiting anti-peanut-specific IgE (serum pool from patients with peanut hypersensitivity) binding to Ara h II. Values are expressed as percent of anti-peanut-specific IgE binding to Ara h II without inhibiting monoclonal antibody.

TABLE 5

Recognition of Ara h I protein by patient serum IgE from patients with peanut hypersensitivity

| Patient | Recombinant Ara h I | Native Ara h I |
|---|---|---|
| AC | + | + |
| BE | − | + |
| TL | + | + |
| AS | − | + |
| KS | + | + |
| KF | + | + |
| CS | − | + |
| SM | + | + |
| TM | + | + |
| TH | + | + |
| JH | + | + |

Recombinant or native Ara h I protein was electrophoresed on denaturing polyacrylamide gels, blotted to nitrocellulose, and then probed with serum IgE from patients with peanut hypersensitivity. Patients were scored for the presence (+) or absence (−) of serum IgE to recombinant or native Ara h I.

Mapping of the B-cell Epitopes on Ara h I, a Legume Vicilin Protein and a Major Allergen in Peanut Hypersensitivity

SUMMARY

Peanut allergy is a significant health problem because of the potential' severity of the allergic reaction and the difficulty in the accurate diagnosis of this disease. Serum IgE from patients with documented peanut hypersensitivity reactions and overlapping peptides were used to identify the major IgE binding epitopes on the major peanut allergen, Ara h I. At least twenty-three different linear IgE binding epitopes, located throughout the length of the Ara h I protein, were identified. Two of the peptides appeared to be immunodominant IgE binding epitopes in that they were recognized by serum from >90% of the patients tested. No other peptide was recognized by greater than 50% of the peanut sensitive population tested. Mutational analysis of the immunodominant epitopes revealed that single amino acid changes within these peptides had dramatic effects on IgE binding characteristics. With the identification of the IgE binding epitopes on the Ara h I protein and the determination of the amino acids within these epitopes important to immunoglobulin binding it will now be possible to address the pathophysiologic and immunologic mechanisms regarding peanut hypersensitivity reactions specifically and food hypersensitivity in general.

Introduction

Approximately 8% of children and 1–2% of adults have some type of food allergy (1). Peanuts, fish, tree nuts, and shellfish account for the majority of food hypersensitivity reactions in adults, while peanuts, milk, and eggs cause over 80% of food hypersensitivity reactions in children (2). Unlike the food hypersensitivity reactions to milk and eggs, peanut hypersensitivity reactions usually persist into adulthood and last for a lifetime (3). In addition, hypersensitivity reactions to peanuts tend to be more severe than those to other food allergens. Allergic reactions to peanuts can produce symptoms ranging from urticaria to anaphylaxis in patients with peanut hypersensitivity. Several reports (4,5) have detailed fatal and near-fatal anaphylactic reactions occurring in adolescents and adults following the ingestion of peanuts or peanut products. Diagnosis of individuals with peanut hypersensitivity is often complicated by the presence of cross-reacting antibodies to other legumes (6). Currently, the only effective treatment for patients with peanut hypersensitivity is avoidance of any food products which contain the allergen. This is becoming more difficult due to the inclusion of peanuts and peanut products as protein extenders in many different foods.

Food hypersensitivity reactions occur shortly after contact of a specific allergen with its corresponding IgE antibodies which are bound to mast cells. Allergen-specific IgE when cross-linked by the respective allergen activates the mast cells to release histamine, heparin, and other mediators responsible for the clinical symptoms observed. Thus the IgE binding epitopes of the allergens play an important role in the disease process. Their characterization will provide a better understanding of the human immune response involved in food hypersensitivity reactions. If improved diagnostic and therapeutic capabilities are to be developed it is important to determine the primary structure and frequency of recognition of any IgE binding epitopes contained within the allergen.

Various studies have shown that the most allergenic portion of the peanut is the protein fraction of the cotyledon (7). A major allergen found in the cotyledon is the peanut protein, Ara h I (8). This protein is recognized by >90% of peanut sensitive patients, thus establishing it as an important allergen (8). The majority of serum IgE recognition of the Ara h I allergen appears to be due to epitopes within this protein that are linear amino acid sequences that do not contain significant amounts of carbohydrate (8,9). The Ara h I allergen belongs to the vicilin family of seed storage proteins (9). Previous results have demonstrated similarity between the level of IgE binding to recombinant Ara h I protein and the native form of this allergen when individual patient serum was tested (9). These results indicated that the recombinant protein could be considered for use in both diagnostic and immunotherapeutic approaches to peanut hypersensitivity.

Because of the prevalence and severity of peanut hypersensitivity reactions in both children and adults, coupled with the difficult nature of diagnosing this food allergy, we set out to map and characterize the major IgE epitopes of the Ara h I allergen. In this communication we report the primary structure of the Ara h I IgE-binding epitopes recognized by peanut hypersensitive individuals. Two epitopes that bound peanut specific serum IgE from >90% of patients tested were identified. The amino acids important to peanut-specific IgE recognition of these epitopes were then determined for the purpose of using them in future diagnostic and immunotherapeutic approaches to this disease.

Materials and Methods

Patients. Serum from fifteen patients with documented peanut hypersensitivity reactions(mean age, 25 yr) was used to identify the Ara h I IgE binding epitopes. Each of these individuals had a positive immediate prick skin test to peanut and either a positive double blind, placebo controlled, food challenge (DBPCFC) or a convincing history of peanut anaphylaxis (laryngeal edema, severe wheezing, and/or hypotension). One individual with elevated serum IgE levels (who did not have peanut specific IgE or peanut hypersensitivity) was used as a control in these studies. In some instances a serum pool was made by mixing equal aliquots of serum IgE from each of the 15 patients with peanut hypersensitivity. This pool was then used in immunoblot analysis experiments to determine the IgE binding characteristics of the population. At least five mls of venous blood were drawn from each patient and allowed to clot, and the serum collected. All studies were approved by the Human Use Advisory Committee at the University of Arkansas for Medical Sciences.

Computer analysis of Ara h I sequence. Sequence analysis of the Ara h I gene (9) and peptide sequences was done on the University of Arkansas for Medical Science's Vax computer using the Wisconsin DNA analysis software package. The predicted antigenic regions on the Ara h I protein are based on algorithms developed by Jameson and Wolf (10) that relates antigenicity to hydrophilicity, secondary structure, flexibility, and surface probability.

Peptide synthesis. Individual peptides were synthesized on a cellulose membrane containing free hydroxyl groups using Fmoc-amino acids according to the manufacturer's instructions (Genosys Biotechnologies, The Woodlands, Tex.). Synthesis of each peptide was started by esterification of an Fmoc-amino acid to the cellulose membrane. After washing, all residual amino functions on the sheet were blocked by acetylation to render it unreactive during the subsequent steps. Each additional Fmoc-amino acid is esterified to the previous one by this same process. After addition of the last amino acid in the peptide, the amino acid side chains were de-protected using a mixture of dichloromethane/trifluoroacetic acid/triisobutylsilane (1/1/0.05), followed by treatment with dichloromethane and washing with methanol. Membranes containing synthesized peptides were either probed immediately with serum IgE or stored at −20° C. until needed.

IgE binding assay. Cellulose membranes containing synthesized peptides were incubated with the serum pool or individual serum from patients with peanut hypersensitivity diluted (1:5) in a solution containing TBS and 1% bovine serum albumin for at least 12 h at 4° C. or 2 h at room temperature. Detection of the primary antibody was with $^{125}$I-labeled anti-IgE antibody (Sanofi Pasteur Diagnostics, Chaska, Minn.).

Results

There are Multiple IgE Binding Regions Throughout the Ara h I Protein. The Ara h I protein sequence was analyzed using a computer program to model secondary structure and predict antigenicity based on the parameters of hydrophilicity, secondary structure, flexibility, and surface probability. Eleven antigenic regions, each containing multiple antigenic sites, were predicted by this analysis along the entire length of the molecule (FIG. 1).

Figures 2A, 2B:
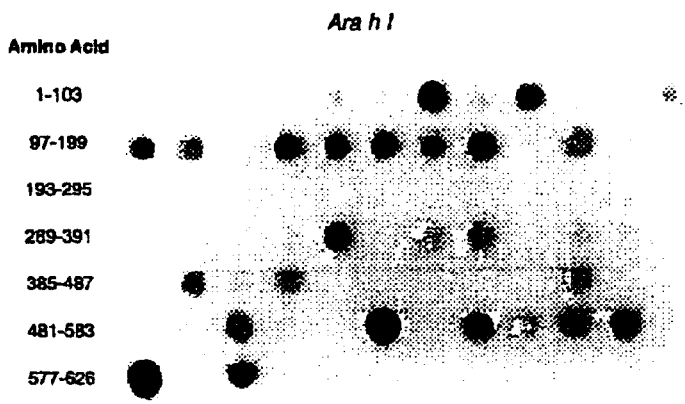

Seventy-seven overlapping peptides representing the entire length of the Ara h I protein were synthesized and probed with pooled serum to determine IgE binding to the predicted antigenic regions, or any other regions of the protein. Each peptide was 15 amino acids long and offset from the previous peptide by eight amino acids. These peptides were then probed with a pool of serum IgE from 15 patients with documented peanut hypersensitivity or with serum IgE from a control patient with no food allergy. FIG. 2A shows 12 IgE binding regions along the entire length of the Ara h I protein recognized by this population of peanut hypersensitive patients. Serum IgE from the control patient did not recognize any of the synthesized peptides (data not shown). In general, there was good agreement between the predicted antigenic regions (FIG. 2B, boxed areas P1–P11) and those that were determined (FIG. 2B shaded areas D1–D12) by actual IgE binding. However, there were two predicted antigenic regions (AA221–230; AA263–278) that were not recognized by serum IgE from peanut hypersensitive individuals. In addition, there were numerous IgE binding regions found in the Ara h I protein between amino acids 450–600 (FIG. 2A).

Figure 3:
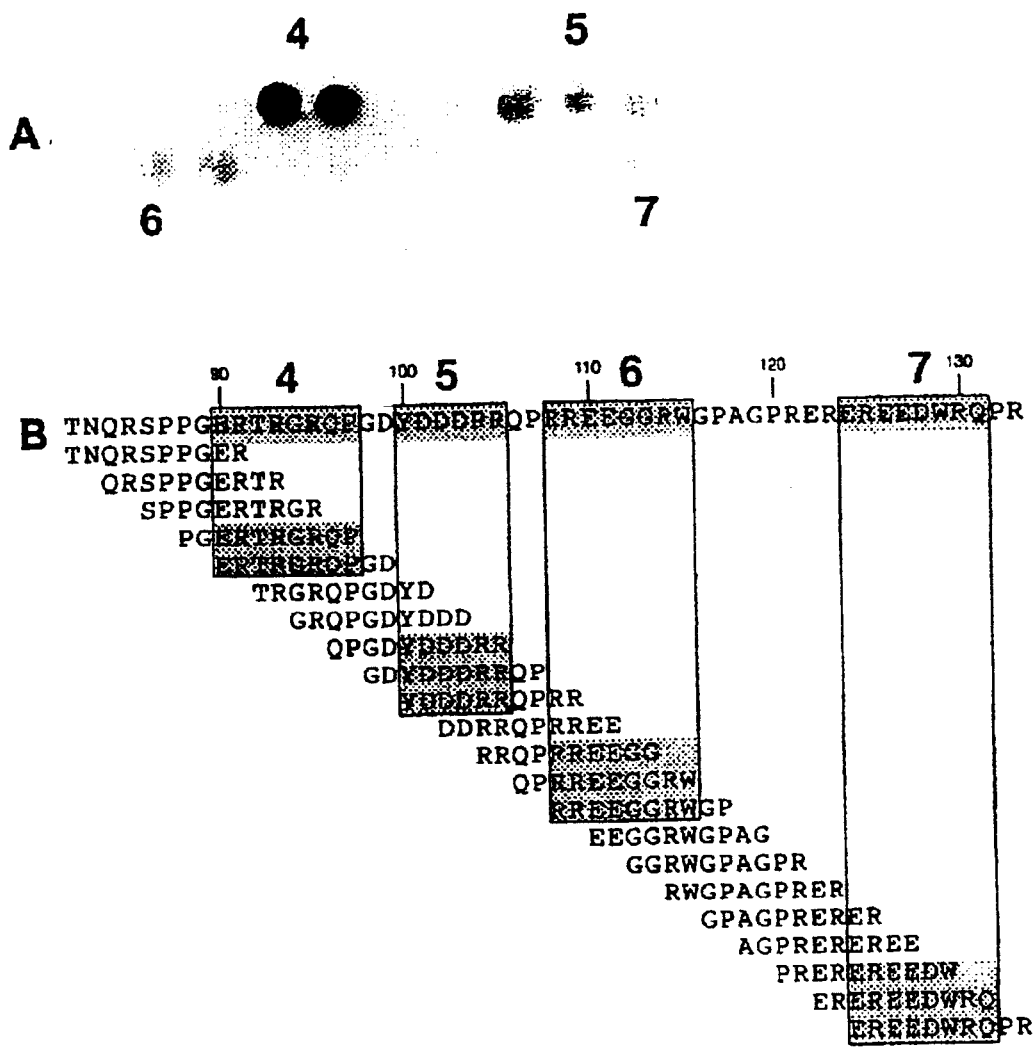

In order to determine the amino acid sequence of the IgE binding sites, small overlapping peptides spanning each of the larger IgE binding regions identified in FIG. 2 were synthesized. By synthesizing smaller peptides (10 amino acids long) that were offset from each other by only two amino acids it was possible to identify individual IgE binding epitopes within the larger IgE binding regions of the Ara h I molecule. FIG. 3 shows a representative immunoblot and the respective amino acid sequence of the binding region D2–D3 (AA82–133). Four epitopes (FIG. 3 numbers 4–7) were identified in this region. Similar blots were performed for the remaining IgE binding regions to identify the core amino acid sequences for each IgE epitope. Table 6 summarizes the 23 IgE epitopes-(peptides 1–23) and their respective positions in the Ara h I molecule. The most common amino acids found were acidic (D,E) and basic (K,R) residues comprising 40% of all amino acids found in the epitopes. In addition, no obvious amino acid sequence motif was shared by the epitopes.

Identification of Common Ara h I Epitopes Recognized by Serum IgE from Patients With Peanut Hypersensitivity.

Figure 4:
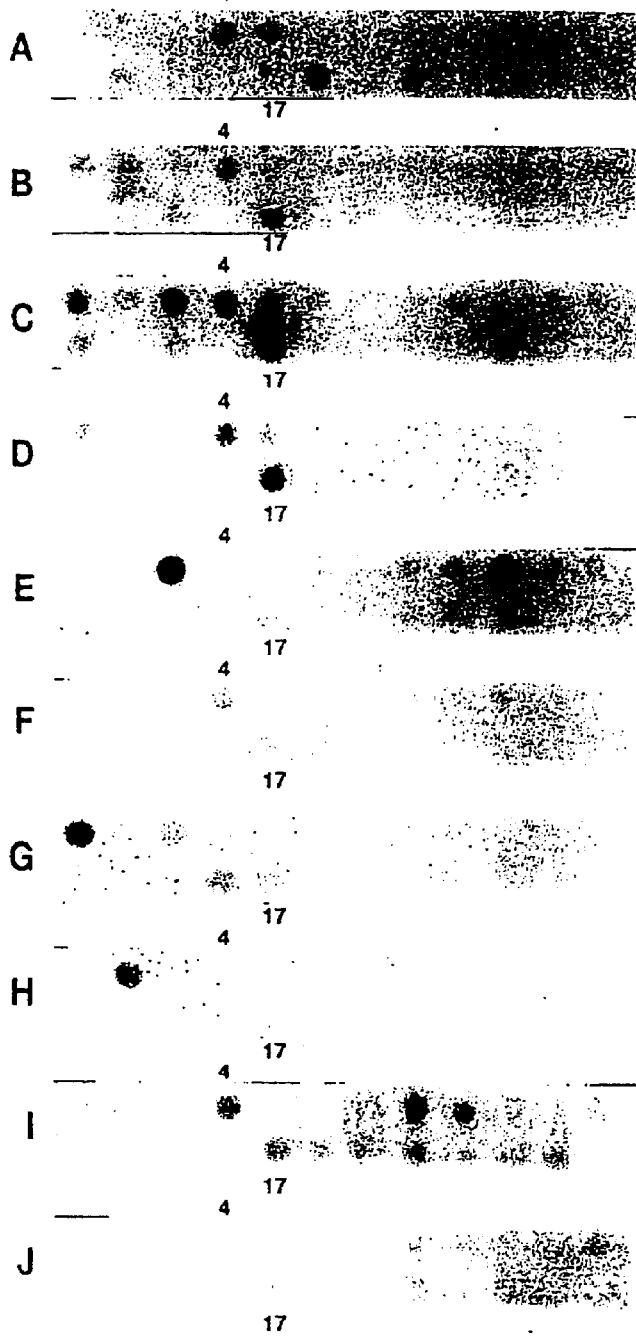

Each set of twenty-three peptides was probed with serum IgE from 10 individuals to determine which of the twenty-three epitopes were recognized by serum IgE from patients with peanut hypersensitivity. Serum from five individuals randomly selected from the 15 patient serum pool and an additional five sera from peanut hypersensitive patients not represented in the serum pool were used to identify the common epitopes. FIG. 4 shows the IgE binding results of the 10 immunoblot strips (A–J) containing these peptides incubated with individual patient sera. All of the patient sera tested (10/10) recognized multiple epitopes. The average number of epitopes recognized was 6/patient sera, ranging from one serum recognizing only 2 epitopes to another patient's serum recognizing 12 epitopes. The results are summarized in Table 7. Interestingly, epitope 17 was recognized by all patient sera tested (10/10) and epitope 4 was recognized by 90% (9/10) of patient sera tested. No other epitope was recognized by more than 50% of the patient sera tested.

Figure 5:
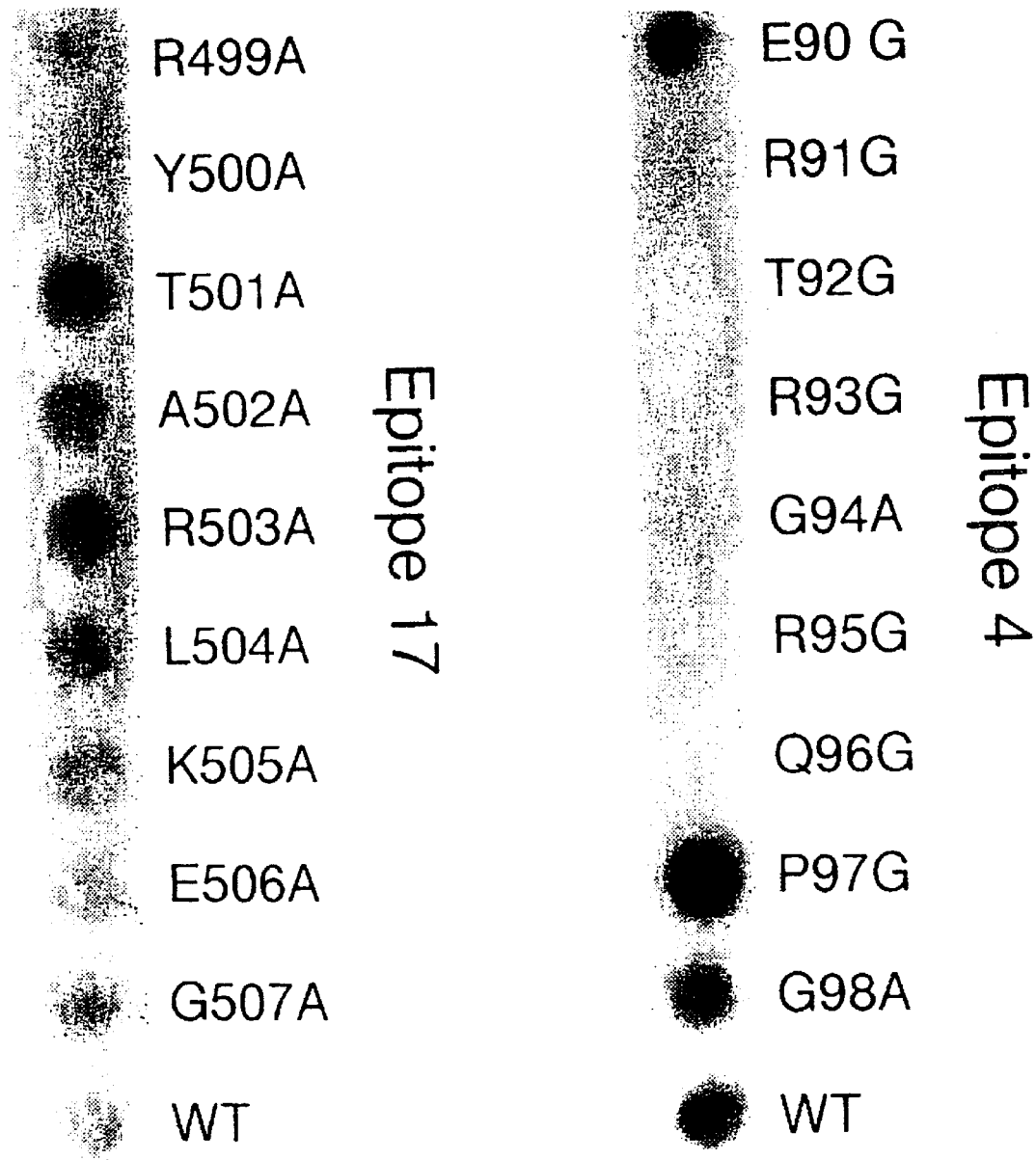

IgE binding Characteristics of Mutated Ara h I Epitopes. The amino acids essential to IgE binding in epitopes 4 and 17 were determined by synthesizing duplicate peptides with single amino acid changes at each position. The amino acids were changed to either an alanine or glycine residue because these amino acids have small, R groups. These peptides were then probed with pooled serum IgE from 15 patients with peanut hypersensitivity to determine if the change affected peanut-specific IgE binding. The results are shown in FIG. 5. Clearly, a single amino acid substitution has dramatic effects on the IgE binding characteristics of that peptide. Replacement of any amino acid in the 91–96 region of epitope 4 resulted in almost complete loss of IgE binding to this epitope. In epitope 17, replacement of the tyrosine residue at position 500 or replacement of the glutamic acid residue at position 506 also resulted in dramatic decreases in IgE binding.

Significant sequence homology between epitopes 4 and 17 and seed storage proteins from other plants could explain the presence of cross-reacting antibodies to other legumes which complicates diagnosis. To assess the prevalence of the amino acid sequences of epitope 4 and 17 in other seed storage proteins, the complete Ara h 1 amino acid sequence was first used to select all plant proteins that shared sequence homology with the peanut vicilin. There were 93 entries selected on this basis, representing amino acid sequences deposited in the protein data base from a variety of seed storage proteins. The amino acid sequence for epitope 17 was present in many of these proteins with sequence identity ranging from 20–60%. Interestingly, even in those proteins with only 20% identity the tyrosine at position 500 and the glutamic acid residue at position 506 were almost always conserved (Table 8). The amino acid sequence for epitope 4 was present in fewer of these proteins with sequence identity ranging from 20–30%. In every case, at least one of the amino acids at positions 91–96 were different from the peanut vicilin (Table 8).

Discussion

The development of an IgE response to an allergen involves a series of interactions between T cells and B cells. B cells bearing appropriate antigen-specific receptors interact with proliferating allergen specific T-cells which leads to isotype switching and the generation of antigen-specific IgE. The antigen-specific IgE then binds to surface receptors of mast cells, basophils, macrophages, and other APCs enabling the immune system to respond to the next encounter with the specific antigen (B-cell epitope). Because antigen specific IgE plays such a critical role in the etiology of allergic disease, determination of allergen-specific, IgE binding epitopes is an important first step toward a better understanding of this complex disease process.

The vicilins are seed storage proteins found in most higher plants (11). A comparison of the vicilin amino acid sequences from different plant sources reveals that considerable sequence homology exists between the carboxyl two-thirds of all these molecules. The major difference between the vicilins is found in the amino terminal end of these proteins where little sequence homology is detected (11). In sequence comparison studies (9) with other legumes, the peanut vicilin, Ara h I conforms to this general rule with the highest similarity being found in the carboxyl two-thirds of this molecule.

In the present study we have determined that there were multiple antigenic sites predicted for the Ara h I allergen. In general, as has been found with other allergens (12,13), there was good agreement between those residues predicted by computer analysis and B-cell epitopes determined by-experimental analysis of overlapping peptides. This strong correlation between predicted and determined epitopes is probably due to the ability of the computer model to predict which regions of the molecule are exposed on the surface of the allergen, making them accessible to immunoglobulin interactions. There are at least 23 different IgE recognition sites on the major peanut allergen Ara h I. These sites are distributed throughout the protein. The identification of multiple epitopes on a single allergen is not novel. Allergens from cow milk (14), codfish (15), hazel, (16), soy (17) and shrimp (18) have all been shown to contain multiple IgE binding epitopes. The observation that most of these proteins have multiple IgE binding sites probably reflects the polyclonal nature of the immune response to them and may be a necessary step in establishing a protein as an allergen.

The elucidation of the major IgE binding epitopes on Ara h I may also enable us to better understand the immuno-pathogenic mechanisms involved in peanut hypersensitivity. Recent evidence suggests that there is a preferential variable heavy chain usage in IgE synthesis and a direct switching from IgM production to IgE synthesis (19). This would suggest that epitopes responsible for antigen-specific IgE antibody production may differ from those promoting antigen-specific IgG antibodies. Immunotherapeutic approaches utilizing peptides representing IgG epitopes may be able to shift the balance of antigen-specific antibody production from IgE to IgG. We are currently identifying which of the IgE binding epitopes also bind IgG to determine if this would be a feasible strategy for patients with peanut hypersensitivity.

Two of the Ara h I peptides appear to be immunodominant IgE binding epitopes in that they are recognized by >90% of patient sera tested. Interestingly, epitope 17 which is located in the carboxyl end of the protein (AA 498–507), is in a region that shares significant sequence homology with vicilins from other legumes. The amino acids important to IgE binding also appear to be conserved in this region and may explain the possible cross-reacting antibodies to other legumes that can be found in sera of patients with a positive DBPCFC to peanuts. Epitope 4, located in the amino terminal portion (AA 89–98) of the protein, appears to be unique to this peanut vicilin and does not share any significant sequence homology with vicilins from other legumes. In addition, the amino acids important to IgE binding in this region are not conserved. These findings may enable us to develop more sensitive and specific diagnostic tools and lead to the design of novel therapeutic agents to modify the allergic response to peanuts.

The only therapeutic option presently available for the prevention of a food hypersensitivity reaction is food avoidance. Unfortunately, for a ubiquitous food such as peanut, the possibility of an inadvertent ingestion is great. One therapeutic option used extensively for patients with allergic reactions to various aeroallergens and insect sting venoms is allergen desensitization immunotherapy. Allergen immunotherapy consists of injections of increasing amounts of allergens to which a patient has Type I immediate hypersensitivity (20,21). Allergens for immunotherapy are usually extracted from natural sources and represent mixtures of several different proteins, to many of which the patient is not allergic. These non-allergenic components could induce an IgE-response in hyposensitized patients (22) thus complicating their use as a therapeutic tool. One of the major improvements in allergen immunotherapy has been the use of standardized allergenic extracts which has been made possible by the use of recombinant allergens (23,24). While the absolute mechanism of immunotherapy is unknown, an increase in IgG or IgG4 antibody activity, a decrease in allergen-specific IgE levels, and a decrease in basophil activity have all been implicated (25–28) in mediating this response. Because allergen immunotherapy has been proven efficacious for treatment of some allergies, treatment with peanut immunotherapy is now being studied as a possible option (29). Our work showing the IgE binding epitopes of a major peanut allergen may allow for the use of immunodominant epitopes in this approach. One possible advantage of using peptides over using the whole allergen is the reduced danger of anaphylaxis. The degranulation of mast cells requires the cross-linking of IgE antibodies bound to the high affinity FceR I receptors (30). Peptides containing single IgE epitopes would be unable to bind to more than one IgE antibody and therefore unable to cross-link the bound IgE. We are currently exploring this possibility in in-vitro and in vivo models.

REFERENCES

1. Jansen J. J., A. F. M. Kardinaal, G. Huijber, B. J. Vleig-Boerstra, B. P. Martens, and T. Ockhuizen. 1994. Prevalence of food allergy and intolerance in the adult Dutch population. J. Allergy Clin. Immunol. 93:446–456.
2. Sampson H. A. 1988. The role of food allergy and mediator release in atopic dermatitis. J. Allergy Clin. Immunol. 81:635–645.
3. Bock S. A., and F. M. Atkins. 1989. The natural history of peanut allergy. J. Allergy Clin. Immunol. 83:900–904.
4. Sampson H. A., I. Mendelson, and J. P. Rosen. 1992. Fatal and near-fatal anaphylactic reactions to food in children and adolescents. N. Engl. J. Med. 327:380–384.
5. Yunginger, J. W., K. G. Sweeney, W. Q. Sturner, L. A. Giannandrea, J. D. Teigland, M. Bray, P. A. Benson, J. A. York, L. Biedrzycki, D. L. Squillace, et al. 1988. Fatal food-induced anaphylaxis. JAMA, 260:1450–1452.
6. Bernhisel-Broadbent, J., S. Taylor, and H. A. Sampson. 1989. Cross-allergenicity in the legume botanical family in children with food hypersensitivity. II. Laboratory correlates J. Allergy Clin. Immunol. 84:701–709.
7. Taylor, S. L., W. W. Busse, M. I. Sachs, J. L. Parker, and J. W. Yunginger. 1981. Peanut oil is not allergenic to peanut sensitive individuals. J. Allergy Clin. Immunol. 68:372–375.
8. Burks A. W., L. W. Williams, R. M. Helm, C. Connaughton, G. Cockrell, T. O'Brien. 1991. Identification of a major peanut allergen Ara h I, in patients with atopic dermatitis and positive peanut challenge. J. Allergy Clin. Immunol. 88:172–179.
9. Burks A. W., G. Cockrell, J. S. Stanley, R. M. Helm, G. A. Bannon. 1995. Recombinant peanut allergen Ara h I expression and IgE binding in patients with peanut hypersensitivity. J. Clin. Invest. 96:1715–1721.
10. Jameson, B. A, and H. Wolf. 1988. The antigenic index: a novel algorithm for predicting antigenic determinants. Comput. Appl. Biosci. 4:181–186.
11. Gibbs, P. E., K. B. Strongin, and A. McPherson. 1989. Evolution of legume seed storage proteins—a domain common to legumins and vicilins is duplicated in vicilins. Mol. Biol. Evol. 6:614–623.
12. Van Kampen, V., W. M. Becker, Z. Chen, H. P. Rihs, G. Mazur, M. Raulf, V. Liebers, S. Isringhausen-Bley, and X. Baur. 1994. Analysis of B-cell epitopes in the N-terminal region of Chi t I component III using monoclonal antibodies. Molecular Immunol., 31:1133–1140.
13. Breiteneder, H., F. Ferreira, A. Reikerstorfer, M. Duchene, R. Valenta, K. Hoffman-Sommergruber, C. Ebner, M. Breitenbach, D. Kraft, O. Scheiner. 1992. Complementary DNA cloning and expression in *Escherichia coli* of Aln g I, the major allergen in pollen of alder (Alnus glutinosa). J. Allergy Clin. Immunol., 90:909–917.
14. Ball G., M. J. Shelton, B. J. Walsh, D. J. Hill, C. S. Hosking, and M. E. Howden. 1994. A major continuous allergenic epitope of bovine bata-lactoglobulin recognized by human IgE binding. Clinical and Experimental Allergy. 24:758–764.
15. Aas, K. and S. Elsayed. 1975. Physico-chemical properties and specific activity of a purified allergen (codfish). Developments in Biological Standardization. 29:90–98.
16. Elsayed, S., E. Holen, and T. Dybendal. 1989. Synthetic allergenic epitopes from the amino-terminal regions of the major allergens of hazel and birch pollen. Int'l. Archives of Allergy & Applied Immunology, 89:410–415.
17. Herian, A. M., S. L. Taylor, and R. K. Bush. 1990. Identification of soybean allergens by immunoblotting with sera from soy-allergic adults. Int. Arch. Allergy Appl. Immunol., 92:193–198.
18. Shanti, K. N., B. M. Martin, S. Nagpal, D. D. Metcalf, and P. V. Rao. 1993. Identification of tropomyosin as the major shrimp allergen and characterization of its IgE-binding epitopes. J. of Immunology. 151:5354–5363.
19. Van der Stoep, N., W. Korver, and T. Logtenberg. 1994. In vivo and in vitro IgE isotype switching in human B lymphocytes: evidence for a predominantly direct IgM to IgE class switch program. European J. of Immunol., 24:1307–1311.
20. Reisman, R. E. 1994. Fifteen years of hymenoptera venom immunotherapy: changing concepts and lessons. Allergy Proceedings, 15:61–63.
21. Fitzsimons, T., and L. C. Grammer. 1990. Immunotherapy-definition and mechanism. Allergy Proc., 11:156.

22. Birkner, T., H. Rumpold, E. Jarolim, H. Ebner, M. Breitenbach, O. Scheiner, and D. Kraft. Evaluation of immunotherapy-induced changes in specific IgE, IgG, and IgG-subclasses in birch pollen-allergic patients by means of immunoblotting. Correlation with clinical response. Allergy, 45:418–426.
23. Scheiner, O. 1992. Recombinant allergens: biological, immunological and practical aspects. Int Arch Allergy Immunol., 98:93–96.
24. Gordon, B. R., 1995. Future immunotherapy: what lies ahead? Otolaryngol Head Neck Surg., 113:603–605.
25. Sparholt, S. H., O. T. Olsen, and C. Schou. 1992. The allergen specific B-cell response during immunotherapy. Clinical and Experimental Allergy, 22:648–653.
26. Gieni, R. S., X. Yang, and K. T. Hayglass. 1993. Allergen-specific modulation of cytokine synthesis patterns and IgE responses in vivo with chemically modified allergen. The Journal of Immunol., 150:302–310.
27. Secrist, H., C. J. Chelen, Y. Wen, J. D. Marshall, and D. T. Umetsu. 1993. Allergen immunotherapy decreases interleukin 4 production in CD4+ T cells from allergic individuals. J. Exp. Med., 178:2123–2130.
28. Garcia, N. M., N. R. Lynch, M. C. Di Prisco, and R. I. Lopez. 1995. Nonspecific changes in immunotherapy with house dust extract. J Invest. Allergol. Clin. Immunol., 5:18–24.
29. Oppenheimer, J. J., H. S. Nelson, S. A. Bock, F. Christensen, and D. Y. Leung. 1992. Treatment of peanut allergy with rush immunotherapy. J. Allergy Clin. Immunol., 90:151–152.
30. Fung-Leung, W. P., J. DeSousa-Hitzler, A. Ishaque, L. Zhou, J. Pang, K. Ngo, J. A. Panakos, E. Chourmouzis, F. T. Liu, and C. Y. Lau. 1996. Transgenic mice expressing the human high-affinity immunoglobulin (Ig) E receptor alpha chain respond to human IgE in mast cell degranulation and in allergic reactions. J. of Exp. Med., 183:49–56.

Acknowledgements

This work was supported in part by grants from the National Institute of Health (AI33596) and the Clarissa Sosin Research Foundation.

FIGURE LEGENDS

FIG. 1. There Are Multiple Predicted Antigenic Sites on the Ara h I Allergen. The amino acid sequence of the Ara h I protein was analyzed for potential antigenic sites by the Jameson and Wolf (1988) algorithm. These predictions are based on a model that relates antigenicity to hydrophilicity, secondary structure, flexibility, and surface probability. There were 11 (1–11) predicted regions that contained multiple antigenic sites (octagons) along the entire length of the molecule. Amino acid residues (small numbers) are represented as alpha-helical (sinusoidal curve), Beta-sheet (saw tooth curve), and coil (flat sinusoidal curve) conformations. Beta turns are denoted by chain reversals.

FIGS. 2A and 2B Multiple IgE Binding Regions Identified on the Ara h I Allergen. FIG. 2A Upper Panel: Epitope mapping was performed on the Ara h I allergen by synthesizing the entire protein in 15 If amino acid long overlapping peptides that were offset from each other by 8 amino acids. These peptides were then probed with a pool of serum IgE from 15 patients with documented peanut hypersensitivity. The position of the peptides within the Ara h I protein are indicated on the left hand side of this panel. FIG. 2B (SEQ ID NO:4). Lower Panel: The amino acid sequence of the Ara h I protein is shown in the lower panel. The numbered boxes correspond to the predicted antigenic regions (P1–P11). The hatched boxes (D1–D12) correspond to the IgE binding regions shown in FIG. 2A.

FIG. 3. Core IgE Binding Epitopes Identified on the Ara h I Allergen. Panel A: Detailed epitope mapping was performed on IgE binding regions identified in FIG. 2 by synthesizing 10 amino acid long peptides offset from each other by two amino acids. These peptides were then probed with a pool of serum IgE from 15 patients with documented peanut hypersensitivity. The data shown represents regions D2 and a portion of D3 encompassing amino acid residues 82–133. Numbers correspond to peptides as shown in Table 6. Panel B: The amino acid sequence (residues 82–133) of Ara h I (SEQ ID NO:4) that was tested in Panel A is shown. Shaded areas of boxes correspond to IgE binding peptides in Panel A.

FIG. 4. Commonly Recognized Ara h I Epitopes. Core IgE binding epitopes were synthesized (10 amino acids long) and then probed individually with serum IgE from 10 patients with documented peanut hypersensitivity. The top panel represents where each of the Ara h I peptides (1–23) were placed on the membrane. Panels A–J show the peptides that bound serum IgE from patients with peanut hypersensitivity. The control panel was probed with sera from a patient with elevated IgE but who does not have peanut hypersensitivity.

FIG. 5. Amino Acids Involved in IgE Binding. Epitope 4 and 17 were synthesized with a glycine (G) or alanine (A) substituted for one of the amino acids in each of these peptides and then probed with a pool of serum IgE from 15 patients with documented peanut hypersensitivity. The letters across the top of each panel indicate the one letter amino acid code for the residue normally at that position and the amino acid that was substituted for it. The numbers indicate the position of each residue in the Ara h I protein.

TABLE 6

Ara b I IgE binding epitopes (SEQ ID NO:4).

| PEPTIDE | AA SEQUENCE | Ara h I POSITION |
|---|---|---|
| 1 | AKSSPYQKKT | 25–34 |
| 2 | QEPDDLKQKA | 48–57 |
| 3 | LEYDPRLVYD | 65–74 |
| 4 | GERTRGRQPG | 89–98 |
| 5 | PGDYDDDRRQ | 97–106 |
| 6 | PRREEGGRWG | 107–116 |
| 7 | REREEDWRQP | 123–132 |
| 8 | EDWRRPSHQQ | 134–143 |
| 9 | QPRKIRPEGR | 143–152 |
| 10 | TPGQFEDFFP | 294–303 |
| 11 | SYLQEFSRNT | 311–320 |
| 12 | FNAEFNEIRR | 325–334 |
| 13 | EQEERGQRRW | 344–353 |
| 14 | DITNPINLRE | 393–402 |
| 15 | NNFGKLFEVK | 409–418 |
| 16 | GTGNLELVAV | 461–470 |
| 17 | RRYTARLKEG | 498–507 |
| 18 | ELHLLGFGIN | 525–534 |
| 19 | HRIFLAGDKD | 539–548 |
| 20 | IDQIEKQAKD | 551–560 |
| 21 | KDLAFPGSGE | 559–568 |

TABLE 6-continued

Ara b I IgE binding epitopes (SEQ ID NO:4).

| PEPTIDE | AA SEQUENCE | Ara h I POSITION |
|---|---|---|
| 22 | KESHFVSARP | 578–587 |
| 23 | PEKESPEKED | 597–606 |

The underlined portions of each peptide are the smallest IgE binding sequences as determined by the analysis as described in FIG. 3.

TABLE 7

IgE binding of core Ara h I epitopes by serum from peanut hypersensitive individuals.

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | Epitopes/Patient |
|---|---|---|---|---|---|---|---|---|---|---|---|---|---|---|---|---|---|---|---|---|---|---|---|---|
| A |   |   |   | X | X |   |   |   |   |   |   |   |   | X |   |   | X | X |   | X |   |   |   | 6 |
| B | X | X |   | X | X |   |   |   |   |   |   |   |   |   | X |   | X |   |   |   |   |   |   | 6 |
| C | X | X | X | X | X | X |   | X |   |   | X | X |   | X |   |   | X |   |   |   |   | X |   | 12 |
| D | X |   |   | X | X | X |   |   |   |   |   |   | X |   | X |   | X |   |   |   |   |   |   | 6 |
| E |   |   | X | X |   |   |   | X | X | X | X |   |   |   |   |   | X |   |   | X | X | X |   | 11 |
| F |   | X |   | X |   |   |   |   | X |   |   |   |   |   |   |   | X |   |   |   |   |   |   | 4 |
| G | X | X | X |   |   |   |   |   |   |   |   |   | X |   |   | X | X |   |   |   |   |   |   | 6 |
| H |   | X |   | X |   |   |   |   |   |   |   |   |   |   |   |   | X |   |   |   |   |   |   | 3 |
| I |   | X |   |   |   |   |   | X | X |   |   |   |   |   |   |   | X | X | X | X |   |   | X | 8 |
| J |   | X |   |   |   |   |   | X | X |   | X |   |   |   |   |   | X |   | X |   | X |   |   | 7 |
|   | 4 | 5 | 3 | 9 | 4 | 1 | 0 | 3 | 4 | 2 | 1 | 3 | 3 | 1 | 3 | 1 | 10 | 2 | 1 | 4 | 1 | 3 | 1 | Pts/epitope |

Patients are indicated by letters (A–J) on the left hand side of the table. Ara h I peptides are indicated by number (1–23) across the top of the table. The number of epitopes recognized by each patient (epitopes/patient) is shown on the right hand side of the table. The number of patients that recognized each epitope (pts/epitope) is shown across the bottom of the table. An X indicates that a peptide bound IgE.

TABLE 8

Amino acid comparison of Ara h I epitopes 4 and 17 with similar regions in other seed storage proteins.

|   | EPITOPE 4 |   | EPITOPE 4 |
|---|---|---|---|
| Ara h 1 | GERTRGRQPG (amino acids 89–93 of SEQ ID NO:4) | Ara h I | RRYTARLKEG (amino acids 498–507 of SEQ ID NO:4) |
| Soy | FPRPQRQEE (SEQ ID NO:6) | Soy | RKYRAELSEQ (SEQ ID NO:7) |
| Cacao | -EQCEQRCER (SEQ ID NO:8) | Jack bean | RRYAATLSEG (SEQ ID NO:9) |
| Pea | EEHEEEKQKY (SEQ ID NO:10) | Pea | QRYEARLADG (SEQ ID NO:11) |
| Maize | WEDDNHHHH (SEQ ID NO:12) | Fava bean | QNYKAKLSPG (SEQ ID NO:13) |

The peptides representing Ara h I epitopes 4 and 17 were compared with similar regions from other seed storage proteins. The amino acids residues important to IgE binding are indicated as bold underlined letters. Those amino acids that are identical to the Ara h I sequence are underlined.

The Major Peanut Allergen Ara h 2 is a Seed Storage Protein with Multiple IgE-binding Epitopes Introduction Immediate hypersensitivity reactions to foods occur in about 4% of children and 1% of adults and are mediated by the production of IgE antibodies to glycoproteins of very high abundance present in the food. Peanuts are a major cause of serious allergic reactions in both children and adults. The hypersensitivity to peanuts often starts in childhood and continues throughout life. This is in contrast to other childhood food allergies such as to milk and eggs which generally resolve spontaneously with age. In addition, peanut allergy is more likely to cause fatal anaphylaxis than any other food allergy. Currently, avoidance is the only effective means of dealing with food allergy, but the use of peanuts and peanut by-products as supplements in many different foods makes accidental consumption almost inevitable. Thus, the prevalence and chronic nature of peanut allergy, the potential severity of the allergic reaction, and the widespread use of peanuts in consumer foods necessitates improved methods for managing peanut hypersensitivity.

Food hypersensitivity reactions occur shortly after contact of a specific allergen with its corresponding IgE antibodies which are bound to mast cells. Cross-linking of the allergen-specific IgE by the respective allergen activates the mast cells to release histamine, heparin, and other mediators responsible for the clinical symptoms observed. Thus, the IgE binding epitopes of the allergens play an important role in the disease process. Their characterization will provide a better understanding of the human immune response involved in food hypersensitivity reactions. If improved diagnostic and therapeutic capabilities are to be developed it is important to determine the primary structure of the major allergens, the IgE binding sites of these allergens, and the frequency of recognition of any IgE binding epitopes that are identified.

Various studies have shown that the most allergenic portion of the peanut is the protein fraction of the cotyledon. Two highly abundant glycoproteins found in the cotyledon are the peanut allergens, Ara h 1 and Ara h 2. These proteins are recognized by serum IgE from >90% of peanut sensitive patients, thus establishing them as important allergens. The majority of serum IgE recognition of the Ara h 1 and Ara h 2 allergens appear to be due to epitopes within these proteins that are linear amino acid sequences that do not contain significant amounts of carbohydrate. The gene encoding the Ara h 1 allergen has been cloned, sequenced, and identified as a seed storage protein belonging to the vicilin family of legume storage proteins.

The major peanut allergen, Ara h 2, has now been cloned and the nucleotide sequence determined. The derived amino acid sequence has been used to construct synthetic peptides and perform a detailed examination of the linear IgE binding epitopes of this protein.

Experimental Procedures

Patients. Serum from 15 patients with documented peanut hypersensitivity (mean age, 25 yr) was used to identify peanut allergens. Each of these individuals had a positive immediate skin prick test to peanut and either a positive double-blind, placebo controlled, food challenge or a convincing history of peanut anaphylaxis (laryngeal edema, severe wheezing, and/or hypotension). Details of the challenge procedure and interpretation have been discussed previously. One individual with elevated serum IgE levels (who did not have peanut specific IgE or peanut hypersensitivity) was used as a control in these studies. At least five mls of venous blood were drawn from each patient and allowed to clot, and the serum was collected. All studies were approved by the Human Use Advisory Committee at the University of Arkansas for Medical Sciences.

Isolation and amino acid sequence analysis of peanut allergen Ara h 2. Ara h 2 was purified to near homogeneity from whole peanut extracts according to the methods of Burks et al. Purified Ara h 2 was electrophoresed on 12.5% acrylamide mini-gels (Bio-Rad. Hercules, Calif.) in Tris glycine buffer. The gels were stained with 0.1% Coomassie blue in 10% acetic acid, 50% methanol, and 40% water for 3 h with continuous shaking. Gel slices containing Ara h II were sent to the W. M. Keck Foundation (Biotechnology Resource Laboratory, Yale University, New Haven Conn.) for amino acid sequencing. Amino acid sequencing of intact Ara h 2 and tryptic peptides of this protein was performed on an Applied Biosystems sequencer with an on-line HPLC column that was eluted with increasing concentrations of acetonitrile.

Peanut RNA isolation and northern (RNA) gels. Three commercial lots from the 1979 crop of medium grade peanut species, Arachis hypogaea (Florunner) were obtained from North Carolina State University for this study. Total RNA was isolated from one gram of this material according to procedures described by Larsen. Poly A+ RNA was isolated using a purification kit supplied by collaborative Research (Bedford MA) according to manufacturer's instructions. Poly A+ RNA was subjected to electrophoresis in 1.2% formaldehyde agarose gels, transferred to nitrocellulose, and hybridized with $^{32}$P-labeled probes according to the methods of Bannon et al.

Computer analysis of Ara h II sequence. Sequence analysis of the Ara h 2 gene was done on the University of Arkansas for Medical Science's Vax computer using the Wisconsin DNA analysis software package. The predicted Ara h 2 epitopes are based on a algorithms developed by Jameson and Wolf (1988) that relates antigenicity to hydophilicity, secondary structure, flexibility, and surface probability.

cDNA expression library construction and screening. Peanut poly A+ RNA was used to synthesize double-stranded cDNA according to the methods of Watson and Jackson and Huynh et al. The cDNA was treated with EcoRI methylase and then ligated with EcoRI and XhoI linkers. The DNA was then ligated with EcoRI-XhoI cut, phosphatase treated Lambda ZAP XR phage arms (Stratagene, LaJolla, Calif.) and in vitro packaged. The library was 95% recombinants carrying insert sizes >400 bp. The library was screened using an IgE antibody pool consisting of an equal volume of serum from each patient with peanut hypersensitivity. Detection of primary antibody was with $I^{125}$-labeled anti-IgE antibody performed according to the manufacturer's instructions (Sanofi, Chaska, Minn.).

PCR amplification of the Ara h 2 mRNA sequence. Using the oligonucleotide CA(AG)CA(AG)TGGGA(AG)TT(AG)CA(AG)GG(N)GA(TC)AG (SEQ ID NO:14) derived from amino acid sequence analysis of the Ara h 2 peanut allergen as one primer and a 23 nucleotide long primer which L hybridizes to the Bluescript vector, the cDNA that encodes Ara h 2 was amplified from the IgE positive clones. Reactions were carried out in a buffer containing 3 mM MgCl$_2$, 500 mM KCl, 100 mM Tris-HCl, pH 9.0. Each cycle of the polymerase chain reaction consisted pf 1 min at 94° C., followed by 2 min at 42° C., and three minutes at 72° C. Thirty cycles were performed with both primers present in all cycles. From this reaction, a clone carrying an approximately 700 bp insert was identified.

DNA sequencing and analysis. DNA Sequencing was done according to the methods of Sanger et al. using either $^{32}$P-end labeled oligonucleotide primers or on a automated ABI model 377 DNA sequencer using fluorescent tagged nucleotides. Most areas of the clone were sequenced at least twice and in some cases in both directions to ensure an accurate nucleotide sequence for the Ara h 2 gene.

Peptide synthesis. Individual peptides were synthesized on a derivatised cellulose membrane using Fmoc amino acid active esters according to the manufacturer's instructions (Genosys Biotechnologies, Woodlands, Tex.). Fmoc-amino acid derivatives were dissolved in 1-methyl-2-pirrolidone and loaded on marked spots on the membrane. Coupling reactions were followed by acetylation with a solution of 4% (v/v) acetic anhydride in N,N-Dimethylformamide (DMF). After acetylation, Fmoc groups were removed by incubation of the membrane in 20% (v/v) piperdine in DMF. The membrane was then stained with bromophenol blue to identify the location of the free amino groups. Cycles of coupling, blocking, and deprotection were repeated until the peptides of the desired length were synthesized. After addition of the last amino acid in the peptide, the amino acid side chains were deprotected using a solution containing a 1/1/ 0.5 mixture of dichloromethane/trifluoroacetic acid/ triisobutlysilane. Membranes were either probed immediately or stored at −20° C. until needed.

IgE binding assay. Cellulose membranes containing synthesized peptides were washed with Tris-buffered saline (TBS) and then incubated with blocking solution overnight at room temperature. After blocking, the membranes were incubated with serum from patients with peanut hypersensitivity diluted (1:5) in a solution containing TBS and 1% bovine serum albumin for at least 12 h at 4° C. or 2 h at room temperature. Detection of the primary antibody was with $^{25}$I-labeled anti-IgE antibody (Sanofi, Chaska, Minn.).

Results

Isolation and partial amino acid sequence determination of the Ara h 2 protein. The amino terminus of the purified Ara h 2 protein, or peptides resulting from trypsin digestion of this protein, were used for amino acid sequence determination. It was possible to determine the first 17 residues from peptide I and the first 13 residues from peptide II of the major peptide in each fraction. The amino acid sequence representing the amino terminus of the Ara h 2 protein (peptide I) and a tryptic peptide fragment (peptide II) is noted in Table 9. These results confirm and extend previous amino acid sequence analysis of the Ara h 2 protein.

Identification and characterization of clones that encode peanut allergen Ara h 2. RNA isolated from the peanut species, Arachis hypogaea (Florunner) was used to construct an expression library for screening with serum IgE from patients with peanut hypersensitivity. Numerous IgE binding clones were isolated from this library after screening $10^6$ clones with serum IgE from a pool of patients with reactivity to most peanut allergens by Western blot analysis. Since the number of plaques reacting with serum IgE was too large to study all in detail we randomly selected a small portion of the positive clones for further analysis.

To identify which of the clones encoded the Ara h 2 allergen, a hybridization probe was constructed using an oligonucleotide developed from Ara h 2 amino acid sequence and PCR technology. The oligonucleotide sequence CA(AG)CA(AG)TGGGA (AG)TT(AG)CA(AG) GG(N)GA(TC)AG (SEQ ID NO:14) was derived from the amino terminus of the Ara h 2 peanut allergen (peptide I). Utilizing this oligonucleotide, an ~700-bp CDNA clone was identified. DNA sequence revealed that the selected clone carried a 741-base insert which included a 21-base poly A tail and a 240 base 3' non-coding region. This insert contained a large open reading frame starting with an ACG codon And ending with a TAA stop codon at nucleotide position 480 (FIG. 6). The calculated size of the protein encoded by this open reading frame was ~17.5 kD, which is in good agreement with the molecular weight of Ara h 2 that has been determined experimentally. The amino acid sequence that was determined from the amino terminus and a tryptic peptide from purified Ara h 2 (Table 9) were found in this clone. The additional, coding region on the amino terminal end of this clone probably represents a signal peptide which would be cleaved from the mature Ara h 2 allergen.

To determine what size mRNA this clone identified, 32P-labeled insert was used as a hybridization probe of a Northern blot containing peanut poly(A)+ RNA. This insert hybridized to an ~0.7-kb mRNA. Since the size of the cloned insert and the size of the mRNA were in good agreement, coupled with the good agreement in both the calculated and determined size of the Ara h 2 protein and the identity of the determined amino acid sequence with that which was determined from the clone, we concluded that an Ara h 2 specific clone had been isolated.

Peanut allergen Ara h 2 is a conglutin-like seed storage protein. A search of the GenBank database revealed significant amino acid sequence homology between the Ara h 2 protein and a class of seed storage proteins called conglutins. There was ~32% identity with the Ara h 2 protein and a delta conglutin from the lupin seed. These results indicate that the Ara h 2 allergen belongs to a conglutin-like family of seed storage proteins.

Figure 7:
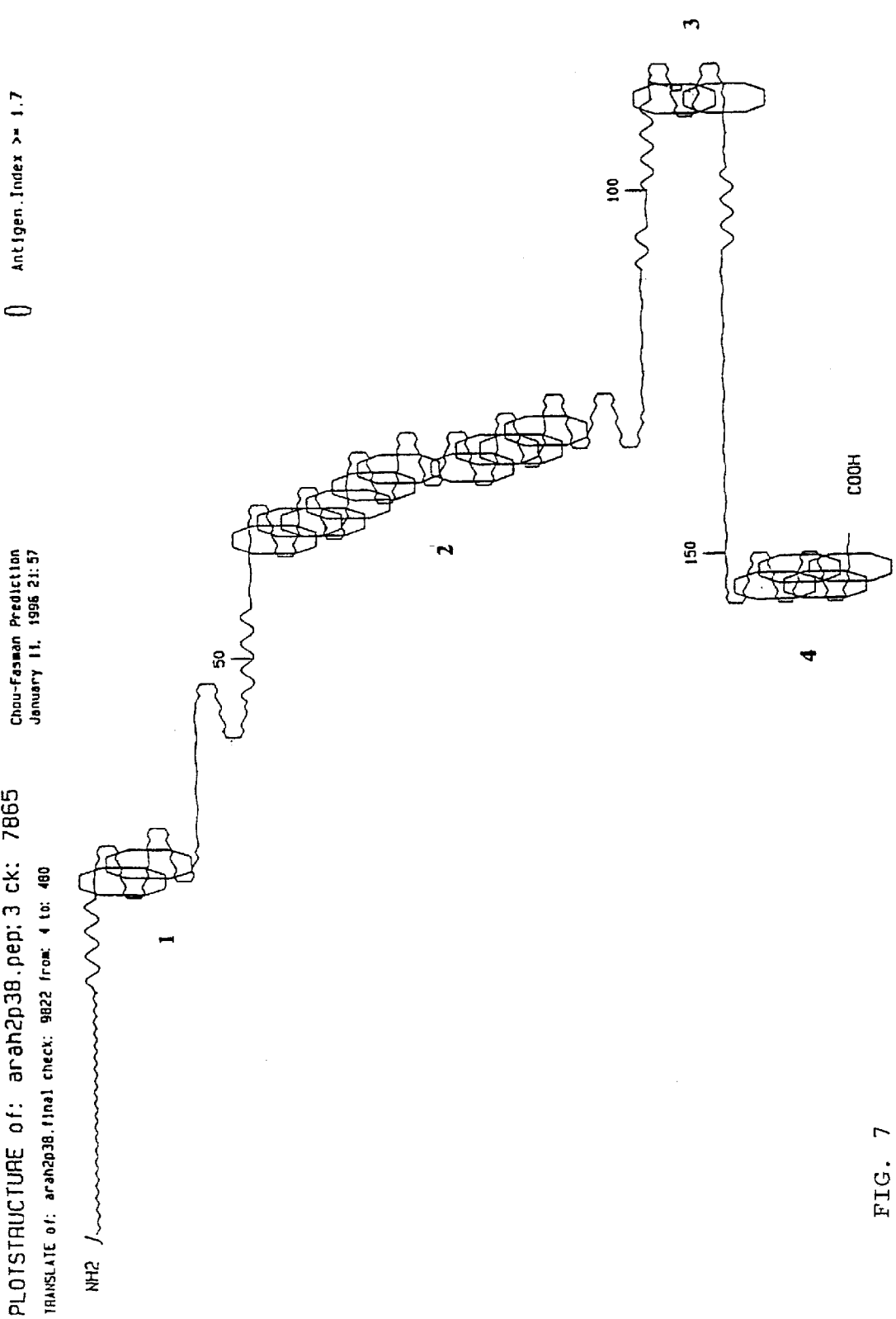

Multiple IgE binding epitopes on the Ara h 2 protein. The Ara h 2 protein sequence was analyzed for potential antigenic epitopes by algorithms designed to determine which portion(s) of this protein could be responsible for antibody binding. There were four possible antigenic regions predicted by this analysis along the entire length of the molecule (FIG. 7).

Nineteen overlapping peptides representing the derived amino acid sequence of the Ara h 2 protein were synthesized to determine if the predicted antigenic regions, or any other regions, were recognized by serum IgE. Each peptide was 15 amino acids long and was offset from the previous peptide by eight amino acids. In this manner, the entire length of the Ara h 2 protein could be studied in large overlapping fragments. These peptides were then probed with a pool of serum from 12 patients with documented peanut hypersensitivity or serum from a control patient with no peanut hypersensitivity. Serum IgE from the control patient did not recognize any of the synthesized peptides (data not shown). In contrast, FIG. 8 shows that there are five IgE binding regions along the entire length of the Ara h 2 protein that are recognized by this population of patients with peanut hypersensitivity. These IgE binding regions were amino acid residues 17–38, 41–62, 57–78, 113–134, and 129–154.

In order to determine the exact amino acid sequence of the IgE binding epitopes, small peptides (10 amino acids long offset by two amino acids) representing the larger IgE binding regions were synthesized. In this manner it was possible to identify individual IgE binding epitopes within the larger IgE binding regions of the Ara h 2 molecule (FIG. 9). The ten IgE binding enitopes that were identified in this manner are shown in Table 10. The size of the epitopes ranged from 6–10 amino acids in length. Three epitopes (aa17–26, aa23–32, aa29–38), which partially overlapped with each other, were found in the region of amino acid residues 17–38. Two epitopes (aa41–50, aa50–60) were found in region 41–62. Two epitopes (aa59–68, aa67–76) were also found in region 57–78. Finally, three epitopes (aa117–126, aa129–138, aa145–154) were found in the overlappings regions represented by amino acid residues 113–134 and 129–154. Sixty-three percent of the amino acids represented in the epitopes were either polar or apolar uncharged residues. There was no obvious amino acid sequence motif that was shared by all the epitopes, with the exception that epitopes 6 and 7, which contained the sequence DPYSPS amino acids 62–67 of SEQ ID NO:2).

Figure 10:
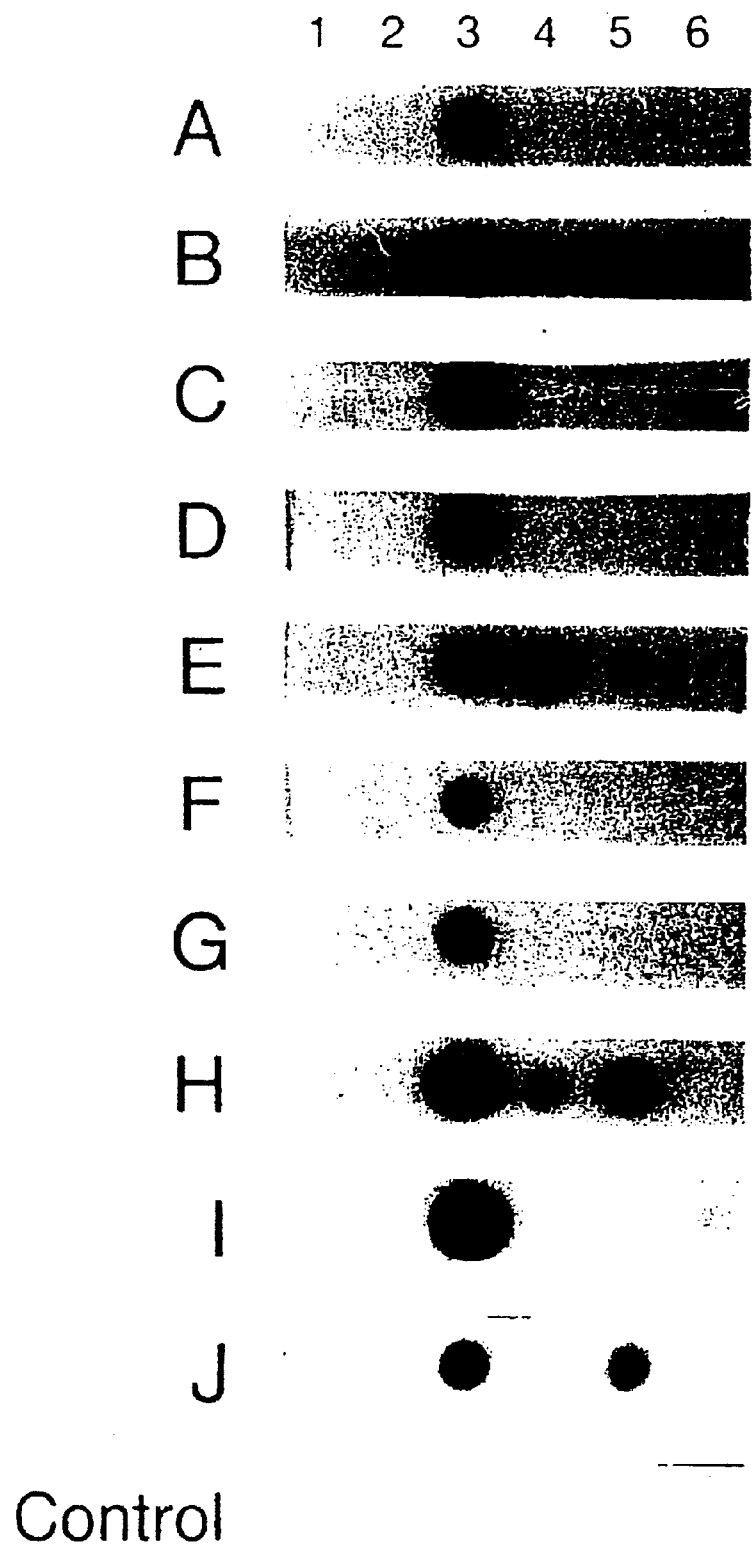

In an effort to determine which, if any, of the ten epitopes were recognized by the majority of patients with peanut hypersensitivity each set of ten peptides was probed individually with serum IgE from 10 different patients. Five patients were randomly selected from the pool of 12 patients used to identify the common epitopes and five patients were selected from outside this pool. An immunoblot strip containing these peptides was incubated with an individual's patient serum. The remaining patients were tested in the same manner and the intensity of IgE binding to each spot was determined as a function of that patient's total IgE binding to these ten epitopes (FIG. 10). All of the patient sera tested (10/10) recognized multiple epitopes (Table 11). The average number of epitopes recognized was about 4–5/patient ranging from two sera recognizing only 3 epitopes and one patients' sera recognizing as many as 7 epitopes. Interestingly, epitopes 3, 6, and 7 were recognized by all patients tested (10/10). No other epitope was recognized by more than 50% of the patients tested.

Discussion

Peanuts are one of the most common food allergens in both children and adults. In addition, peanut hypersensitivity is less likely to resolve spontaneously and more likely to result in fatal anaphylaxis. Because of the significance of the allergic reaction and the widening use of peanuts as protein extenders in processed food, the risk to the peanut-sensitive individual is increasing.

Various studies over the last several years have examined the nature and location of the multiple allergens in peanuts. Taylor et al. demonstrated that the allergenic portion of peanuts was in the protein portion of the cotyledon. Our laboratory recently identified two major allergens from peanut extracts, designated Ara h 1 and Ara h 2. Greater than 90% of our patients who were challenge positive to peanut had specific IgE to these proteins. The Ara h 1 allergen has been identified as a seed storage protein with significant homology to the vicilins, a family of proteins commonly found in many higher plants. The Ara h 2 nucleotide sequence identified in this report has significant sequence homology with another class of seed storage proteins called conglutins. It is interesting to note that two of the major peanut allergens thus far identified are seed storage proteins that have significant sequence homology with proteins in other plants. This may explain the cross-reacting antibodies to other legumes that are found in the sera of patients that manifest clinical symptoms to only one member of the legume family.

In the present study we have determined that there were multiple antigenic sites predicted for the Ara h 2 allergen. As has been found for another peanut allergen Ara h 1, and other allergens in general, there was good agreement between those residues predicted by computer analysis and B-cell epitopes determined by experimental analysis of overlapping peptides. This strong correlation between predicted and determined epitopes is probably due to the ability of the computer model to predict which regions of the molecule are accessible to immunoglobulin interactions. In fact, 3-D structural models of the Ara h 1 protein indicate that most of the peptides identified by computer modeling and experimental analysis as IgE binding epitopes are located on the surface of the molecule (unpublished observation).

There are at least 10 IgE recognition sites distributed throughout the major peanut allergen Ara h 2. The identification of multiple epitopes on a single allergen is not novel, there being reports of multiple IgE binding epitopes on allergens from many foods that cause immediate hypersensitivity reactions. The observation that most of these proteins have multiple IgE binding sites probably reflects the polyclonal nature of the immune response to them and may be a necessary step in establishing a protein as an allergen.

Recent evidence suggests that there is a preferential variable heavy chain usage in IgE synthesis and a direct switching from IgM production to IgE synthesis. This would suggest that epitopes responsible for antigen-specific IgE antibody production may differ from those promoting antigen-specific IgG antibodies and that there may be some structural similarity between peptides that elicit IgE antibody production. However, there was no obvious sequence motif that was shared by the 23 different IgE binding epitopes of the peanut allergen Ara h 1. In the present study, two epitopes share a hexameric peptide (DPYSPS). It is significant to note that these peptides are recognized by serum IgE from all the peanut-hypersensitive patients tested in this study. In addition, serum IgE that recognize these peptides represent the majority of Ara h 2 specific IgE found in these patients. Whether there is any further structural similarity between the IgE binding epitopes of Ara h 2 remains to be determined.

The elucidation of the major IgE binding epitopes on Ara h 2 may enable us to design better therapeutic options for the prevention of anaphylaxis as a result of peanut hypersensitivity. The only therapeutic option presently available for the prevention of a food hypersensitivity reaction is food avoidance. Unfortunately, for a ubiquitous food such as peanut, the possibility of an inadvertent ingestion is great. One therapeutic option used extensively for patients with allergic reactions to various aeroallergens and insect sting venoms is allergen desensitization immunotherapy. Allergen immunotherapy consists of injections of increasing amounts of allergens to which a patient has Type I immediate hypersensitivity. While the absolute mechanism of immunotherapy is unknown, an increase in IgG or $IgG_4$ antibody activity, a decrease in allergen-specific IgE levels, and a decrease in basophil activity have all been implicated in mediating this response. Because allergen immunotherapy has been proven efficacious for treatment of some allergies, treatment with peanut immunotherapy is now being studied as a possible option. Our work showing the IgE binding epitopes of a major peanut allergen may allow for the use of immunodominant epitopes in this approach.

Another potential immunotherapeutic approach that has recently attracted much attention is the use of DNA vaccines. In this approach a promoter region is placed 5' to the cDNA encoding the allergen and then introduced to the whole animal via intramuscular injection or intradermal application. Early work with a dust mite allergen, Der p 1, indicates that this approach can both prevent the development of an immunogenic response to a specific protein and dampen the response to a protein to which the animal has already been sensitized. We are currently exploring this possibility with the Ara h 2 allergen.

FIGURE LEGENDS

FIG. 6. Nucleotide Sequence of an Ara h II cDNA Clone. The nucleotide sequence is shown on the first line (SEQ ID NO:1). The second line is the derived amino acid sequence (SEQ ID NO:2). Bold amino acid residues are those areas which correspond to the determined amino acid sequence of peptide I and II of Ara h II (Table 9) . The numbers on the right of the figure indicate the nucleotide sequence.

An Ara h II Clone Hybridizes to a 700 b Peanut mRNA. Peanut poly A+ RNA was isolated from Arachis hypogaea (Florunner) species and 10 ug were electrophoresed on formaldehyde denaturing agarose gels. Insert from an Ara h II clone was purified, labeled with alpha-$^{32}$P-dCTP, and used as a hybridization probe for Northern blot analysis of this gel. Sizes of known RNA species are expressed in kilobases along the right side of the figure.

FIG. 7. Multiple Predicted Antigenic Sites are Present in the Ara h 2 Allergen. The amino acid sequence of the Ara h 2 protein was analyzed for potential antigenic epitopes by the Jameson and Wolf (1988) algorithm. These predictions are based on a model that relates antigenicity to hydrophilicity, secondary structure, flexibility, and surface probability. There were 4 predicted regions (1–4) that contained multiple antigenic sites (octagons) along the entire length of the molecule. Amino acid residues (small numbers) are represented as alpha-helical (sinusoidal curve), Beta-sheet (saw tooth curve), and coil (flat sinusoidal curve) conformations. Beta turns are denoted by chain reversals.

FIG. 8. Multiple IgE Binding Sites Identified in the Ara h 2 Allergen. Epitope analysis was performed on the Ara h 2 allergen (SEQ ID NO:2) by synthesizing 15 amino acid long peptides, offset from each other by 8 amino acids for the entire protein molecule. These peptides, represented as spots 1–19, were then probed with a serum pool consisting of 15 patients with documented peanut hypersensitivity.

FIG. 9. Core IgE Binding Epitopes Identified on the Ara h 2 Allergen. Epitope analysis was performed on the IgE binding sites identified in FIG. 8 by synthesizing 10 amino acid long peptides offset by two amino acids. These peptides were then probed with the 18 patient serum pool. FIG. 9 is the peptide analysis of Ara h II amino acid residues 49–70 (SEQ ID NO:2). FIG. 9 identifies the amino acid sequence of this region.

FIG. 10. Of the 10 patients five were selected at random from the 18 patient serum pool and five were patients with peanut hypersensitivity that were not included in the pool. Patient K represents a non-peanut sensitive (negative) control.

Characterization of a Major Peanut Allergen: Mutational Analysis of the Ara h 1 IgE Binding Epitopes Immediate hypersensitivity reactions to foods occur in about 6–8% of young children and it of adults. These reactions are mediated by the production of IgE antibodies to glycoproteins found in the food. Peanuts are a major cause of serious allergic reactions in both adults and children. Ara h 1, a major peanut allergen, has been extensively characterized and shown to contain 23 linear IgE binding epitopes. We set out to determine the amino acids critical to their binding and to determine the location of these epitopes on the 3-D structure of the Ara h 1 molecule. To accomplish this, mutational analysis of each epitope was performed by synthesizing 10 amino acid long peptides with single amino acids changed at each position to alanine, followed by determination of the IgE binding capacity of each mutated epitope relative to wild-type. It was determined that changes in those amino acids located at positions, 4, 5, and 6 of the epitope have a greater influence than residues located on either end. In addition, the substitution of most apolar, charged residues resulted in the loss of IgE. More importantly, 21/23 epitopes could be mutated to non-IgE binding by a single amino acid substitution. The 3-D model of the Ara h 1 protein indicates that the majority of the IgE binding epitopes are located on the surface of the molecule. Currently, we are determining what effect the amino acid substitutions that lead to loss of IgE binding will have on the tertiary structure of the protein.

TABLE 9

AMINO ACID SEQUENCE OF *Ara h* 2 PEPTIDES

| Peptide | Amino Acid Sequence |
|---|---|
| I | X-Q-Q-W-E-L-Q-G-D-R-R-R-Q-S-Q-L-E-R (SEQ ID NO:15) |
| II | A-N-L-R-P-C-E-Q-H-L-M-Q-K (amino acids 39–51 of SEQ ID NO:2) |

The amino acid sequence of the amino terminus (I) and a tryptic peptide (II) derived from Ara h 2 protein was determined. The sequence is shown as the one letter amino acid code.

TABLE 10

*Ara h* 2 IgE BINDING EPITOPES (SEQ ID NO:2)

| PEPTIDE | AA SEQUENCE | *Ara h* 2 POSITION |
|---|---|---|
| 1 | HASARQQWEL | 17–26 |
| 2 | QWELQGDRRC | 23–32 |
| 3 | DRRCQSQLER | 29–38 |
| 4 | LRPCEQHLMQ | 41–50 |
| 5 | KIQRDEDSYE | 51–60 |
| 6 | YERDPYSPSQ | 59–68 |
| 7 | SQDPYSPSPY | 67–76 |
| 8 | DRLQGRQQEQ | 117–126 |
| 9 | KRELRNLPQQ | 129–138 |
| 10 | QRCDLDVESG | 145–154 |

TABLE 11

IgE BINDING TO Ara h 2 EPITOPES

| | 1 | 2 | 3 | 4 | 5 | 6 | 7 | 8 | 9 | 10 | Epitopes/ Pt |
|---|---|---|---|---|---|---|---|---|---|---|---|
| A | | | X | | | X | X | X | | | 4 |
| B | X | | X | X | | X | X | | | | 5 |
| C | X | | X | X | | X | X | | | | 5 |
| D | | | X | | | X | X | X | | | 4 |
| E | | X | X | | | X | X | | | | 4 |
| F | X | | X | X | | X | X | X | | X | 7 |
| G | | | X | | | X | X | | | | 3 |
| H | | | X | X | X | X | X | X | | | 6 |
| I | | | X | | | X | X | | | | 3 |
| J | X | | X | | | X | X | | X | | 5 |
| Pts/ Epitope | 4 | 1 | 10 | 4 | 1 | 10 | 10 | 4 | 1 | 1 | |

Patients are indicated by letters (A–J) on the left hand side of the table. Ara h 2 peptides are indicated by number (1–10) across the top of the table. The number of epitopes recognized by each patient (epitopes/patient) is shown on the right hand side of the table. The number of patients that recognized each epitope is shown across the bottom of the table. An X indicates that a peptide bound IgE.

Cloning, Epitope Mapping, and Mutational Analysis of Ara h 2, a Major Peanut Allergen A major peanut allergen, Ara h 2, is recognized by serum IgE from 90% of patients with peanut hypersensitivity. Biochemical characterization of this allergen indicates that it is a glycoprotein of ~17.5 kDa. Using N-terminal amino acid sequence data from purified Ara h 2, oligonucleotide primers were synthesized and used to identify a clone (700 bp) from a peanut cDNA library. This clone was capable of encoding a 17.5 kDa protein with homology to the conglutin family of seed storage proteins. The major linear IgE binding epitopes of this allergen were mapped using overlapping peptides synthesized on an activated cellulose membrane and pooled serum IgE from 15 peanut sensitive patients. Ten IgE binding epitopes were identified, distributed throughout the length of the Ara h 2 protein. The size of the epitopes ranged from 6–10 amino acids in length. Sixty-three percent of the amino acids represented in the epitopes were either polar or apolar uncharged residues. In an effort to determine which, if any, of the ten epitopes were recognized by the majority of patients with peanut hypersensitivity, each set of ten peptides was probed individually with serum IgE from 10 different patients. All of the patient sera tested recognized multiple epitopes. Three epitopes (aa29–38, aa59–68, and 67–76) were recognized by all patients tested. Mutational analysis of these immunodominant epitopes indicate that single amino acid changes result in loss of IgE binding. Both epitopes contained in region aa59–76 contained the amino acid sequence DPYSPS (amino acids 62–67 of SEQ ID NO:2) that appears to be necessary for IgE binding. These results may allow for the design of improved diagnostic and therapeutic approaches to peanut hypersensitivity.

Ara h 3, a Peanut Allergen Identified by Using Peanut Sensitive Patient Sera Adsorbed with Soy Proteins Peanuts and soybeans are members of the legume family and share several common antigenic fractions. Patients allergic to one of these foods have serum IgE antibodies which immunologically cross-react with other legumes. However, ingestion of other legumes generally does not induce an allergic reaction, suggesting that cross-reacting antibodies to soy were removed from the sera of patients clinically allergic to peanuts. Adsorbed sera were then used to identify specific IgE binding to peanut immunoblots. Several peanut proteins ranging in size from 5 kDa to 49 kDa, were identified. A~14 kDa protein identified in this manner was purified and prepared for amino acid sequence analysis. Amino terminal sequencing determined the first 23 amino acids of this protein. A search of the Genbank protein database with this peptide revealed that it had 61% identity with a soybean gene for glycinin subunit G3. A degenerate oligonucleotide primer was then designed from this data to use in conjunction with vector primers to amplify the clones that encode this protein from a peanut cDNA library. DNA sequencing of these clones also revealed ~70% homology with the soybean gene for glycinin subunit G3. These data indicate that while there is significant homology between the peanut and soybean glycinins there must be peanut-specific epitopes responsible for the binding of the soy-adsorbed serum IgE. Subsequent characterization of this allergen will include determination of the IgE binding epitopes and testing of the clinical relevance of this protein in peanut hypersensitivity. If this strategy is successful it will not only identify proteins that bind IgE but also those allergens and epitopes important in the disease process.

Mapping of the B-Cell Epitopes on Ara h I and Ara h II Legume Storage Proteins and Major Allergens Involved in Peanut Hypersensitivity Approximately 8% of children and 1–2% of adults suffer from some form of food allergy. Reactions to peanuts are more likely m than other food allergies to give rise to fatal or near fatal anaphylaxis in sensitized patients. Ara h I (MW=63.5 kD) and Ara h II (MW=17 kD) are peanut proteins recognized by serum IgE from 90% of peanut sensitive patients, thus establishing them as clinically important allergens. Overlapping peptides representing the entire Ara h I and Ara h II molecules were constructed and IgE immunoblot analysis performed to determine which portions of these allergens were responsible for IgE binding. Utilizing a pool (n=15) of patients with peanut hypersensitivity, 23 IgE binding epitopes were identified on Ara h I and 6 epitopes were identified on Ara h II. Even though there were multiple epitopes identified on each allergen, two epitopes on Ara h I and one epitope on Ara h II were recognized by 90% of individual patient sera tested (n=10). The amino acids important for IgE binding in these immunodominant epitopes were determined by mutational analysis. The identification of the major Ara h I and Ara h II IgE binding epitopes may lead to improved diagnosis of peanut hypersensitivity and eventually to an improved therapeutic regimen for this disease. SUPPORTED IN PART BY THE NATIONAL INSTITUTE OF HEALTH, CLARISSA SOSIN ALLERGY RESEARCH FOUNDATION, AND ARKANSAS SCIENCE AND TECHNOLOGY AUTHORITY.

Introduction

Approximately 1–2% of the USA population suffers from some for of food allergy. Peanuts, fish, tree nuts, and shell fish account for the majority of food hypersensitivity reactions in adults; while peanuts, milk, and eggs cause over 80% of food hypersensitivity reactions in children. Unlike the food hypersensitivity reactions to milk and eggs, peanut hypersensitivity reactions usually persist into adulthood and last for a lifetime. In addition, hypersensitivity reactions to peanuts tend to be more severe than those to other food allergens, sometimes resulting in death. Several reports have detailed the fatal and near-fatal anaphylactic reactions occurring in adolescents and adults. Currently, avoidance is the only effective means of dealing with food allergy, but the use of peanuts and peanut by-products as supplements in many different foods makes accidental consumption almost inevitable.

Two major allergens involved in peanut hypersensitivity are the peanut proteins, Ara h I and Ara h II. These proteins are recognized by 90% of peanut positive patients, thus establishing them as clinically important allergens. Both proteins are seed storage proteins. Ara h I shares significant sequence homology with vicilin proteins from other plants while Ara h II is a conglutin like protein.

Food hypersensitivity reactions occur -shortly after contact of a specific allergen with its corresponding IgE antibodies which are bound to mast cells. IgE, when complexed with antigen, will activate mast cells to release histamine, heparin, and other substances which are responsible for the clinical symptoms observed. Thus the IgE binding epitopes of the allergens play an important role in the disease process and their elucidation will lead to a better understanding of the human immune response involved in food hypersensitivity reactions and to improved diagnostic and therapeutic capabilities.

FIGS. 1 and 7. Multiple Predicted Antigenic Sites in the Ara h I and Ara h II Allergens The amino acid sequences of the Ara h I and Ara h II proteins were analyzed for potential antigenic epitopes.

These predictions are based on a model that relates antigenicity to hydrophilicity, secondary structure, flexibility, and surface probability. There were 11 (1–11) predicted regions that contained multiple antigenic sites (octagons) along the entire length of the Ara h I protein and 4 (1–4) predicted regions on the Ara h II protein. Amino acid residues (small numbers) are represented as alpha-helical (sinusoidal curve), Beta sheet (saw tooth curve), and coil (flat sinusoidal curve) conformations. Beta turns are denoted by chain reversals.

FIGS. 2 and 8. Multiple IgE Binding Regions Identified in the Ara h I and Ara h II Allergens Upper Panels: Epitope mapping was performed on the Ara h I and Ara h II allergens by synthesizing each of these proteins in 15 amino acid long overlapping peptides that were offset from each other by 8 amino acids. These peptides were then probed with a pool of serum IgE from 15 patients with documented peanut hypersensitivity. The position of the peptides within the Ara h I and Ara h II proteins are indicated on the left hand side of each panel. Lower Panels: The amino acid sequences of the Ara h I and Ara h II proteins are shown in the lower panels. The numbered boxes correspond to the predicted antigenic regions (P1–P11; P1–P4). The hatched boxes (D1–D12; D1–4) correspond to the IgE binding regions shown in the upper panels.

FIGS. 3 and 9. Core IgE Binding Epitopes Identified in the Ara h I and Ara h II Allergens Detailed epitope mapping was performed on IgE binding regions identified in FIGS. 2 and 8 by synthesizing 10 amino acid long peptides offset from each other by two amino acids. These peptides were then probed with a pool of serum IgE from 15 patients with documented peanut hypersensitivity. The data shown represents regions D2 and a portion of D3 from Ara h I and region D2 from Ara h II. Numbers correspond to peptides as shown in Table 12. The amino acid sequences of Ara h I and Ara h II that were tested in the upper panels are shown. Shaded areas of boxes correspond to IgE binding peptides.

FIGS. 4 and 10. Commonly Recognized Ara h I Epitopes

Core IgE binding epitopes were synthesized (10 amino acids long) and then probed individually with serum IgE from 10 patients with documented peanut hypersensitivity. The top panels represent where each of the Ara h I peptides (1–23) and Ara h II peptides (1–6) were placed on the membrane. Panels A–J show the peptides that bound serum IgE from each patient. The control panels were probed with sera from a patient with elevated IgE but who does not have peanut hypersensitivity.

FIGS. 5 and 11. Amino Acids Involved in IgE Binding

Epitopes 4 and 17 from Ara h I and epitope 3 from Ara h II were synthesized with a glycine (G) or alanine (A) residue substituted for one of the amino acids in each of these peptides and then probed with a pool of serum IgE from 15 patients with documented peanut hypersensitivity. The letters across the top of each panel indicate the one letter amino acid code for the residue normally at that position and the amino acid that was substituted for it. The numbers indicate the position of each residue in the Ara h I and Ara h II proteins.

SUMMARY

The major peanut allergens Ara h I and Ara h II have been cloned, sequenced, and identified as seed storage proteins.

B-cell epitopes of Ara h I and 6 B-cell epitopes of Ara h II were mapped using synthetic peptides probed with serum IgE from a population of peanut hypersensitive patients.

Epitope #4 (AA89–98) and #17 (AA498–507) of Ara h I and epitope #3 (AA59–66) of Ara h II were recognized by 90% of peanut hypersensitive patients tested.

Amino acids important to IgE binding of the immunodominant epitopes of Ara h I and Ara h II were determined.

FIG. 12 is the same as Table 16 with peptides I, II, III corresponding to the peptides in Table 14 highlighted by rectangular boxes (SEQ ID NO: 23 & 4).

Table 16 is a partial Ara h I Beta sequence (clone 5Ala).

Table 17 is an Ara h I Alpha sequence (clone p17).

Table 18 is the Ara h II sequence (clone Ara h II p38).

Table 19 is the Ara h I Beta sequence (clone p41b).

Table 20 is the Ara h II p38 translation of Ara h II p38.

In accordance with the present invention, it is contemplated that the discovery or identification of particular peptides or epitopes which bind IgE and cause an IgE response by a person having an allergy or sensitivity to that particular protein may be used to produce a DNA vaccine for immunization therapy to hopefully reduce the IgE response and thereby eliminate or reduce the negative effects of the allergy or sensitivity. For example, a protein, peptide, or epitope can be produced and injected into a patient as a DNA vaccine which hopefully will have an immuno modulation effect of the IgE response and stimulate a different response, such as IgG, IgM, IgA, etc. and thereby down regulate IgE senthesis to the specific allergen.

Also in accordance with the present invention, similar peptides, epitopes and IgE binding proteins from other legumes, herbs, oil seeds, and the like, for example soybeans or wheat, can be isolated and identified, mutated so that they do not bind IgE, and used in a mutated DNA vaccine for immunization therapy.

TABLE 12

| | *Ar h* I IgE Binding Epitopes (SEQ ID NO:4) | |
|---|---|---|
| PEPTIDE | AA SEQUENCE* | *Ara h* I POSITION |
| 1 | A K S S P Y Q K K T | 25–34 |
| 2 | Q E P D D L K Q K A | 48–57 |
| 3 | L E Y D P R L V Y D | 65–74 |
| 4 | G E R T R G R Q P G | 89–98 |
| 5 | P G D Y D D D R R Q | 97–106 |
| 6 | P R R E E G G R W G | 107–116 |
| 7 | R E R E E D W R Q P | 123–132 |
| 8 | E D W R R P S H Q Q | 134–143 |
| 9 | Q P R K I R P E G R | 143–152 |
| 10 | T P G Q F E D F F P | 294–303 |
| 11 | S Y L Q E F S R N T | 311–320 |
| 12 | F N A E F N E I R R | 325–334 |
| 13 | E Q E E R G Q R R W | 344–353 |

TABLE 12-continued

| 14 | D I T N P I N L R E | 393–402 |
| 15 | N N F G K L F E V K | 409–418 |
| 16 | G T G N L E L V A V | 461–470 |
| 17 | R R Y T A R L K E G | 498–507 |
| 18 | E L H L L G F G I N | 525–534 |
| 19 | H R I F L A G D K D | 539–548 |
| 20 | I D Q I E K Q A K D | 551–560 |
| 21 | K D L A F P G S G E | 559–568 |
| 22 | K E S H F V S A R P | 578–587 |
| 23 | P E K E S P E K E D | 597–606 |

Ar h II Ige Binding Epitopes
(SEQ ID NO:2)

| PEPTIDE | AA SEQUENCE* | Ara h II POSITION |
|---|---|---|
| 1 | L L A A H A S A R Q | 13–22 |
| 2 | Q G D R R C Q S Q L | 27–36 |
| 3 | Y E R D P Y S P S Q | 59–68 |
| 4 | A G S S Q H Q E R C | 81–90 |
| 5 | C N E L N E F E N N | 91–100 |
| 6 | Q R C D L D V E S G | 145–154 |

*The underlined portions of each peptide are the smallest IgE binding sequences as determined by the analysis as described in FIG. 9.

TABLE 13

Ara h I Epitopes
IgE binding of core Ara h I epitopes by serum from peanut hypersensitive individuals.

| Patients | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | Epitopes/Patient |
|---|---|---|---|---|---|---|---|---|---|---|---|---|---|---|---|---|---|---|---|---|---|---|---|---|
| A |   |   |   | X | X |   |   |   |   |   |   |   |   | X |   |   | X | X |   | X |   |   |   | 6 |
| B | X | X |   | X | X |   |   |   |   |   |   |   |   |   | X |   | X |   |   |   |   |   |   | 6 |
| C | X | X | X | X | X | X |   |   | X |   |   | X | X |   | X |   | X |   |   |   |   | X |   | 12 |
| D | X |   |   | X | X |   |   |   |   |   |   |   | X |   | X |   | X |   |   |   |   |   |   | 6 |
| E |   |   | X | X |   |   |   |   | X | X | X | X |   |   |   |   | X |   |   | X | X | X |   | 11 |
| F |   | X |   | X |   |   |   |   | X |   |   |   |   |   |   |   | X |   |   |   |   |   |   | 4 |
| G | X | X | X |   |   |   |   |   |   |   |   |   | X |   |   | X | X |   |   |   |   |   |   | 6 |
| H |   | X |   |   | X |   |   |   |   |   |   |   |   |   |   |   | X |   |   |   |   |   |   | 3 |
| I |   |   |   | X |   |   |   | X | X |   |   |   |   |   |   |   | X | X | X | X |   | X |   | 8 |
| J |   |   |   | X |   |   |   | X | X |   |   | X |   |   |   |   | X |   | X |   | X |   |   | 7 |
| Patients/Epitope | 4 | 5 | 4 | 9 | 4 | 1 | 0 | 3 | 4 | 2 | 1 | 3 | 3 | 1 | 3 | 1 | 10 | 2 | 1 | 4 | 1 | 3 | 1 | |

Ara h II Epitopes
IgE binding of core Ara h II epitopes by serum from peanut hypersensitive individuals

| Patients | 1 | 2 | 3 | 4 | 5 | 6 | Epitopes/Patient |
|---|---|---|---|---|---|---|---|
| A |   |   | X |   |   |   | 1 |
| B |   |   | X |   | X |   | 2 |
| C |   |   | X |   |   | X | 2 |
| D |   |   | X |   |   | X | 2 |
| E |   |   | X | X | X |   | 3 |
| F |   |   | X |   |   |   | 1 |
| G |   |   | X |   |   |   | 1 |
| H |   |   | X | X | X |   | 3 |
| I |   |   | X |   |   | X | 2 |
| J |   |   | X |   | X | X | 3 |
| Patients/Epitope | 0 | 0 | 10 | 2 | 4 | 4 | |

Patients are indicated by letters (A–J) on the left hand side of the table. Ara hI II peptides are indicated by number across the top of the table. The number of epitopes recognized by each patient (epitopes/patient) is shown on the right hand side of the table. The number of patients that recognized each epitope (patients/epitope) is shown across the bottom of the table. An X indicates that a peptide bound IgE.

TABLE 14

IDENTIFICATION OF NATIVE AMINO ACID SEQUENCES IN THE DEDUCED AMINO ACID SEQUENCE OF CLONE ARA H 2 P38
THE FOLLOWING AMINO ACID SEQUENCE WAS TRANSLATED FROM THE ARA H 2 P39 GENE (NUCLEOTIDE SEQUENCE) ISOLATED FROM OUR cDNA LIBRARY.

TRANSLATION of GENE: arah2p38

```
                       N-terminal sequence
  1  LTILVALALF LLAAHASARQ QWELQGDRRC QSQLERANLR PCEQHLMQKI
                                                  peptide 45
         peptide 37
 51  QRDEDSYERDPYSPSQDPYS PSPYDRRGAG SSQHQERCCN ELNEFENNQR peptide 20
101  CMCEALQQIM ENQSDRLQGRQQEQQFKREL RNLPQQCGLR APQRCDLDVE

151  SGGRDRY (SEQ ID NO:22)
```

TABLE 15

The following information was obtained by physicochemical measures and used to confirm the deduced amino acid sequence from clone Ara h 2 p38.

17.5 kD N-TERMINAL SEQUENCE: gene sequence 19–48
(SEQ ID NO:16)

| 1 | 2 | 3 | 4 | 5 | 6 | 7 | 8 | 9 | 10 | 11 | 12 |
|---|---|---|---|---|---|---|---|---|----|----|----|
| GLY | GLN | GLN | TRP | GLU | LEU | GLN | GLY | ASP | ARG | ARG | ARG |
| Q | Q | W | E | L | Q | G | D | R | R | R |  |

| 13 | 14 | 15 | 16 | 17 | 18 | 19 | 20 | 21 | 22 | 23 | 24 |
|----|----|----|----|----|----|----|----|----|----|----|----|
| GLN | SER | GLN | LEU | GLU | ARG | ALA | ASN | LEU | X | PRO | X |
| Q | S | Q | L | E | R | A | N | L | R | P | C |

| 25 | 26 | 27 | 28 | 29 | 30 |
|----|----|----|----|----|----|
| GLU | GLN | X | LEU | MET | X |
| E | Q | H | K | M |  |

PEPTIDE 20: identified in gene sequence 121–128:
(SEQ ID NO:22)

| 1 | 2 | 3 | 4 | 5 | 6 | 7 | 8 |
|---|---|---|---|---|---|---|---|
| GLN | GLN | GLU | GLN | GLN | PHE | LYS | ARG |
| Q | Q | E | Q | Q | F | K | R |

PEPTIDE 37: identified in gene sequence 60–76:
(SEQ ID NO:22)

| 1 | 2 | 3 | 4 | 5 | 6 | 7 | 8 | 9 | 10 | 11 | 12 |
|---|---|---|---|---|---|---|---|---|----|----|----|
| ASP | PRO | TYR | SER | PRO | SER | GLN | ASP | PRO | TYR | SER | PRO |

TABLE 15-continued

The following information was obtained by physicochemical measures and used to confirm the deduced amino acid sequence from clone Ara h 2 p38.

| D | P | Y | S | P | S | Q | D | P | Y | S | P |
|---|---|---|---|---|---|---|---|---|---|---|---|

| 13 | 14 | 15 | 16 | 17 |
|----|----|----|----|----|
| SER | PRO | TYR | ASP | ARG |
| S | P | Y | D | R |

PEPTIDE 45: identified in gene sequence 37–49:
(SEQ ID NO:22)

| 1 | 2 | 3 | 4 | 5 | 6 | 7 | 8 | 9 | 10 | 11 | 12 |
|---|---|---|---|---|---|---|---|---|----|----|----|
| ALA | ASN | LEU | ARG | PRO | CMC | GLU | GLN | HIS | LEU | MET | GLN |
| A | N | L | R | P | C | E | Q | H | L | M | Q |

| 13 |
|----|
| LYS |
| K |

TABLE 16

| | |
|---|---|
| LOCUS | ARQARAHI 1340 bp ss-mRNA PLN |
| DEFINITION | *Arachis hypogea* (clone 5 Ala) Ara h I mRNA, complete cds. |
| ACCESSION | L34402 |
| KEYWORDS | . |
| SOURCE | *Arachis hypogea* (strain Florunner) seed cDNA to mRNA. |
| ORGANISM | *Arachis hypogea* |
| | Eukaryota; Plantae; Embryobionta; Magnoliophyta; Magnoliopsida; Rosidae; Fabales; Fabaceae. |
| REFERENCE | 1 (bases 1 to 1340) |
| AUTHORS | Burks, A.W., Cockrell, G., Stanley, J.S., Helm, R.M. and Bannon, G.A. |
| TITLE | Recombinant peanut allergen Ara h I expression and IgE binding in patients with peanut hypersensitivity |
| JOURNAL | Unpublished (1994) |
| STANDARD | full automatic |
| COMMENT | NCBI gi: 508640 |

TABLE 16-continued

```
FEATURES          Location Qualifiers
  source          1 . . . 1340
                  /organism = "Arachis hypogea"
                  /strain = "Florunner"
                  /dev_stage = "seed"
                  /sequenced_mol = "cDNA to mRNA"
  CDS             /231 . . . 1238
                  /gene = "Ara h I"
                  /note = "NCBI gi: 508641"
                  /codon_start = 1
  /translation = "MPVNTPGQFEDFFPASSRDQSSYLQGFSRNTLEAAFNAEFNEIR
  RVLLEENAGGEQEERGQRRWSTRSSENNEGVIVKVSKEHVEELTKHAKSVSKEGSEEE
  GDITNPINLREGEPDLSNNFGKLFEVKPDKKNPQLQDLDMMLTCVEIKEGALMLPHFN
  SKAMVIVVVNKGTGNLELVAVRKEQQQRGRREEEEDEDEEEEGSNREVRRYTARLKEG
  DVFIMPAAHPVAINASSELHLLGFGINAENNHRIFLAGDKDNVIDQIEKQAKDLAFPG
  SGEQVEKLIKNQKESHFVSAQSQSQSPSSPEKESPEKEDQEEENQGGKGPLLSILKAF
  N" (SEQ ID NO:17)
  BASE COUNT     422 a   296 c   340 g   282 t
  ORIGIN
Arqarahi   Length: 1340  05:04  Type: N  Check: 8329 . . .
     1     GTATTGTGCA GATCGAGGCC AAACCTAACA CTCTTGTTCT TCCCAAGCAC
    51     GCTGATGCTG ATAACATCCT TGTTATCCAG CAAGGGCAAG CCACCGTGAC
   101     CGTAGCAAAT GGCAATAACA GAAAGAGCTT TAATCTTGAG GAGGGCATG
   151     CACTCAGAAT CCCATCCGGT TTCATTTCCT ACATCTTGAA CCGACATGC
   201     AACCAGAACC TCAGAGTAGC TAAAATCTCC ATGCCCGTTA ACACACCCGG
   251     CCAGTTTGAG GATTTCTTCC CGGCGAGCAG CCGAGACCAA TCATCCTACT
   301     TGCAGGGCTT CAGCAGGAAT ACGTTGGAGG CCGCCTTCAA TGCGGAATTC
   351     AATGAGATAC GGAGGGTGCT GTTAGAAGAG AATGCAGGAG GTGAGCAAGA
   401     GGAGAGAGGG CAGAGGCGAT GGAGTACTCG GAGTAGTGAG AACAATGAAG
   451     GAGTGATAGT CAAAGTGTCA AAGGAGCACG TTGAAGAACT TACTAAGCAC
   501     GCTAAATCCG TCTCAAAGAA AGGCTCCGAA GAAGAGGGAG ATATCACCAA
   551     CCCAATCAAC TTGAGAGAAG GCGAGCCCGA TCTTTCTAAC AACTTTGGGA
   601     AGTTATTTGA GGTGAAGCCA GACAAGAAGA ACCCCCAGCT TCAGGACCTG
   651     GACATGATGC TCACCTGTGT AGAGATCAAA GAAGGAGCTT TGATGCTCCC
   701     ACACTTCAAC TCAAAGGCCA TGGTTATCGT CGTCGTCAAC AAAGGAACTG
   751     GAAACCTTGA ACTCGTGGCT GTAAGAAAAG AGCAACAACA GAGGGGACGG
   801     CGGGAAGAAG AGGAGGACGA AGACGAAGAA GAGGAGGGAA GTAACAGAGA
   851     GGTGCGTAGG TACACAGCGA GGTTGAAGGA AGGCGATGTG TTCATCATGC
   901     CAGCAGCTCA TCCAGTAGCC ATCAACGCTT CCTCCGAACT CCATCTGCTT
   951     GGCTTCGGTA TCAACGCTGA AAACAACCAC AGAATCTTCC TTGCAGGTGA
  1001     TAAGGACAAT GTGATAGACC AGATAGAGAA GCAAGCGAAG GATTTAGCAT
  1051     TCCCTGGGTC GGGTGAACAA GTTGAGAAGC TCATCAAAAA CCAGAAGGAA
  1101     TCTCACTTTG TGAGTGCTCA ATCTCAATCT CAATCTCCGT CGTCTCCTGA
  1151     GAAAGAGTCT CCTGAGAAAG AGGATCAAGA GGAGGAAAAC CAACGAGGGA
  1201     AGGGTCCACT CCTTTTCAATT TTGAAGGCTT TTAACTGAGA ATGGAGGCAA
  1251     CTTGTTATGT ATCGATAATA AGATCACGCT TTTGTACTCT ACTATCCAAA
  1301     AACTTATCAA TAAATAAAAA CGTTTGTGCG TTGTTTCTCC
           (SEQ ID NO:18)
```

TABLE 17

```
LOCUS         ARQARAH  1949 bp  mRNA  PLN
DEFINITION    Arachis hypogea (clone p17) Ara h I mRNA,
              complete cds.
ACCESSION     L38853
NID           g620024
KEYWORDS      peanut hypersensitivity.
SOURCE        Arachis hypogea (strain Florunner) seed cDNA to mRNA.
  ORGANISM    Arachis hypogea
              Eukaryota; Plantae; Embryobionta; Magnoliophyta;
              Magnoliopsida; Rosidae; Fabales; Fabaceae.
REFERENCE     1 (bases 1 to 1949)
  AUTHORS     Burks, A.W., Cockrell, G., Stanley, J.S., Helm, R.M.
              and Bannon, G.A.
  TITLE       Recombinant peanut allergen Ara h I expression and IgE
              binding in patients with peanut hypersensitivity
  JOURNAL     Unpublished (1994)
COMMENT       NCBI gi: 620024
FEATURES          Location/Qualifiers
  source          1 . . . 1949
                  /organism = "Arachis hypogea"
                  /strain = "Florunner"
                  /dev_stage = "Seed"
                  /sequenced_mol = "cDNA to mRNA"
  5'UTR           1 . . . 2
  CDS             3 . . . 1847
```

TABLE 17-continued

```
                /gene = "Ara h I"
                /note = "NCBI gi: 620025"
                /codon_start = 1
                /db_xref = "PID: g620025"
                /translation = "MRGRVSPLMLLLGILVLASVSATQAKSPYRKTENPCAQRCLQSC
                QQEPDDLKQKACESRCTKLEYDPRCVYDTGATNQRHPPGERTRGRQPGDYDDDRRQPR
                REEGGRWGPAEPREREREEDWRQPREDWRRPSHQQPRKXRPEGREGEQEWGTPGSEVR
                EETSRNNPFYFPSRRFSTRYGNQNGRIRVLQRFDQRSKQFQNLQNHRIVQIEARPNTL
                VLPKHADADNILVIQQGQATVTVANGNNRKSFNLDEGHALRIPSGFISYILNRHDNQN
                LRVAKISMPVNTPGQFEDFFPASSRDQSSYLQGFSRNTLEAAFNAEFNEIRRVLLEEN
                AGGEQEERGQRRRSTRSSDNEGVIVKVSKEHVQELTKHAKSVSKKGSEEEDITNPINL
                RDGEPDLSNNFGRLFEVKPDKKNPQLQDLDMMLTCVEIKEGALMLPHFNSKAMVIVVV
                NKGTGNLELVAVRKEQQQRGRREQEWEEEEEDEEEEGSNREVRRYTARLKEGDVFIMP
                AAHPVAINASSELHLLGFGINAENNHRIFLAGDKDNVIDQIEKQAKDLAFPGSGEQVE
                KLIKNQRESHFVSARPQSQSPSSPEKEDQEEENQGGKGPLLSILKAFN"
                (SEQ ID NO:4)
    3'UTR       1848 . . . 1949
    polyA_      1949
    site
      site
BASE COUNT  599 a   455 c   517 g   378 t
ORIGIN
Arqarah         Length: 1949  1996 16:44  Type: N  Check: 6409 . . .
           1    CAATGAGAGG GAGGGTTTCT CCACTGATGC TGTTGCCTGG GATCCTTGTC
          51    CTGGCTTCAG TTTCTGCAAC GCAGGCCAAG TCACCTTACC GGAAAACAGA
         101    GAACCCCTGC GCCCAGAGGT GCCTCCAGAG TTGTCAACAG GAACCGGACG
         151    ACTTGAAGCA AAAGGCATGC GAGTCTCGCT GCACCAAGCT CGAGTATGAT
         201    CCTCGTTGTG TCTATGACAC TGGCGCCACC AACCAACGTC ACCCTCCAGG
         251    GGAGCGGACA CGTGGCCGCC AACCCGGAGA CTACGATGAT GACCGCCGTC
         301    AACCCCGAAG AGAGGAAGGA GGCCGATGGG GACCAGCTGA ACCGAGGGAG
         351    CGTGAAAGAG AAGAAGACTG GAGACAACCA AGAGAAGATT GGAGGCGACC
         401    AAGTCATCAG CAGCCACGGA AAATAAGGCC CGAAGGAAGA GAAGGAGAAC
         451    AAGAGTGGGG AACACCAGGT AGCGAGGTGA GGAAGAAAC ATCACGGAAC
         501    AACCCTTTCT ACTTCCCGTC AAGGCGGTTT AGCACCCGCT ACGGGAACCA
         551    AAACGGTAGG ATCCGCGTCC TGCAGAGGTT TGACCSSSGG TCAAAGCAGT
         601    TTCAGAATCT CCAGAATCAC CGTATTGTGC AGATCGAGGC CAGACCTAAC
         651    ACTCTTGTTC TTCCCAAGCA CGCTGATGCT GATAACATCC TTGTTATCCA
         701    GCAAGGACAA GCCACCGTGA CCCTAGCAAA TGGCAATAAC AGAAAGAGCT
         751    TTAATCTTGA CGAGGGCCAT GCACTCAGAA TCCCATCCGG TTTCATTTCC
         801    TACATCTTGA ATCGACATGA CAACCAGAAC CTCAGAGTAG CTAAAATCTC
         851    CATGCCCGTT AACACGCCCG GCCAGTTTGA GGATTTCTTC CCGGCGAGCA
         901    GCCGAGACCA ATCATCCTAC TTGCAGGGAT TCAGCAGGAA TACTTTGGAG
         951    GCCGCCTTCA ATGCGGAATT CAATGAGATA CGGAGGGTGC TGTTAGAAGA
        1001    GAATGCAGGA GGAGAGCAAG AGGAGAGAGG GCAGAGGCGA CGGAGTACTC
        1051    GGAGTAGTGA TAATGAAGGA GTGATAGTCA AAGTGTCAAA GGAGCACGTT
        1101    CAAGAACTTA CTAAGCACGC TAAATCCGTC TCAAAGAAAG GCTCCGAAGA
        1151    GGAAGATATC ACCAACCCAA TCAACTTGAG AGATGGCGAG CCCGATCTTT
        1201    CTAACAACTT TGGGAGGTTA TTTGAGGTGA AGCCAGACGA GAAGAACCCC
        1251    CAGCTTCAGG ACCTGGACAT GATGCTCACC TGTGTAGAGA TCAAAGAAGG
        1301    AGCTTTGATG CTCCCACACT TCAACTCAAA GGCCATGGTC ATCGTCGTCG
        1351    TCAACAAAGG AACTGGAAAC CTTGAACTCG TAGCTGTAAG AAAAGAGCAA
        1401    CAACAGAGGG GACGGCGGGA ACAAGAGTGG GAAGAAGAGG AGGAAGATGA
        1451    AGAAGAGGAG GGAAGTAACA GAGAGGTGCG TAGGTACACA GCGAGGTTGA
        1501    AGGAAGGCGA TGTGTTCATC ATGCCAGCAG CTCATCCAGT AGCCATCAAC
        1551    GCTTCCTCCG AACTCCATCT GCTTGGCTTC GGTATCAACG CTGAAAACAA
        1601    CCACAGAATC TTCCTTGCAG GTGATAAGGA CAATGTGATA GACCAGATAG
        1651    AGAAGCAAGC GAAGGATTTA GCATTCCCTG GTTCGGGTGA ACAAGTTGAG
        1701    AAGCTCATCA AAAACCAGAG GGAGTCCTCA CTTTGTGAGTG CTCGTCCTCA
        1751    ATCTCAATCT CCGTCGTCTC CTGAAAAAGA GGATCAAGAG GAGGAAAACC
        1801    AAGGAGGGAA GGGTCCACTC CTTTCAATTT TGAAGGCTTT TAACTGAGAA
        1851    TGGAGGAAAC TTGTTATGTA TCCATAATAA GATCACGCTT TTGTAATCTA
        1901    CTATCCAAAA ACTTATCAAT AAATAAAAAC GTTTGTGCGT TGTTTCTCC
                (SEQ ID NO:19)
```

TABLE 18

| | | | | |
|---|---|---|---|---|
| LOCUS | ARQALLII | 717 bp | DNA | PLN |
| DEFINITION | *Arachis hypogea* (clone Ara h II p38) allergen II gene, polyA signal. | | | |
| ACCESSION | L77197 | | | |
| NID | g1236995 | | | |
| KEYWORDS | allergen; conglutin; seed storage protein. | | | |
| SOURCE | *Arachis hypogea* (strain Florunner) (clone: Ara h II p38) DNA. | | | |
| ORGANISM | *Arachis hypogaea* | | | |
| | Eukaryotae; *mitochondrial eukaryotes*; | | | |

TABLE 18-continued

|  |  |
|---|---|
|  | Viridiplantae; Charophyta/Embryophyta group; Embryophyta; Magnoliophyta; Magnoliopsida; Rutanae; Sapindales; Fabaceae; Papilionoideae; Arachis. |
| REFERENCE | 1 (bases 1 to 717) |
| AUTHORS | Stanley, J. S. |
| TITLE | The major peanut allergen Ara h II is a seed storage protein with multiple IgE-binding epitopes |
| JOURNAL | Unpublished (1996) |
| FEATURES | Location/Qualifiers |
| source | 1 . . . 717 |
|  | /organism = "Arachis hypogaea" |
|  | /strain = "Florunner" |
|  | /clone = "Ara h II p38" |
| polyA_signal | 562 . . . 567 |
| BASE COUNT | 217 a   152 c   184 g   164 t |
| ORIGIN |  |
| Arqallii | Length: 717     1996 14:32 Type: N Check: 3606 . . . |

```
  1 GCTCACCATA CTAGTAGCCC TCGCCCTTTT CCTCCTCGCT GCCCACGCAT
 51 CTGCGAGGCA GCAGTGGGAA CTCCAAGGAG ACAGAAGATG CCAGAGCCAG
101 CTCGAGAGGG CGAACCTGAG GCCCTGCGAG CAACATCTCA TGCAGAAGAT
151 CCAACGTGAC GAGGATTCAT ATGAACGGGA CCCGTACAGC CCTAGTCAGG
201 ATCCGTACAG CCCTAGTCCA TATGATCGGA GAGGCGCTGG ATCCTCTCAG
251 CACCAAGAGA GGTGTTGCAA TGAGCTGAAC GAGTTTGAGA ACAACCAAAG
301 GTGCATGTGC GAGGCATTGC AACAGATCAT GGAGAACCAG AGCGATAGGT
351 TGCAGGGGAG GCAACAGGAG CAACAGTTCA AGAGGGAGCT CAGGAACTTG
401 CCTCAACAGT GCGGCCTTAG GCACCACAG CGTTGCGACT TGGACGTCGA
451 AAGTGGCGGC AGAGACAGAT ACTAAACACC TATCTCAAAA AAAGAAAAGA
501 AAAGAAAAGA AAATAGCTTA TATATAAGCT ATTATCTATG GTTATGTTTA
551 GTTTTGGTAA TAATAAAGAT CATCACTATA TGAATGTGTT GATCGTGTTA
601 ACTAAGGCAA GCTTAGGTTA TATGAGCACC TTTAGAGTGC TTTTATGGCG
651 TTGTCTATGT TTTGTTGCTG CAGAGTTGTA ACCATCTTGA AATAATATAA
701 AAAGATCATG TTTTGTT (SEQ ID NO:20)
```

TABLE 19

|  |  |
|---|---|
| LOCUS | ARQARAHI    2032 bp    mRNA                              PLN |
| DEFINITION | *Arachis hypogea* (clone P41b) Ara h I mRNA, complete cds. |
| ACCESSION | L34402 |
| NID | g602435 |
| KEYWORDS | allergen |
| SOURCE | *Arachis hypogea* (strain Florunner) seed CDNA to mRNA. |
| ORGANISM | *Arachis hypogaea* |
|  | Eukaryota; Plantae; Embryobionta; Magnoliophyta; Magnoliopsida; Rosidae; Fabales; Fabaceae. |
| REFERENCE | 1 (bases 1 to 2032) |
| AUTHORS | Burks,A.W., Cockrell,G., Stanley,J.S., Helm,R.M. and Bannon, G.A. |
| TITLE | Recombinant peanut allergen Ara h I expression and IgE binding in patients with peanut hypersensitivity |
| JOURNAL | Unpublished (1994) |
| COMMENT | NCBI gi: 602435 |
| FEATURES | Location Qualifiers |
| Source | 1. . 2032 |
|  | /Organism = "Arachis hypogea" |
|  | /strain = "Florunner" |
|  | /dev_stage = "seed" |
|  | /sequenced_mol = "CDNA to mRNA" |
|  | /clone = "P41b" |
| 5'UTR | <1. . . 49 |
| CDS | 50. . .1930 |
|  | /gene = "Ara h I" |
|  | /note = "NCBI gi: 602436" |
|  | /codon_start = 1 |
|  | /db xref = "PID:g602436" |
|  | /translation = "MRGRVSPLMLLLGILVLASVSATHAKSSPYQKKTENPCAQRCLQ SCQQEFDDLKQKACESRCTKLEYD-PRCVYDPRGHTGTINQRSPPGERTRGRQPGDYDD DRRQPRREEGGRWGPAGPREREREED-WRQPREDWRRPSHQQPRKIRPEGREGEQEWGT PGSHVREETSRNNPFYFPSRRFSTRYGN-QNGRIRVLQRFDQRSRQFQNLQNHRIVQIE AKPNTLVLPKHADADNILVIQQGQATVT-VANGNNRKSFNLDEGEALRIPSGFISYILN |

TABLE 19-continued

```
                   RHDNQNLRVAKISMPVNTPGQFEDFF-
          PASSRDQSSYLQGFSRNTLEAAFNAEFNEIRR
                    VLLEENAGGEQEERGQRRWSTRSSEN-
          NEGVIVKVSKEHVEELTKHAKSVSKKGSEEEG
                    DITNPINLREGEPDLSNNFGKLFEVKPD-
          KKNPQLQDLDMMLTCVEIKEGALMLPHFNS
                    KAMVIVVVNKGTGNLELVAVRKEQQQR-
          GRREEEEDEDEEEEGSNREVRRYTARLKEGD
                    VFIMPAAHPVAINASSELHLLGFGI-
          NAENHHRIFLAGDKDNVIDQIEKQAKDLAFPGS
                    GEQVEKLIKNQKESHFVSAR-
          PQSQSQSPSSPEKESPEKEDQEEENQGGKGPLLSILKA
                    FN"(SEQ ID NO:4)
3'UTR         1931 . . . 2032
polyA_signal  2005 . . . 2010
PolyA_site    2032
BASE COUNT    628 a   473 c   530 g   401 t
ORIGIN
      Arqarani   Length: 2032   1996 16:36   Type: N Check: 8370 . . .
          1      AATAATCATA TATATTCATC AATCATCTAT ATAAGTAGTA GCAGGAGCAA
         51      TGAGAGGGAG GGTTTCTCCA CTGATGCTGT TGCTAGGGAT CCTTGTCCTG
        101      GCTTCAGTTT CTGCAACGCA TGCCAAGTCA TCACCTTACC AGAAGAAAAC
        151      AGAGAACCCC TGCGCCCAGA GGTGCCTCCA GAGTTGTCAA CAGGAACCGG
        201      ATGACTTGAA GCAAAAGGCA TGCGAGTCTC GCTGCACCAA GCTCGAGTAT
        251      GATCCTCGTT GTGTCTATGA TCCTCGAGGA CACACTGGCA CCACCAACCA
        301      ACGTTCCCCT CCAGGGGAGC GGACACCTGC CCGCCAACCC GGAGACTACG
        351      ATGATGACCG CCGTCAACCC CGAAGAGAGG AAGGAGGCCG ATGGGGACCA
        401      GCTGGACCGA GGGAGCGTGA AAGAGAAGAA GACTGGAGAC AACCAAGAGA
        451      AGATTGGAGG CGACCAAGTC ATCAGCAGCC ACGGAAAATA AGGCCCGAGA
        501      GAAGAGAAGG AGAACAAGAG TGGGGAACAC CAGGTAGCCA TGTGAGGGAA
        551      GAAACATCTC GGAACAACCC TTTCTACTTC CCGTCAAGGC GGTTTAGCAC
        601      CCGCTACGGG AACCAAAACG GTAGGATCCG GGTCCTGCAG AGGTTTGACC
        651      AAAGGTCAAG GCAGTTTCAG AATCCCAGA ATCACCGTAT TGTGCAGATC
        701      GAGGCCAAAC CTAACACTCT TGTTCTTCCC AAGCACGCTG ATGCTGATAA
        751      CATCCTTGTT ATCCAGCAAG GGCAAGCCAC CGTGACCGTA GCAAATGGCA
        801      ATAACAGAAA GAGCTTTAAT CTTGACGAGG GCCATGCACT CAGAATCCCA
        851      TCCGGTTTCA TTTCCTACAT CTTGAACCGC CATGACAACC AGAACCTCAG
        901      AGTAGCTAAA ATCTCCATGC CCGTTAACAC ACCCGGCCAG TTTGAGGATT
        951      TCTTCCCGGC GAGCAGCCGA GACCAATCAT CCTACTTGCA GGGCTTCAGC
       1001      AGGAATACGT TGGACGCCGC CTTCAATGCG GAATTCAATG AGATACGGAG
       1051      GGTGCTGTTA GAAGAGAATG CAGGAGGTGA GCAAGAGGAG AGGCCCGAGA
       1101      GGCGATGGAG TACTCGGAGT AGTGAGAACA ATGAAGGAGT GATAGTCAAA
       1151      GTGTCAAAGG AGCACGTTGA AGAACTTACT AAGCACGCTA AATCCGTCTC
       1201      AAAGAAAGGC TCCGAAGAAG AGGGAGATAT CACCAACCCA ATCAACTTGA
       1251      GAGAAGGCGA GCCCGATCTT TCTAACAACT TTGGGAAGTT ATTTGAGGTG
       1301      AAGCCAGACA AGAAGAACCC CCAGCTTCAG GACCTGGACA TGATGCTCAC
       1351      CTGTGTAGAG ATCAAAGAAG GAGCTTTGAT GCTCCCACAC TTCAACTCAA
       1401      AGGCCATGGT TATCGTCGTC GTCAACAAAG GAACTGGAAA CCTTGAACTC
       1451      GTGGCTGTAA GAAAAGAGCA ACAACAGAGG GGACGGCGGG AAGAAGAGGA
       1501      GGACGAAGAC GAAGAAGAGG AGGGAAGTAA CAGAGAGGTG CGTAGGTACA
       1551      CAGCGAGGTT GAAGGAAGGC GATGTGTTCA TCATGCCAGC AGCTCATCCA
       1601      GTAGCCATCA ACGCTTCCTC CGAAGTCCAT CTGCTTGGCT TCGGTATCAA
       1651      CGCTGAAAAC AACCACAGAA TCTTCCTTGC AGGTGATAAG GACAATGTGA
       1701      TAGACCAGAT AGAGAAGCAA GCGAAGGATT TAGCATTCCC TGGGTCGGGT
       1751      GAACAAGTTG AGAAGCTCAT CAAAAACCAG AAGGAATCTC ACTTTGTGAG
       1801      TGCTCGTCCT CAATCTCAAT CTCAATCTCC GTCGTCTCCT GAGAAAGAGT
       1851      CTCCTGAGAA AGAGGATCAA GAGGAGGAAA ACCAAGGAGG GAAGGGTCCA
       1901      CTCCTTTCAA TTTTGAAGGC TTTTAACTGA GAATGGAGGC AACTTGTTAT
       1951      GTATCGATAA TAAGATCACG CTTTTGTACT CTACTATCCA AAAACTTATC
       2001      AATAAATAAA AACGTTTGTG CGTTGTTTCT CC (SEQ ID NO:21)
```

TABLE 20

```
GENIE> type arah2p38.pep
TRANSLATE of: arah2p38.final check: 9822 from: 4 to: 460
generated symbols 1 to: 159.
Arah2p3a.Pep Length: 157   1996 15:24   Type: P Check: 2859 . . .
    1  LTILVALALF LLAAHASARQ QWELQGDRRC QSQLERANLF PCEQHLMQKI
   51  QRDEDSYERD PYSPSQDPYS PSPYDRRGAG SSQHQERCCN ELNEFENNQR
  101  CMCEALQQIM ENQSDRLQGR QQEQQFKREL RNLPQQCGLR APQRCDLDVE
  151  SGGRDRY (SEQ ID NO:22)
```

What is claimed is:

1. An isolated nucleotide molecule encoding the peanut allergen designated Ara h II hybridizing under standard conditions to SEQ ID NO: 1 and which encodes a protein binding to anti-Ara h II antibodies obtained from patients with peanut allergies.

2. The nucleotide molecule of claim 1 encoding the full length protein.

3. The isolated nucleotide molecule of claim 1 having the sequence shown in Seq ID No. 1.

4. The isolated nucleotide molecule of claim 1 inserted into a vector for expression in an appropriate host.

5. The isolated nucleotide molecule of claim 3 inserted into a vector for expression in an appropriate host.

6. The isolated nucleotide molecule of claim 4 or 5 wherein the host is a bacteria.

7. The nucleotide molecule of claim 1 wherein the peanut allergen comprises one or more mutated IgE epitopes.

8. The nucleotide molecule of claim 7 wherein the IgE epitope is shown in SEQ ID NO: 2.

* * * * *

SEQUENCE LISTING

<160> NUMBER OF SEQ ID NOS: 23

<210> SEQ ID NO 1
<211> LENGTH: 743
<212> TYPE: DNA
<213> ORGANISM: Arachis hypogaea

<400> SEQUENCE: 1

```
acgaggctca ccatactagt agccctcgcc cttttcctcc tcgtcgccca cgcatctgcg      60
aggcagcagt gggaactcca aggagacaga agatgccaga gccagctcga gagggcgaac     120
ctgaggccct gcgagcaaca tctcatgcag aagatccaac gtgacgagga ttcatatgaa     180
cgggacccgt acagccctag tcaggatccg tacagcccta gtccatatga tcggagaggc     240
gctggatcct ctcagcacca agagaggtgt tgcaatgagc tgaacgagtt tgagaacaac     300
caaaggtgca tgtgcgaggc attgcaacag atcatggaga accagagcga taggttgcag     360
gggaggcaac aggagcaaca gttcaaggag gagctcagga acttgcctca acagtgcggc     420
cttagggcac cacagcgttg cgacttggac gtcgaaagtg gcggcagaga cagatactaa     480
acacctatct caaaaaaaga aagaaaaga aagaaaata gcttatatat aagctattat      540
ctatggttat gtttagtttt ggtaataata aagatcatca ctatatgaat gtgttgatcg     600
tgttaactaa ggcaagctta ggttatatga gcacctttag agtgctttta tggcgttgtc     660
tatgttttgt tgctgcagag ttgtaaccat cttgaaataa tataaaaaga tcatgttttg     720
ttaaaaaaaa aaaaaaaaaa aaa                                             743
```

<210> SEQ ID NO 2
<211> LENGTH: 159
<212> TYPE: PRT
<213> ORGANISM: Arachis hypogaea
<220> FEATURE:
<223> OTHER INFORMATION: Amino Acids 17-26 are Ara H 2 Binding Epitopes, Peptide 1
<223> OTHER INFORMATION: Amino Acids 23-32 are Ara H 2 binding epitopes, peptide 2
<223> OTHER INFORMATION: Amino Acids 29-38 are Ara H 2 binding epitopes, peptide 3
<223> OTHER INFORMATION: Amino Acids 41-50 are Ara H 2 binding epitopes, peptide 4
<223> OTHER INFORMATION: Amino Acids 51-60 are Ara H 2 binding epitopes, peptide 5
<223> OTHER INFORMATION: Amino Acids 59-68 are Ara H 2 binding epitopes, peptide 6
<223> OTHER INFORMATION: Amino Acids 67-76 are Ara H 2 binding epitopes, peptide 7
<223> OTHER INFORMATION: Amino Acids 117-126 are Ara H 2 binding epitopes, peptide 8
<223> OTHER INFORMATION: Amino Acids 129-138 are Ara H 2 binding epitopes, peptide 9
<223> OTHER INFORMATION: Amino Acids 145-154 are Ara H 2 binding epitopes, peptide 10
<223> OTHER INFORMATION: Amino Acids 13-22 are Ara H 2 binding epitopes, peptide 1, Table 12
<223> OTHER INFORMATION: Amino Acids 27-36 are Ara H 2 binding epitopes, peptide 2, Table 12
<223> OTHER INFORMATION: Amino Acids 59-68 are Ara H 2 binding epitopes, peptide 3, Table 12
<223> OTHER INFORMATION: Amino Acids 81-90 are Ara H 2 binding epitopes, peptide 4, Table 12
<223> OTHER INFORMATION: Amino Acids 91-100 are Ara H 2 binding epitopes, peptide 5, Table 12
<223> OTHER INFORMATION: Amino Acids 145-154 are Ara H 2 binding epitopes, peptide 6, Table 12

<400> SEQUENCE: 2

-continued

```
Thr Arg Leu Thr Ile Leu Val Ala Leu Ala Leu Phe Leu Leu Ala Ala
 1               5                  10                  15

His Ala Ser Ala Arg Gln Gln Trp Glu Leu Gln Gly Asp Arg Arg Cys
             20                  25                  30

Gln Ser Gln Leu Glu Arg Ala Asn Leu Arg Pro Cys Glu Gln His Leu
         35                  40                  45

Met Gln Lys Ile Gln Arg Asp Glu Asp Ser Tyr Glu Arg Asp Pro Tyr
     50                  55                  60

Ser Pro Ser Gln Asp Pro Tyr Ser Pro Ser Pro Tyr Asp Arg Arg Gly
 65                  70                  75                  80

Ala Gly Ser Ser Gln His Gln Glu Arg Cys Cys Asn Glu Leu Asn Glu
                 85                  90                  95

Phe Glu Asn Asn Gln Arg Cys Met Cys Glu Ala Leu Gln Gln Ile Met
             100                 105                 110

Glu Asn Gln Ser Asp Arg Leu Gln Gly Arg Gln Glu Gln Gln Phe
         115                 120                 125

Lys Arg Glu Leu Arg Asn Leu Pro Gln Gln Cys Gly Leu Arg Ala Pro
     130                 135                 140

Gln Arg Cys Asp Leu Asp Val Glu Ser Gly Gly Arg Asp Arg Tyr
145                 150                 155
```

<210> SEQ ID NO 3
<211> LENGTH: 1930
<212> TYPE: DNA
<213> ORGANISM: Arachis hypogaea

<400> SEQUENCE: 3

```
aataatcata tatattcatc aatcatctat ataagtagta gcaggagcaa tgagagggag     60
ggtttctcca ctgatgctgt tgctagggat ccttgtcctg gcttcagttt ctgcaacgca    120
tgccaagtca tcaccttacc agaagaaaac agagaacccc tgcgcccaga ggtgcctcca    180
gagttgtcaa caggaaccgg atgacttgaa gcaaaaggca tgcgagtctc gctgcaccaa    240
gctcgagtat gatcctcgtt gtgtctatga tcctcgagga cacactggca ccaccaacca    300
acgttcccct ccaggggagc ggacacgtgg ccgccaaccc ggagactacg atgatgaccg    360
ccgtcaaccc cgaagagagg aaggaggccg atgggaccga ctggaccgag ggagcgtgaa   420
agagaagaa gactggagac aaccaagaga agattggagg cgaccaagtc atcagcagcc    480
acggaaaata aggcccgaag gaagagaagg agaacaagag tggggaacac aggtagcca    540
tgtgagggaa gaaacatctc ggaacaaccc tttctacttc ccgtcaaggc ggtttagcac    600
ccgctacggg aaccaaaacg gtaggatccg ggtcctgcag aggtttgacc aaaggtcaag    660
gcagtttcag aatctccaga atcaccgtat tgtgcagatc gaggccaaac ctaacactct    720
tgttcttccc aagcacgctg atgctgataa catccttgtt atccagcaag gcaagccac    780
cgtgaccgta gcaaatggca ataacagaaa gagctttaat cttgacgagg ccatgcact     840
cagaatccca tccggtttca tttcctacat cttgaaccgc catgacaacc agaacctcag    900
agtagctaaa atctccatgc ccgttaacac acccggccag tttgaggatt cttcccggc     960
gagcagccga gaccaatcat cctacttgca gggcttcagc aggaatacgt tggaggccgc   1020
cttcaatgcg gaattcaatg agatacggag ggtgctgtta gaagagaatg caggaggtga   1080
gcaagaggag agaggcaga ggcgatggag tactcggagt agtgagaaca atgaaggagt    1140
gatagtcaaa gtgtcaaagg agcacgttga agaacttact aagcacgcta aatccgtctc   1200
aaagaaaggc tccgaagaag agggagatat caccaaccca atcaacttga gagaaggcga   1260
```

```
gcccgatctt tctaacaact ttgggaagtt atttgaggtg aagccagaca agaagaaccc   1320
ccagcttcag gacctggaca tgatgctcac ctgtgtagag atcaaagaag gagctttgat   1380
gctcccacac ttcaactcaa aggccatggt tatcgtcgtc gtcaacaaag gaactggaaa   1440
ccttgaactc gtggctgtaa gaaaagagca acaacagagg ggacggcggg aagaagagga   1500
ggacgaagac gaagaagagg agggaagtaa cagagaggtc cgtaggtaca cagcgaggtt   1560
gaaggaaggc gatgtgttca tcatgccagc agctcatcca gtagccatca acgcttcctc   1620
cgaactccat ctgcttggct tcggtatcaa cgctgaaaac aaccacagaa tcttccttgc   1680
aggtgataag gacaatgtga tagaccagat agagaagcaa gcgaaggatt tagcattccc   1740
tgggtcgggt gaacaagttg agaagctcat caaaaaccag aaggaatctc actttgtgag   1800
tgctcgtcct caatctcaat ctcaatctcc gtcgtctcct gagaaagagt ctcctgagaa   1860
agaggatcaa gaggaggaaa accaaggagg gaagggtcca ctcctttcaa ttttgaaggc   1920
ttttaactga                                                         1930

<210> SEQ ID NO 4
<211> LENGTH: 626
<212> TYPE: PRT
<213> ORGANISM: Arachis hypogaea
<220> FEATURE:
<223> OTHER INFORMATION: Amino Acids 25-34 are Ara H 1 binding epitope,
      peptide 1
<223> OTHER INFORMATION: Amino Acids 48-57 are Ara H 1 binding epitope,
      peptide 2
<223> OTHER INFORMATION: Amino Acids 65-74 are Ara H 1 binding epitope,
      peptide 3
<223> OTHER INFORMATION: Amino Acids 89-98 are Ara H 1 binding epitope,
      peptide 4
<223> OTHER INFORMATION: Amino Acids 97-106 are Ara H 1 binding epitope,
      peptide 5
<223> OTHER INFORMATION: Amino Acids 107-116 are Ara H 1 binding
      epitope, peptide 6
<223> OTHER INFORMATION: Amino Acids 123-132 are Ara H 1 binding
      epitope, peptide 7
<223> OTHER INFORMATION: Amino Acids 134-143 are Ara H 1 binding
      epitope, peptide 8
<223> OTHER INFORMATION: Amino Acids 143-152 are Ara H 1 binding
      epitope, peptide 9
<223> OTHER INFORMATION: Amino Acids 294-303 are Ara H 1 binding
      epitope, peptide 10
<223> OTHER INFORMATION: Amino Acids 311-320 are Ara H 1 binding
      epitope, peptide 11
<223> OTHER INFORMATION: Amino Acids 325-334 are Ara H 1 binding
      epitope, peptide 12
<223> OTHER INFORMATION: Amino Acids 344-353 are Ara H 1 binding
      epitope, peptide 13
<223> OTHER INFORMATION: Amino Acids 393-402 are Ara H 1 binding
      epitope, peptide 14
<223> OTHER INFORMATION: Amino Acids 409-418 are Ara H 1 binding
      epitope, peptide 15
<223> OTHER INFORMATION: Amino Acids 461-470 are Ara H 1 binding
      epitope, peptide 16
<223> OTHER INFORMATION: Amino Acids 498-507 are Ara H 1 binding
      epitope, peptide 17
<223> OTHER INFORMATION: Amino Acids 525-534 are Ara H 1 binding
      epitope, peptide 18
<223> OTHER INFORMATION: Amino acids 539-548 are Ara H 1 binding
      epitope, peptide 19
<223> OTHER INFORMATION: Amino acids 551-560 are Ara H 1 binding
      epitope, peptide 20
<223> OTHER INFORMATION: Amino acids 559-568 are Ara H 1 binding
      epitope, peptide 21
<223> OTHER INFORMATION: Amino acids 578-587 are Ara H 1 binding
      epitope, peptide 22
<223> OTHER INFORMATION: Amino acids 597-606 are Ara H 1 binding
      epitope, peptide 23

<400> SEQUENCE: 4
```

-continued

```
Met Arg Gly Arg Val Ser Pro Leu Met Leu Leu Gly Ile Leu Val
 1               5                  10                  15

Leu Ala Ser Val Ser Ala Thr His Ala Lys Ser Ser Pro Tyr Gln Lys
            20                  25                  30

Lys Thr Glu Asn Pro Cys Ala Gln Arg Cys Leu Gln Ser Cys Gln Gln
        35                  40                  45

Glu Pro Asp Asp Leu Lys Gln Lys Ala Cys Glu Ser Arg Cys Thr Lys
    50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Arg Arg Gln Pro Arg Arg Glu Glu Gly
                100                 105                 110

Gly Arg Trp Gly Pro Ala Gly Pro Arg Glu Arg Glu Arg Glu Glu Asp
            115                 120                 125

Trp Arg Gln Pro Arg Glu Asp Trp Arg Arg Pro Ser His Gln Gln Pro
    130                 135                 140

Arg Lys Ile Arg Pro Glu Gly Arg Glu Gly Glu Gln Glu Trp Gly Thr
145                 150                 155                 160

Pro Gly Ser His Val Arg Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
            195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
        275                 280                 285

Ser Met Pro Val Asn Thr Pro Gly Gln Phe Glu Asp Phe Phe Pro Ala
    290                 295                 300

Ser Ser Arg Asp Gln Ser Ser Tyr Leu Gln Glu Phe Ser Arg Asn Thr
305                 310                 315                 320

Leu Glu Ala Ala Phe Asn Ala Glu Phe Asn Glu Ile Arg Arg Val Leu
            325                 330                 335

Leu Glu Glu Asn Ala Gly Gly Glu Gln Glu Glu Arg Gly Gln Arg Arg
            340                 345                 350

Trp Ser Thr Arg Ser Ser Glu Asn Asn Glu Gly Val Ile Val Lys Val
        355                 360                 365

Ser Lys Glu His Val Glu Glu Leu Thr Lys His Ala Lys Ser Val Ser
    370                 375                 380

Lys Lys Gly Ser Glu Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415
```

-continued

```
Val Lys Pro Asp Lys Lys Asn Pro Gln Leu Gln Asp Leu Asp Met Met
            420                 425                 430

Leu Thr Cys Val Glu Ile Lys Glu Gly Ala Leu Met Leu Pro His Phe
        435                 440                 445

Asn Ser Lys Ala Met Val Ile Val Val Asn Lys Gly Thr Gly Asn
    450                 455                 460

Leu Glu Leu Val Ala Val Arg Lys Glu Gln Gln Gln Arg Gly Arg Arg
465                 470                 475                 480

Glu Glu Glu Glu Asp Glu Asp Glu Glu Glu Gly Ser Asn Arg Glu
                485                 490                 495

Val Arg Arg Tyr Thr Ala Arg Leu Lys Glu Gly Asp Val Phe Ile Met
                500                 505                 510

Pro Ala Ala His Pro Val Ala Ile Asn Ala Ser Ser Glu Leu His Leu
                515                 520                 525

Leu Gly Phe Gly Ile Asn Ala Glu Asn Asn His Arg Ile Phe Leu Ala
            530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
            580                 585                 590

Ser Pro Ser Ser Pro Glu Lys Glu Ser Pro Lys Glu Asp Gln Glu
            595                 600                 605

Glu Glu Asn Gln Gly Gly Lys Gly Pro Leu Leu Ser Ile Leu Lys Ala
    610                 615                 620

Phe Asn
625

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide
<223> OTHER INFORMATION: N at position 19 is either A, G, C, or T

<400> SEQUENCE: 5
gatcaaagga tcaatcgtna ttcagatcca                                        30

<210> SEQ ID NO 6
<211> LENGTH: 10
<212> TYPE: PRT
<213> ORGANISM: Soy

<400> SEQUENCE: 6

Phe Pro Arg Pro Gln Pro Arg Gln Glu Glu
  1               5                  10

<210> SEQ ID NO 7
<211> LENGTH: 10
<212> TYPE: PRT
<213> ORGANISM: Soy

<400> SEQUENCE: 7

Arg Lys Tyr Arg Ala Glu Leu Ser Glu Gln
  1               5                  10
```

```
<210> SEQ ID NO 8
<211> LENGTH: 9
<212> TYPE: PRT
<213> ORGANISM: Cacao

<400> SEQUENCE: 8

Glu Gln Cys Glu Gln Arg Cys Glu Arg
 1               5

<210> SEQ ID NO 9
<211> LENGTH: 10
<212> TYPE: PRT
<213> ORGANISM: Jack Bean

<400> SEQUENCE: 9

Arg Arg Tyr Ala Ala Thr Leu Ser Glu Gly
 1               5                  10

<210> SEQ ID NO 10
<211> LENGTH: 10
<212> TYPE: PRT
<213> ORGANISM: Pea

<400> SEQUENCE: 10

Glu Glu His Glu Glu Glu Lys Gln Lys Tyr
 1               5                  10

<210> SEQ ID NO 11
<211> LENGTH: 10
<212> TYPE: PRT
<213> ORGANISM: Pea

<400> SEQUENCE: 11

Gln Arg Tyr Glu Ala Arg Leu Ala Asp Gly
 1               5                  10

<210> SEQ ID NO 12
<211> LENGTH: 10
<212> TYPE: PRT
<213> ORGANISM: Maize

<400> SEQUENCE: 12

Trp Glu Asp Asp Asn His His His His His
 1               5                  10

<210> SEQ ID NO 13
<211> LENGTH: 10
<212> TYPE: PRT
<213> ORGANISM: Fava Bean

<400> SEQUENCE: 13

Gln Asn Tyr Lys Ala Lys Leu Ser Pro Gly
 1               5                  10

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide
<223> OTHER INFORMATION: N at position 26 is either A, G, C, or T

<400> SEQUENCE: 14
caagcaagtg ggaagttagc aagggngatc ag                              32
```

```
<210> SEQ ID NO 15
<211> LENGTH: 18
<212> TYPE: PRT
<213> ORGANISM: Arachis hypogaea
<220> FEATURE:
<223> OTHER INFORMATION: Xaa at position 1 could be any amino acid.

<400> SEQUENCE: 15

Xaa Gln Gln Trp Glu Leu Gln Gly Asp Arg Arg Gln Ser Gln Leu
 1               5                  10                  15

Glu Arg

<210> SEQ ID NO 16
<211> LENGTH: 30
<212> TYPE: PRT
<213> ORGANISM: Arachis hypogaea
<220> FEATURE:
<223> OTHER INFORMATION: Xaa at positions 22, 24, 27, and 30 are any of
      the amino acids.

<400> SEQUENCE: 16

Gly Gln Gln Trp Glu Leu Gln Gly Asp Arg Arg Gln Ser Gln Leu
 1               5                  10                  15

Glu Arg Ala Asn Leu Xaa Pro Xaa Glu Gln Xaa Leu Met Xaa
                20                  25                  30

<210> SEQ ID NO 17
<211> LENGTH: 335
<212> TYPE: PRT
<213> ORGANISM: Arachis hypogaea

<400> SEQUENCE: 17

Met Pro Val Asn Thr Pro Gly Gln Phe Glu Asp Phe Pro Ala Ser
 1               5                  10                  15

Ser Arg Asp Gln Ser Ser Tyr Leu Gln Gly Phe Ser Arg Asn Thr Leu
                20                  25                  30

Glu Ala Ala Phe Asn Ala Glu Phe Asn Glu Ile Arg Arg Val Leu Leu
            35                  40                  45

Glu Glu Asn Ala Gly Gly Glu Gln Glu Glu Arg Gly Gln Arg Trp
         50                  55                  60

Ser Thr Arg Ser Ser Glu Asn Asn Glu Gly Val Ile Val Lys Val Ser
 65                  70                  75                  80

Lys Glu His Val Glu Glu Leu Thr Lys His Ala Lys Ser Val Ser Lys
                85                  90                  95

Lys Gly Ser Glu Glu Glu Gly Asp Ile Thr Asn Pro Ile Asn Leu Arg
            100                 105                 110

Glu Gly Glu Pro Asp Leu Ser Asn Asn Phe Gly Lys Leu Phe Glu Val
        115                 120                 125

Lys Pro Asp Lys Lys Asn Pro Gln Leu Gln Asp Leu Asp Met Met Leu
    130                 135                 140

Thr Cys Val Glu Ile Lys Glu Gly Ala Leu Met Leu Pro His Phe Asn
145                 150                 155                 160

Ser Lys Ala Met Val Ile Val Val Asn Lys Gly Thr Gly Asn Leu
                165                 170                 175

Glu Leu Val Ala Val Arg Lys Glu Gln Gln Gln Arg Gly Arg Arg Glu
            180                 185                 190

Glu Glu Glu Asp Glu Asp Glu Glu Glu Gly Ser Asn Arg Glu Val
        195                 200                 205
```

```
Arg Arg Tyr Thr Ala Arg Leu Lys Glu Gly Asp Val Phe Ile Met Pro
    210                 215                 220

Ala Ala His Pro Val Ala Ile Asn Ala Ser Ser Glu Leu His Leu Leu
225                 230                 235                 240

Gly Phe Gly Ile Asn Ala Glu Asn Asn His Arg Ile Phe Leu Ala Gly
                245                 250                 255

Asp Lys Asp Asn Val Ile Asp Gln Ile Glu Lys Gln Ala Lys Asp Leu
            260                 265                 270

Ala Phe Pro Gly Ser Gly Glu Gln Val Glu Lys Leu Ile Lys Asn Gln
        275                 280                 285

Lys Glu Ser His Phe Val Ser Ala Gln Ser Gln Ser Gln Ser Pro Ser
    290                 295                 300

Ser Pro Glu Lys Glu Ser Pro Glu Lys Glu Asp Gln Glu Glu Glu Asn
305                 310                 315                 320

Gln Gly Gly Lys Gly Pro Leu Leu Ser Ile Leu Lys Ala Phe Asn
                325                 330                 335

<210> SEQ ID NO 18
<211> LENGTH: 750
<212> TYPE: DNA
<213> ORGANISM: Arachis hypogaea

<400> SEQUENCE: 18
gtattgtgca gatcgaggcc aaacctaaca ctcttgttct tcccaagcac gctgatgctg      60
ataacatcct tgttatccag caagggcaag ccaccgtgac cgtagcaaat ggcaataaca     120
gaaagagctt taatcttgac gagggccatg cactcagaat cccatccggt ttcatttcct     180
acatcttgaa ccgccatgac aaccagaacc tcagagtagc taaaatctcc atgcccgtta     240
acacacccgg ccagtttgag gatttcttcc ggcgagcag ccgagaccaa tcatcctact     300
tgcagggctt cagcaggaat acgttggagg ccgccttcaa tgcggaattc aatgagatac     360
ggagggtgct gttagaagag aatgcaggag gtgagcaaga ggagagaggg cagaggcgat     420
ggagtactcg gagtagtgag aacaatgaag gagtgatagt caaagtgtca aggagcacg     480 ttgaagaact tactaagcac gctaaatccg tctcaaagaa aggctccgaa gagagggag     540 atatcaccaa cccaatcaac ttgagagaag gcgagcccga tctttctaac aactttggga     600
agttatttga ggtgaagcca gacaagaaga ccccccagct tcaggacctg acatgatgc     660 tcacctgtgt agagatcaaa gaaggagctt tgatgctccc acacttcaac tcaaaggcca     720
tggttatcgt cgtcgtcaac aaaggaactg                                      750

<210> SEQ ID NO 19
<211> LENGTH: 1949
<212> TYPE: DNA
<213> ORGANISM: Arachis hypogaea

<400> SEQUENCE: 19
caatgagagg gagggtttct ccactgatgc tgttgcttgg gatccttgtc ctggcttcag      60
tttctgcaac gcaggccaag tcaccttacc ggaaaacaga gaaccccctgc gcccagaggt    120 gcctccagag ttgtcaacag gaaccggacg acttgaagca aaaggcatgc gagtctcgct    180
gcaccaagct cgagtatgat cctcgttgtg tctatgacac tggcgccacc aaccaacgtc    240
accctccagg ggagcggaca cgtgccgccc aacccggaga ctacgatgat gaccgccgtc    300
aaccccgaag agaggaagga ggccgatggg gaccagctga accgagggag cgtgaaagag    360
aagaagactg gagacaacca agagaagatt ggaggcgacc aagtcatcag cagccacgga    420
```

-continued

```
aaataaggcc cgaaggaaga gaaggagaac aagagtgggg aacaccaggt agcgaggtga    480
gggaagaaac atcacggaac aaccctttct acttcccgtc aaggcggttt agcacccgct    540
acgggaacca aaacggtagg atccgcgtcc tgcagaggtt tgaccaaagg tcaaagcagt    600
ttcagaatct ccagaatcac cgtattgtgc agatcgaggc cagacctaac actcttgttc    660
ttcccaagca cgctgatgct gataacatcc ttgttatcca gcaaggacaa gccaccgtga    720
ccgtagcaaa tggcaataac agaaagagct ttaatcttga cgagggccat gcactcagaa    780
tcccatccgg tttcatttcc tacatcttga atcgacatga caaccagaac ctcagagtag    840
ctaaaatctc catgcccgtt aacacgcccg gccagtttga ggatttcttc ccggcgagca    900
gccgagacca atcatcctac ttgcagggat tcagcaggaa tactttggag gccgccttca    960
atgcggaatt caatgagata cggagggtgc tgttagaaga gaatgcagga ggagagcaag   1020
aggagagagg gcagaggcga cggagtactc ggagtagtga taatgaagga gtgatagtca   1080
aagtgtcaaa ggagcacgtt caagaactta ctaagcacgc taaatccgtc tcaaagaaag   1140
gctccgaaga ggaagatatc accaacccaa tcaacttgag agatggcgag cccgatcttt   1200
ctaacaactt tgggaggtta tttgaggtga agccagacaa gaagaacccc cagcttcagg   1260
acctggacat gatgctcacc tgtgtagaga tcaaagaagg agctttgatg ctcccacact   1320
tcaactcaaa ggccatggtc atcgtcgtcg tcaacaaagg aactggaaac cttgaactcg   1380
tagctgtaag aaaagagcaa caacagaggg gacggcggga acaagagtgg gaagaagagg   1440
aggaagatga agaagaggag ggaagtaaca gagaggtgcg taggtacaca gcgaggttga   1500
aggaaggcga tgtgttcatc atgccagcag ctcatccagt agccatcaac gcttcctccg   1560
aactccatct gcttggcttc ggtatcaacg ctgaaaacaa ccacagaatc ttccttgcag   1620
gtgataagga caatgtgata gaccagatag agaagcaagc gaaggattta gcattccctg   1680
gttcgggtga acaagttgag aagctcatca aaaaccagag ggagtctcac tttgtgagtg   1740
ctcgtcctca atctcaatct ccgtcgtctc ctgaaaaaga ggatcaagag gaggaaaacc   1800
aaggagggaa gggtccactc ctttcaattt tgaaggcttt taactgagaa tggaggaaac   1860
ttgttatgta tccataataa gatcacgctt ttgtaatcta ctatccaaaa acttatcaat   1920
aaataaaaac gtttgtgcgt tgtttctcc                                     1949
```

<210> SEQ ID NO 20
<211> LENGTH: 717
<212> TYPE: DNA
<213> ORGANISM: Arachis hypogaea

<400> SEQUENCE: 20

```
gctcaccata ctagtagccc tcgccctttt cctcctcgct gcccacgcat ctgcgaggca     60
gcagtgggaa ctccaaggag acagaagatg ccagagccag ctcgagaggg cgaacctgag    120
gccctgcgag caacatctca tgcagaagat ccaacgtgac gaggattcat atgaacggga    180
cccgtacagc cctagtcagg atccgtacag ccctagtcca tatgatcgga gaggcgctgg    240
atcctctcag caccaagaga ggtgttgcaa tgagctgaac gagtttgaga acaaccaaag    300
gtgcatgtgc gaggcattgc aacagatcat ggagaaccag agcgataggt tgcaggggag    360
gcaacaggag caacagttca agagggagct caggaacttg cctcaacagt gcggccttag    420
ggcaccacag cgttgcgact tggacgtcga aagtggcggc agagacagat actaaacacc    480
tatctcaaaa aaagaaaaga aaagaaaaga aaatagctta tatataagct attatctatg    540
```

-continued

```
gttatgttta gttttggtaa taataaagat catcactata tgaatgtgtt gatcgtgtta    600
actaaggcaa gcttaggtta tatgagcacc tttagagtgc ttttatggcg ttgtctatgt    660
tttgttgctg cagagttgta accatcttga aataatataa aaagatcatg ttttgtt      717
```

<210> SEQ ID NO 21
<211> LENGTH: 2032
<212> TYPE: DNA
<213> ORGANISM: Arachis hypogaea

<400> SEQUENCE: 21

```
aataatcata tatattcatc aatcatctat ataagtagta gcaggagcaa tgagagggag    60
ggtttctcca ctgatgctgt tgctagggat ccttgtcctg gcttcagttt ctgcaacgca   120
tgccaagtca tcaccttacc agaagaaaac agagaacccc tgcgcccaga ggtgcctcca   180
gagttgtcaa caggaaccgg atgacttgaa gcaaaaggca tgcgagtctc gctgcaccaa   240
gctcgagtat gatcctcgtt gtgtctatga tcctcgagga cacactggca ccaccaacca   300
acgttcccct ccaggggagc ggacacgtgg ccgccaaccc ggagactacg atgatgaccg   360
ccgtcaaccc cgaagagagg aaggaggccg atggggacca gctggaccga gggagcgtga   420
aagagaagaa gactggagac aaccaagaga agattggagg cgaccaagtc atcagcagcc   480
acggaaaata aggcccgaag gaagagaagg agaacaagag tggggaacac caggtagcca   540
tgtgagggaa gaaacatctc ggaacaaccc tttctacttc ccgtcaaggc ggtttagcac   600
ccgctacggg aaccaaaacg gtaggatccg ggtcctgcag aggtttgacc aaaggtcaag   660
gcagtttcag aatctccaga atcaccgtat tgtgcagatc gaggccaaac ctaacactct   720
tgttcttccc aagcacgctg atgctgataa catccttgtt atccagcaag ggcaagccac   780
cgtgaccgta gcaaatggca ataacagaaa gagctttaat cttgacgagg ccatgcact   840 cagaatccca tccggtttca tttcctacat cttgaaccgc catgacaacc agaacctcag   900
agtagctaaa atctccatgc ccgttaacac acccggccag tttgaggatt tcttcccggc   960
gagcagccga gaccaatcat cctacttgca gggcttcagc aggaatacgt tggaggccgc   1020
cttcaatgcg gaattcaatg agatacggag ggtgctgtta aagagaatgc aggaggtga   1080 gcaagaggag agagggcaga ggcgatggag tactcggagt agtgagaaca atgaaggagt   1140
gatagtcaaa gtgtcaaagg agcacgttga agaacttact aagcacgcta atccgtctc   1200 aaagaaaggc tccgaagaag agggagatat caccaaccca atcaacttga gagaaggcga   1260
gcccgatctt tctaacaact ttgggaagtt atttgaggtg aagccagaca gaagaaccc   1320 ccagcttcag gacctggaca tgatgctcac ctgtgtagag atcaaagaag gagctttgat   1380
gctcccacac ttcaactcaa aggccatggt tatcgtcgtc gtcaacaaag gaactggaaa   1440
ccttgaactc gtggctgtaa gaaaagagca acaacagagg ggacggcggg aagaagagga   1500
ggacgaagac gaagaagagg agggaagtaa cagagaggtg cgtaggtaca cagcgaggtt   1560
gaaggaaggc gatgtgttca tcatgccagc agctcatcca gtagccatca acgcttcctc   1620
cgaactccat ctgcttggct tcggtatcaa cgctgaaaac aaccacagaa tcttccttgc   1680
aggtgataag gacaatgtga tagaccagat agagaagcaa gcgaaggatt tagcattccc   1740
tgggtcgggt gaacaagttg agaagctcat caaaaaccag aaggaatctc actttgtgag   1800
tgctcgtcct caatctcaat ctcaatctcc gtcgtctcct gagaaagagt ctcctgagaa   1860
agaggatcaa gaggaggaaa accaaggagg gaagggtcca ctcctttcaa ttttgaaggc   1920
ttttaactga gaatggaggc aacttgttat gtatcgataa taagatcacg cttttgtact   1980
```
ctactatcca aaaacttatc aataaataaa aacgtttgtg cgttgtttct cc    2032

<210> SEQ ID NO 22
<211> LENGTH: 157
<212> TYPE: PRT
<213> ORGANISM: Arachis hypogaea

<400> SEQUENCE: 22

```
Leu Thr Ile Leu Val Ala Leu Ala Leu Phe Leu Leu Ala Ala His Ala
  1               5                  10                  15

Ser Ala Arg Gln Gln Trp Glu Leu Gln Gly Asp Arg Arg Cys Gln Ser
             20                  25                  30

Gln Leu Glu Arg Ala Asn Leu Arg Pro Cys Glu Gln His Leu Met Gln
         35                  40                  45

Lys Ile Gln Arg Asp Glu Asp Ser Tyr Glu Arg Asp Pro Tyr Ser Pro
     50                  55                  60

Ser Gln Asp Pro Tyr Ser Pro Ser Pro Tyr Asp Arg Arg Gly Ala Gly
 65                  70                  75                  80

Ser Ser Gln His Gln Glu Arg Cys Cys Asn Glu Leu Asn Glu Phe Glu
                 85                  90                  95

Asn Asn Gln Arg Cys Met Cys Glu Ala Leu Gln Gln Ile Met Glu Asn
            100                 105                 110

Gln Ser Asp Arg Leu Gln Gly Arg Gln Gln Glu Gln Gln Phe Lys Arg
        115                 120                 125

Glu Leu Arg Asn Leu Pro Gln Gln Cys Gly Leu Arg Ala Pro Gln Arg
    130                 135                 140

Cys Asp Leu Asp Val Glu Ser Gly Gly Arg Asp Arg Tyr
145                 150                 155
```

<210> SEQ ID NO 23
<211> LENGTH: 2041
<212> TYPE: DNA
<213> ORGANISM: Arachis hypogaea

<400> SEQUENCE: 23
aataatcata tatattcatc aatcatctat ataagtagta gcaggagcaa tgagagggag    60
ggtttctcca ctgatgctgt tgctagggat ccttgtcctg gcttcagttt ctgcaacgca   120
tgccaagtca tcaccttacc agaagaaaac agagaacccc tgcgcccaga ggtgcctcca   180
gagttgtcaa caggaaccgg atgacttgaa gcaaaaggca tgcgagtctc gctgcaccaa   240
gctcgagtat gatcctcgtt gtgtctatga tcctcgagga cacactgca ccaccaacca   300 acgttcccct ccaggggagc ggacacgtgg ccgccaaccc ggagactacg atgatgaccg   360
ccgtcaaccc cgaagagagg aaggaggccg atgggaccag gctggaccga gggagcgtga   420
aagagaagaa gactggagac aaccaagaga agattggagg cgaccaagtc atcagcagcc   480
acggaaaata aggcccgaag aagagaagg agaacaagag tggggaacac caggtagcca   540
tgtgagggaa gaaacatctc ggaacaaccc tttctacttc ccgtcaaggc ggtttagcac   600
ccgctacggg aaccaaaacg gtaggatccg ggtcctgcag aggtttgacc aaaggtcaag   660
gcagtttcag aatctccaga atcaccgtat tgtgcagatc gaggccaaac ctaacactct   720
tgttcttccc aagcacgctg atgctgataa catccttgtt atccagcaag ggcaagccac   780
cgtgaccgta gcaaatggca ataacagaaa gagctttaat cttgacgagg ccatgcact    840 cagaatccca tccggtttca tttcctacat cttgaaccgc catgacaacc agaacctcag   900

-continued

```
agtagctaaa atctccatgc ccgttaacac acccggccag tttgaggatt tcttcccggc      960
gagcagccga gaccaatcat cctacttgca gggcttcagc aggaatacgt tggaggccgc     1020
cttcaatgcg gaattcaatg agatacggag ggtgctgtta aagagaatg caggaggtga      1080
gcaagaggag agagggcaga ggcgatggag tactcggagt agtgagaaca atgaaggagt     1140
gatagtcaaa gtgtcaaagg agcacgttga agaacttact aagcacgcta aatccgtctc    1200
aaagaaaggc tccgaagaag agggagatat caccaaccca atcaacttga gagaaggcga    1260
gcccgatctt tctaacaact ttgggaagtt atttgaggtg aagccagaca agaagaaccc    1320
ccagcttcag gacctggaca tgatgctcac ctgtgtagag atcaaagaag gagctttgat    1380
gctcccacac ttcaactcaa aggccatggt tatcgtcgtc gtcaacaaag gaactggaaa    1440
ccttgaactc gtggctgtaa gaaaagagca acaacagagg ggacggcggg aagaagagga   1500
ggacgaagac gaagaagagg agggaagtaa cagagaggtg cgtaggtaca cagcgaggtt    1560
gaaggaaggc gatgtgttca tcatgccagc agctcatcca gtagccatca acgcttcctc    1620
cgaactccat ctgcttggct tcggtatcaa cgctgaaaac aaccacagaa tcttccttgc    1680
aggtgataag gacaatgtga tagaccagat agagaagcaa gcgaaggatt tagcattccc    1740
tgggtcgggt gaacaagttg agaagctcat caaaaaccag aaggaatctc actttgtgag    1800
tgctcgtcct caatctcaat ctcaatctcc gtcgtctcct gagaaagagt ctcctgaaa    1860
agaggatcaa gaggaggaaa accaaggagg gaagggtcca ctcctttcaa ttttgaaggc    1920
ttttaactga gaatggaggc aacttgttat gtatcgataa taagatcacg cttttgtact    1980
ctactatcca aaaacttatc aataaataaa aacgtttgtg cgttgtttct ccaaaaaaaa    2040
a                                                                    2041
```